United States Patent
Singh et al.

(10) Patent No.: US 10,184,940 B2
(45) Date of Patent: Jan. 22, 2019

(54) ANTIBODIES TO MICROBIOME, STRESS FACTORS AND MAST CELL MARKERS AS DIAGNOSTIC MARKERS FOR IBS

(71) Applicant: NESTEC S.A., Vevey (CH)

(72) Inventors: Sharat Singh, Rancho Santa Fe, CA (US); Nicholas Chi-Kwan Ling, San Diego, CA (US); Shui-Long Wang, San Diego, CA (US); Fred Princen, La Jolla, CA (US); Stefan Westin, Carlsbad, CA (US); Steven Lockton, San Diego, CA (US)

(73) Assignee: Nestec S.A., Vevey (CH)

( * ) Notice: Subject to any disclaimer, the term of this patent is extended or adjusted under 35 U.S.C. 154(b) by 776 days.

(21) Appl. No.: 14/673,660

(22) Filed: Mar. 30, 2015

(65) Prior Publication Data

US 2015/0346200 A1    Dec. 3, 2015

Related U.S. Application Data

(63) Continuation of application No. PCT/IB2013/059045, filed on Oct. 1, 2013.

(60) Provisional application No. 61/871,853, filed on Aug. 29, 2013, provisional application No. 61/710,574, filed on Oct. 5, 2012.

(51) Int. Cl.
*G01N 33/48* (2006.01)
*G01N 33/569* (2006.01)
*G01N 33/564* (2006.01)

(52) U.S. Cl.
CPC ..... *G01N 33/56911* (2013.01); *G01N 33/564* (2013.01); *G01N 33/569* (2013.01); *G01N 2800/065* (2013.01); *G01N 2800/60* (2013.01)

(58) Field of Classification Search
CPC ................................................ G01N 33/56911

USPC .......................................................... 702/19
See application file for complete search history.

(56) References Cited

U.S. PATENT DOCUMENTS

| 7,943,328 B1 | 5/2011 | Lois et al. |
| 2006/0154276 A1 | 7/2006 | Lois et al. |
| 2007/0275424 A1 | 11/2007 | Gewirtz et al. |
| 2010/0094560 A1 | 4/2010 | Lois et al. |

FOREIGN PATENT DOCUMENTS

| JP | 2009-524008 | 6/2009 |
| JP | 2010-506144 | 2/2010 |
| WO | 2007/064964 | 6/2007 |
| WO | 2008/022177 | 2/2008 |
| WO | 2011/053831 | 5/2011 |

OTHER PUBLICATIONS

Chen, C. et al., "Identification of novel serological biomarkers for inflammatory bowel disease using *Escherichia coli* proteome chip," Mol. Cel. Proteomics, 8(8):1765-1776, 2009.

Plevy, S. et al., "Combined serologic, genetic, and inflammatory markers can accurately differentiate non-IBD, Crohn's disease, and ulcerative colitis patients," Gastroenterology, 142(5, Supp. 1):S-41, 2012.

*Primary Examiner* — Jerry Lin
(74) *Attorney, Agent, or Firm* — Kilpatrick Townsend & Stockton LLP

(57) ABSTRACT

The present invention provides methods for aiding in the diagnosis of irritable bowel syndrome (IBS) in an individual. In particular, the present invention is useful for determining whether a sample from an individual is an IBS sample or a healthy control sample using a statistical algorithm. Thus, the present invention provides an accurate diagnostic prediction of IBS and is useful for guiding treatment decisions.

22 Claims, 29 Drawing Sheets

Specification includes a Sequence Listing.

FIG. 17A

- AM linear regression
  – Cortisol vs. Dx

| | Estimate | P |
|---|---|---|
| HC vs. IBS-C | -0.142 | 0.433 |
| HC vs. IBS-D | -0.374 | 0.056 |
| HC vs. IBS-M | -0.063 | 0.732 |

FIG. 17B

- PM linear regression
  – Cortisol vs. Dx

| | Estimate | P |
|---|---|---|
| HC vs. IBS-C | -0.502 | 0.062 |
| HC vs. IBS-D | -0.636 | 0.012 |
| HC vs. IBS-M | 0.022 | 0.942 |

|  | Estimate | Std. Error | T-value | Pr(>|t|) |  |
| --- | --- | --- | --- | --- | --- |
| (Intercept) | 3.5361 | 3.3985 | 1.0400 | 0.3008 |  |
| CjFlaA | -0.0221 | 0.1907 | -0.1160 | 0.9080 |  |
| CjFlaB | 0.3847 | 0.2163 | 1.7780 | 0.0785 | . |
| EcEra | 0.0454 | 0.3785 | 0.1200 | 0.9047 |  |
| EcFliC | -0.2979 | 0.2812 | -1.0600 | 0.2920 |  |
| EcGabT | 0.4647 | 0.2355 | 1.9740 | 0.0513 | . |
| EcOFliC | -0.2110 | 0.0847 | -2.4910 | 0.0145 | * |
| CRP | 0.2027 | 0.1539 | 1.3170 | 0.1910 |  |
| SAA | 0.0239 | 0.1402 | 0.1710 | 0.8650 |  |
| ICAM | -0.0734 | 0.3239 | -0.2270 | 0.8211 |  |
| VCAM | 0.0031 | 0.2316 | 0.0140 | 0.9892 |  |
| PlI | -1.2749 | 1.0748 | -1.1860 | 0.2385 |  |
| SfFlic | -0.1025 | 0.1007 | -1.0180 | 0.3112 |  |
| GROA | 0.0480 | 0.0991 | 0.4840 | 0.6293 |  |
| PGE2 | -0.1335 | 0.1132 | -1.1800 | 0.2411 |  |
| Histamine | -0.0330 | 0.1335 | -0.2470 | 0.8053 |  |
| Tryptase | -0.0764 | 0.0996 | -0.7670 | 0.4449 |  |
| TWEAK | -0.0721 | 0.2193 | -0.3290 | 0.7430 |  |
| BDNF | 0.0361 | 0.1892 | 0.1910 | 0.8492 |  |

*FIG. 21*

ANTIBODIES TO MICROBIOME, STRESS FACTORS AND MAST CELL MARKERS AS DIAGNOSTIC MARKERS FOR IBS

CROSS-REFERENCES TO RELATED APPLICATIONS

This application is a continuation of PCT/IB2013/059045 filed Oct. 1, 2013, which application claims priority from U.S. Provisional Application No. 61/710,574, filed Oct. 5, 2012 and U.S. Provisional Application No. 61/871,853, filed Aug. 29, 2013, the disclosures all of which are hereby incorporated by reference in their entireties for all purposes.

REFERENCE TO A SEQUENCE LISTING

The Sequence Listing written in file Substitute-Sequence-Listing_88473-025320US-939021.txt, created on, Aug. 23, 2015, 63,172 bytes, machine format IBM-PC, MS-Windows operating system, is hereby incorporated by reference in its entirety for all purposes.

BACKGROUND OF THE INVENTION

Irritable bowel syndrome is a clinically heterogeneous disorder with a worldwide prevalence of 10-20% (Longstreth et al., *Gastroenterology*, 130:1480-1491 (2006)). According to the Rome III criteria, patients with IBS can be categorized into four symptom subtypes based on the stool consistency: diarrhea predominant (IBS-D), constipation predominant (IBS-C), mixed subtype (IBS-M) with alternating episodes of both diarrhea and constipation, and unsubtyped IBS (IBS-U).

Current research has implicated the gastrointestinal microbiota and the brain-gut axis in the pathophysiology of IBS. Abdominal pain and discomfort associated with IBS is connected to the brain-gut axis and the response to stress hormones. Studies have shown that gastrointestinal microbiota of IBS patients is altered from that of healthy controls. There is also evidence that gastrointestinal microbiota causes post-infectious IBS (PI-IBS). IBS has been associated with aberrant gastrointestinal microbiota, and even bacterial overgrowth (Kim et al., *Digestive Diseases and Sciences*, May 2012).

Flagellin, the primary structural component of bacterial flagella, has been shown to activate both the innate and adaptive immune system in individuals. For example, antibodies against bacteria flagellin (A4-Fla2 and Fla-X) have been detected more frequently in patients with IBS than in healthy controls (p=0.004 and p=0.009, respectively; Schoepfer et al., *Neurogastroenterol. Motil.* 20:1110-1118 (2008)).

There is a growing body of evidence supporting the role of gut microbiome, stress hormones, inflammatory cytokines, and mast cell markers in various intestinal diseases or disorders. For instance, the antibodies to OmpC, Cbir1, FlaX and Fla2 have been proven to be valuable biomarkers of inflammatory bowel disease (IBD). Subsets of antibodies to *Escherichia coli* K12 proteins (e.g., Era, FocA, FrvX, GabT, YbaN, YcdG, YhgN, YedK, and YidX) can be used to distinguish between individuals with Crohn's Disease (CD) and healthy controls, and between individuals with CD and ulcerative colitis (Chen et al., *Mol. Cell Proteomics*, 8:1765-1776, (2009)). Individuals with post-infectious small intestine bacterial outgrowth (SIBO) associated with IBS which is often caused by infection from *Campylobacter jejuni* (*C. jejuni*, Cj), *Escherichia coli* (*E. coli*, Ec), *Salmonella enteritidis* (*S. enteritidis*, Se), *Shigella flexneri* (*S. flexneri*, Sf), may possess antibodies against flagellin proteins of the infecting bacteria (Spiller R and Garsed K., *Gastroenterology*, 136:1979-1988 (2009)).

Interestingly, treatments that target gastrointestinal microbiota such as antibiotics, probiotics and prebiotics appear to alleviate the symptoms of IBS. For instance, the antibiotic rifaximin appears to affect gut bacteria and reduce bacterial products that negatively affect the host individual.

In addition to the gut microbiome, mast cells also play an important role in the pathogenesis of IBS. Increased mast cell infiltration and activation in distal gut segments are associated with symptom onset and severity of IBS. These cells are also implicated in the elevated response of visceral afferent nerves to mucosal stimulus in IBS patients. Mast cell hyperplasia is commonly observed following infection by these bacteria in both post-infectious IBS and non-post-infectious IBS. Measurement of mast cell markers such as β-tryptase, histamine and prostaglandin E2 (PGE2) have important implications in the clinical diagnosis of IBS. Detailed methods of using mast cell markers to aid in the diagnosis of IBS are described in U.S. Pat. No. 8,114,616 and U.S. Patent Publication No. 2012/244558, the disclosures of which are hereby incorporated by reference in their entireties for all purposes.

IBS patients typically experience abnormal gut motility and visceral hypersensitivity mediated by the brain-gut axis or central stress response system. One arm of the brain-gut axis is the central efferent pathway, which is formed by the sympathetic nervous system and the hypothalamic-pituitary-adrenal axis (HPA). In stress-sensitive disorders including IBS, stress hormones of the HPA axis, such as adrenocorticotropin hormone (ACTH), cortisol, and catecholamine are released. Some studies have shown that the HPA axis response in IBS patients is caused by increased mucosal immune activation, which in turn increases plasma cytokine levels to stimulate the HPA axis. It has been theorized that a blunted stress response contributes to the symptoms of IBS. Moreover, symptoms of IBS due to increased expression of mast cell markers and altered microbiota antigen/antibody composition are thought to be exacerbated by an altered immune response caused by a dysregulated brain-gut axis.

In view of the foregoing, there is a need in the art for methods and kits that for differentially diagnose IBS from non-IBS samples. The present invention satisfies this and other needs.

BRIEF SUMMARY OF THE INVENTION

In one aspect, the present invention provides methods for aiding in the diagnosis of irritable bowel syndrome (IBS) in a subject. In one instance, the method comprises:
  measuring the level of an array of bacterial antigen antibody markers in a biological sample taken from the subject;
  applying a statistical analysis to the measured level of the array of bacterial antigen antibody markers to generate a bacterial antigen antibody profile; and
  comparing the bacterial antigen antibody profile to a diagnostic model to determine whether the individual has an increased likelihood of having IBS compared to being a healthy control.

In some embodiments, the array of bacterial antigen antibody markers is selected form from the group consisting of antibodies against: *E. coli* FliC, *S. flexneri* FliC, *C. jejuni* FlaA, *C. jejuni* FlaB, *E. coli* O157:H7 FliC, *E. coli* FrvX, *E.* coli GabT, *C. jejuni* 81-045, *C. jejuni* 81-128, and *C. jejuni* 81-008, *E. coli* Era, *E. coli* FocA, *E. coli* FrvX, *E. coli* GabT, *E. coli* YbaN, *E. coli* YcdG, *E. coli* YhgN, *E. coli* YedK, *E. coli* YidX, *L. acidophilus* Frc, *L. acidophilus* Eno, *L. johnsonii* EFTu, *B. fragilis* OmpA, *Prevotella* OmpA, *C. perfringens* 10bA, *C. perfringens* SpA, *E. faecalis* Sant, *L. monocytogenes* Osp, and combinations thereof.

In some embodiments, the antibody specifically binds to a bacterial antigen selected from the group consisting of SfFliC, CjFlaA, CjFlaB, EcOFliC, SeFljB, CjGT-A, Cjdmh, CjCgtA and a combination thereof.

In some embodiments, the antibody specifically binds to a bacterial antigen selected from the group consisting of EcFliC, EcEra, EcFocA, EcFrvX, EcGabT, EcYbaN, EcYcdG, EcYhgN, EcYidX, EcYedK, and combinations thereof.

In some embodiments, the antibody specifically binds to a bacterial antigen selected from the group consisting of LaFrc, LaEno, LjEFTu, BJOmpA, PrOmpA, Cp10bA, CpSpA, EfSant, LmOsp, and combinations thereof.

In some embodiments, the step of measuring the level of an array of bacterial antigen antibody markers comprises:
  contacting the sample with at least one bacterial antigen or an antigenic fragment thereof to transform the bacterial antigen antibody present in the sample into a complex comprising at least one bacterial antigen or the antigenic fragment thereof and the bacterial antigen antibody;
  contacting the complex with a detection antibody under conditions suitable to form a ternary complex comprising at least one bacterial antigen or the antigenic fragment thereof, the bacterial antigen antibody and the detection antibody; and
  detecting the ternary complex which correlates to the level of at least one bacterial antigen antibody marker.

In some embodiments, the statistical analysis transforms the level of the array of antibody markers into a bacterial antigen antibody marker profile.

In some embodiments, the diagnostic model comprises a bacterial antigen antibody marker model. In some embodiments, the diagnostic model is established using a retrospective cohort with known outcomes of a clinical subtype of IBS and healthy controls.

In some embodiments, the bacterial antigen antibody model is derived by applying logistic regression analysis to the level of one or more bacterial antigen antibody marker determined in the retrospective cohort.

In some embodiments the method further comprises
  determining the level of an array of mast cell markers in a biological sample taken from the subject;
  applying a statistical analysis to the measured level of the array of mast cell markers to generate a mast cell marker profile; and
  comparing the mast cell profile to a diagnostic model to determine whether the individual has an increased likelihood of having IBS compared to being a healthy control.

In some embodiments, the array of mast cell markers is selected from the group consisting of β-tryptase, histamine, prostaglandin E2, and combinations thereof.

In some embodiments, the statistical analysis transforms the level of the array of mast cell markers into a mast cell profile.

In some embodiments the method further comprises
  determining the level of an array of stress factor markers in a biological sample taken from the subject;
  applying a statistical analysis to the measured level of the array of stress factor markers to generate a stress factor profile; and
  comparing the stress factor profile to a diagnostic model to determine whether the individual has an increased likelihood of having IBS compared to being a healthy control.

In some embodiments, the array of stress factors is selected from the group consisting of cortisol, BDNF, serotonin, CRF, ACTH, and combinations thereof.

In some embodiments, the statistical analysis transforms the level of the array of stress factor markers into a stress factor profile.

In some embodiments, the diagnostic model is established using a retrospective cohort with known outcomes of a clinical subtype of IBS and healthy controls. In some embodiments, the diagnostic model comprises a bacterial antigen antibody marker model, a mast cell marker model and/or stress factor marker model.

In some embodiments, the mast cell marker model is derived by applying logistic regression analysis to the level of one or more mast cell marker determined in the retrospective cohort.

In some embodiments, the bacterial antigen antibody marker model is derived by applying logistic regression analysis to the level of one or more bacterial antigen antibody marker determined in the retrospective cohort.

In some embodiments, the mast cell marker model is derived by applying logistic regression analysis to the level of one or more mast cell marker determined in the retrospective cohort.

In some embodiments, the stress factor marker model is derived by applying logistic regression analysis to the level of one or more stress factor marker determined in the retrospective cohort.

In some embodiments, the method further comprises classifying a diagnosis of IBS as IBS-constipation (IBS-C), IBS diarrhea (IBS-D), IBS-mixed (IBS-M), IBS-alternating (IBS-A), or post-infectious IBS (IBS-PI).

In one aspect, the present invention provides methods for aiding in the diagnosis of IBS in a subject. In some instances, the method comprises: (a) contacting a biological sample from the subject with a bacterial antigen antibody-binding moiety (e.g., a bacterial antigen or antigenic fragment thereof) under conditions suitable to transform the bacterial antigen antibody present in the sample into a complex comprising the bacterial antigen antibody and the bacterial antigen-binding moiety and determining the level of the complex, thereby determining the level of the bacterial antigen antibody present in the sample.

In some embodiments, the method further comprises: comparing the level of the bacterial antigen antibody present in the sample to a control level of the bacterial antigen antibody, wherein the level of the bacterial antigen antibody is indicative of an increased likelihood of the subject having IBS.

In some embodiments, the bacterial antigen is selected from the group consisting of EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and combinations thereof.

In some embodiments, the control level of the bacterial antigen antibody is the level of the bacterial antigen antibody in a sample from a healthy control subject.

In some embodiments, the method further comprises determining the level of a mast cell marker in a biological sample from the subject; and comparing the level of the mast cell marker present in the sample to a control level, wherein an increased level of the mast cell marker in the sample from the subject is indicative of an increased likelihood of the subject having IBS.

In some embodiments, the mast cell marker is selected from the group consisting of β-tryptase, histamine, prostaglandin E2, and combinations thereof.

In some embodiments, the control level of the mast cell marker is the level of the mast cell marker in a sample from a healthy control subject.

In some embodiments, the method further comprises classifying a diagnosis of IBS as IBS-constipation (IBS-C), IBS diarrhea (IBS-D), IBS-mixed (IBS-M), IBS-alternating (IBS-A), or post-infectious IBS (IBS-PI).

In another aspect, the present invention provides methods for monitoring the progression of irritable bowel syndrome in a subject, the method comprising:
  a) measuring the levels of an array of bacterial antibody markers, an array of mast cell markers, and optionally an array of stress factor markers in a biological sample taken from the subject at a plurality of time points;
  b) applying a statistical analysis to the measured levels of the selected bacterial antigen antibody markers, mast cell markers, and optionally stress factor markers to generate a disease activity profile over time, wherein the disease activity profile comprises a representation of the level of the selected bacterial antigen antibody markers, mast cell markers, and optionally stress factor markers over time; and
  c) determining whether the subject is undergoing IBS progression.

In certain embodiments, the plurality of time points comprises at least 2, 3, 4, 5, 6, 7, 8, 9, 10, 11, 12, 13, 14, 15, 16, 17, 18, 19, 20, 25, 30, 35, 40, 45, 50, or more time points. In other instances, the first time point in the plurality of time points is during the course of therapy. As non-limiting examples, each of the markers can be measured prior to therapy and/or during the course of therapy at one or more (e.g., a plurality) of the following weeks: 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 52, 54, 56, 58, 60, 62, 64, 66, 68, 70, 80, 90, 100, etc.

In certain embodiments, the therapy is the administration of a probiotic and/or a prebiotic.

In some embodiments, the present invention provides methods for classifying a diagnosis of IBS in a subject, said method comprising:
  a) measuring the levels of an array of bacterial antigen antibody markers, an array of mast cell markers, and optionally an array of stress factor markers in a biological sample taken from the subject;
  b) applying a statistical analysis to the measured levels of the selected bacterial antigen antibody markers, mast cell markers, and optionally stress factor markers to generate a disease classification profile, wherein the disease classification profile comprises a representation of the level of the selected bacterial antigen antibody markers, mast cell markers, and optionally stress factor markers; and
  c) comparing the disease classification profile of the subject to that of a control to determine whether the subject has IBS-constipation (IBS-C), IBS diarrhea (IBS-D), IBS-mixed (IBS-M), IBS-alternating (IBS-A), or post-infectious IBS (IBS-PI).

In some embodiments, the disease classification profile of the control comprises a disease classification profile from a subject who is a healthy control, a subject with IBS or a subtype of IBS such as IBS-constipation (IBS-C), IBS diarrhea (IBS-D), IBS-mixed (IBS-M), IBS-alternating (IBS-A), or post-infectious IBS (IBS-PI). In other embodiments, the disease classification profile of the control comprises an average of a plurality of disease classification profiles from a plurality of subjects who represent either healthy controls, subjects with IBS or subjects with a specific subtype of IBS such as IBS-C, IBS-D, IBS-M, IBS-A or IBS-PI.

In another aspect, the present invention provides methods for monitoring the progression of IBS in a subject, the method comprising:
  a) contacting a first biological sample taken from the subject at a first time with a bacterial antigen antibody binding moiety (e.g., a bacterial antigen or antigenic fragment thereof) under conditions suitable to transform the bacterial antigen antibody present in the sample into a complex comprising the bacterial antigen antibody and the bacterial antigen antibody-binding moiety;
  b) determining the level of the complex, thereby determining the level of the bacterial antigen antibody present in the first sample;
  c) contacting a second biological sample taken from the subject at a second time with the bacterial antigen antibody-binding moiety (e.g., a bacterial antigen or antigenic fragment thereof) under conditions suitable to transform the bacterial antigen antibody present in the sample into a complex comprising the bacterial antigen antibody and the bacterial antigen antibody-binding moiety;
  d) determining the level of the complex, thereby determining the level of the bacterial antigen antibody present in the second sample; and
  e) comparing the level of the bacterial antigen antibody present in the first sample to the level of the bacterial antigen antibody present in the second sample, wherein the difference in the level of the bacterial antigen antibody is indicative of the progression of IBS in the subject.

In some embodiments, the bacterial antigen antibody is selected from the group consisting of antibodies against: EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and combinations thereof.

In some embodiments, the method further comprises determining the level of a mast cell marker present in the sample.

In some embodiments, the mast cell marker is selected from the group consisting of β-tryptase, histamine, prostaglandin E2, and combinations thereof.

In some embodiments of the various methods and assays of the present invention, the presence or level of 1, 2, 3, 4, 5, 6, 7, 8, 9, 10, 11, 12, 13, 14, 15, 16, 17, 18, 19, 20, 21, 22, 23, 24, 25, 26, 27, or more bacterial antigen antibody markers, wherein the antibody is against a bacterial antigen shown in Tables 1, 2 or 3 is detected and used to generate a diagnostic marker profile that is useful for predicting IBS. In certain instances, the biomarkers described herein are analyzed using an immunoassay such as an enzyme-linked immunosorbent assay (ELISA) or an immunohistochemical assay.

In one aspect, the present invention provides a method for classifying whether a sample from a subject is associated with irritable bowel syndrome (IBS), the method comprising:
  a) a data acquisition module designed to produce a data set comprising a diagnostic marker profile, wherein the diagnostic marker profile indicates the presence or level of at least one antibody against a bacterial antigen, wherein the bacterial antigen is selected from the group consisting of EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and combinations thereof, or in combination with at least one mast cell marker selected from the group consisting of β-tryptase, histamine, and prostaglandin E2;
  b) a data processing module designed to process the data set by applying a statistical process to the data set to produce a statistically derived decision classifying the sample as an IBS sample or non-IBS sample based upon the diagnostic marker profile; and
  c) a treatment selection module designed to determine a treatment likely to benefit the subject based upon the diagnostic marker profile.

Other objects, features, and advantages of the present invention will be apparent to one of skill in the art from the following detailed description and figures.

BRIEF DESCRIPTION OF THE DRAWINGS

FIGS. 17A-B show that the cortisol level in the p.m. sample was highly predictive of healthy control versus IBS-D. FIG. 17A shows the correlation of cortisol levels between healthy controls (HC) and patients with IBS-C, IBS-D and IBS-M in a.m. samples. FIG. 17B shows the correlation of cortisol levels between healthy controls (HC) and patients with IBS-C, IBS-D and IBS-M in p.m. samples.

FIG. 21 shows the results of multiple linear regression modeling on log-transformed variables. In particular, the table shows the relationship of each marker to cortisol.

DETAILED DESCRIPTION OF THE INVENTION

I. Introduction

Figure 1:
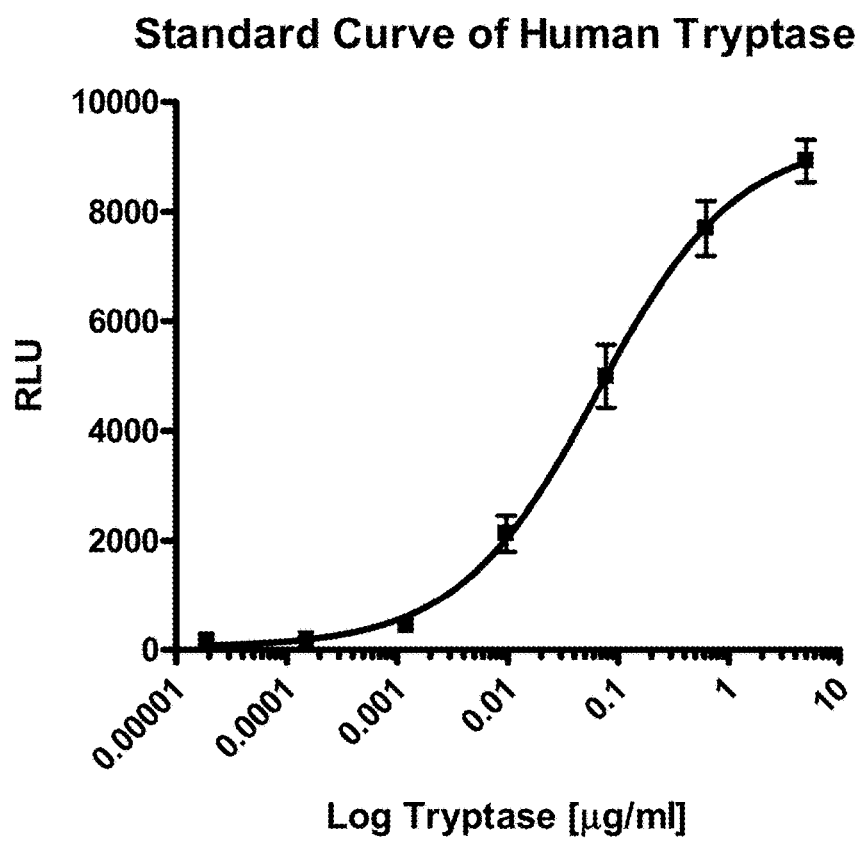
FIG. 1 illustrates a dose response curve of human β-tryptase derived from one embodiment of the present invention.
Figure 2:
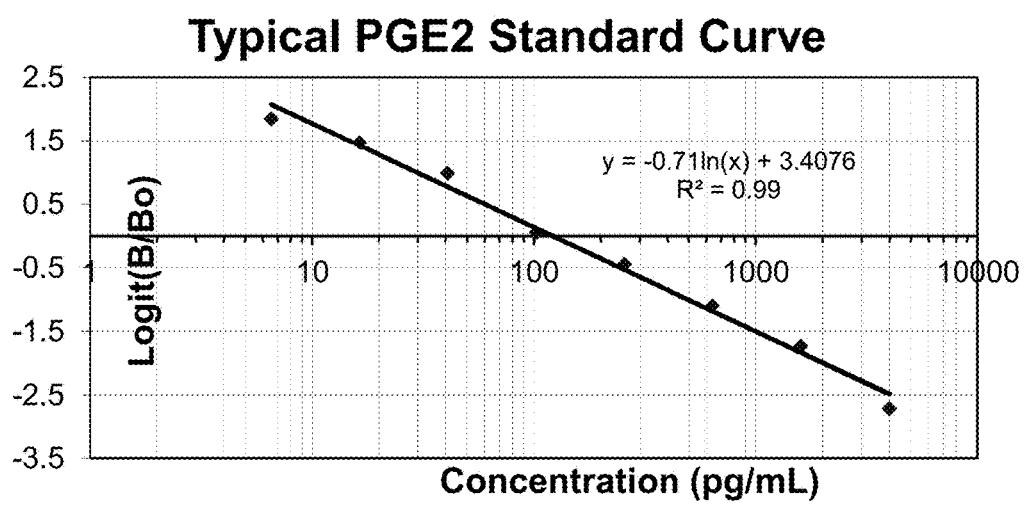
FIG. 2 illustrates a dose response curve of human prostaglandin E2 (PGE2) derived from one embodiment of the present invention.
Figure 3:
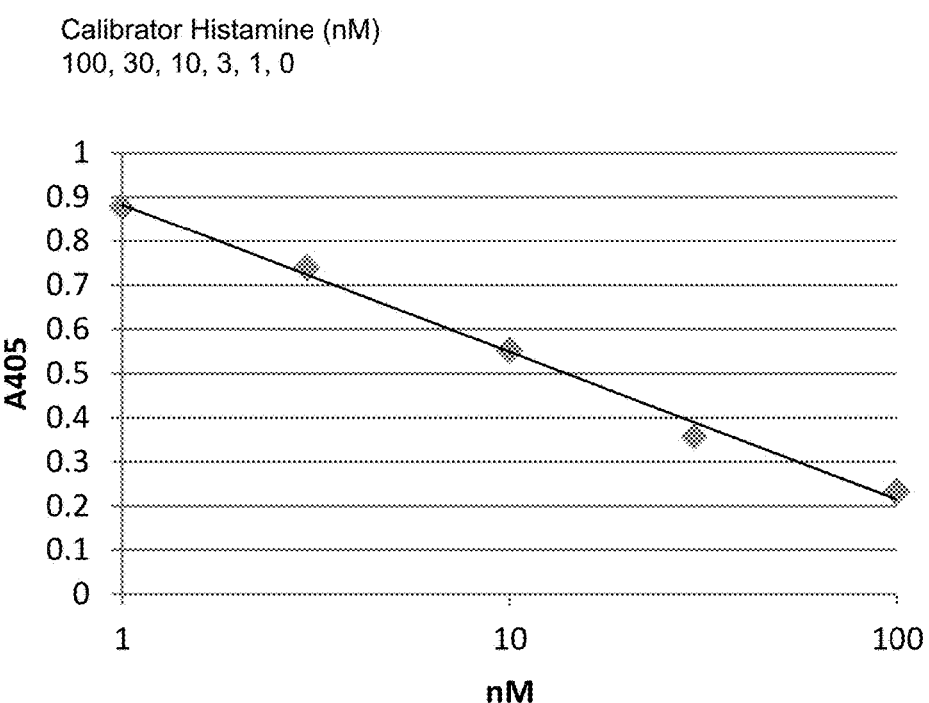
FIG. 3 illustrates a dose response curve of human histamine derived from one embodiment of the present invention.

Diagnosing a patient as having irritable bowel syndrome can be challenging due to the similarity in symptoms between IBS and other intestinal diseases or disorders. Biomarker-based assays can provide rapid and accurate diagnostic methods to distinguish IBS from other diseases and disorders.

Although the precise pathophysiology of IBS remains to be elucidated. It is believed that IBS is caused, in part, by dysregulation of the host's microbiome in the gut and stress hormones. Studies have shown that the gastrointestinal microbiota can influence the host and results in mucosal inflammation and immune activation, and that cortisol levels can be high in women with IBS (Heitkemper et al., *Am J Gastroenterol*, 91(5):906-13 (1996)).

Observations supporting this theory include the finding that an increased number of mast cells can be found in the gastrointestinal mucosa of patients diagnosed with IBS (Guilarte, M. et al., *Gut* 56, 203-209 (2007); Walker, M. M. et al., *Pharmacol. Ther.* 29, 765-773 (2009); Akbar, A. et al., *Gut* 57, 923-929 (2008); Barbara, G. et al., *Gastroenterology* 126, 693-702 (2004); Barbara, G. et al., *Gastroenterology* 132, 26-37 (2007); Cremon, C. et al., *Am. J. Gastroenterol.* 104, 392-400 (2009); and O'Sullivan, M. et al., *Neurogastroenterol. Motil.*, 12, 449-457 (2000)). Similarly, some studies have also found that levels of mediators released from these cells, including histamine and serine proteases (e.g., tryptase), are found in the colonic mucosa of IBS patients (Buhner et al., *Gastroenterology*, 137(4), (2009)); Barbara et al., *Gastroenterology*, 122(4), Suppl. 1: A-276, (2002)).

The human gastrointestinal microbiota includes at least 1,000 species of bacteria, and about $10^{14}$ individual bacterial cells from about 160 different species inhabit each individual's intestine (Qin, J. et al., *Nature*, 464:59-65 (2010)). It has been theorized that the host's (e.g., individual's) genetic and immune composition as well as environmental factors influence the gastrointestinal microbiota, which in turn shapes the host's immunity and physiology within the gastrointestinal system. This theory suggests that a healthy individual (e.g., free of intestinal disorders or disease) maintains a symbiotic relationship with the microbiota colonizing his/her intestines, while an individual with IBS has an imbalance in this microbiota-immune interaction.

The present invention is based, in part, upon the surprising discovery that the levels of antibodies against bacterial antigens (e.g., bacterial antigen antibodies), and optionally, in combination with mast cell markers and/or stress factor markers measured in a biological sample taken from an individual can accurately predict whether the individual has IBS.

In one aspect, the present invention provides methods and assays to aid in the diagnosis of irritable bowel syndrome based on the presence or level of certain bacterial antigen antibody markers and mast cell markers, alone or in combination. In certain embodiments, these methods and assays are related to the detection of the presence and level of various IBS biomarkers in the blood and/or serum of subjects. In preferred embodiments, the method comprises the detection of at least one antibody against a bacterial antigen (e.g., *E. coli* FliC, *S. flexneri* FliC, *C. jejuni* FlaA, *C. jejuni* FlaB, *E. coli* O157:H7 FliC, *E. coli* FrvX, *E. coli* GabT, *C. jejuni* 81-045, *C. jejuni* 81-128, and *C. jejuni* 81-008, *E. coli* Era, *E. coli* FocA, *E. coli* FrvX, *E. coli* GabT, *E. coli* YbaN, *E. coli* YcdG, *E. coli* YhgN, *E. coli* YedK, *E. coli* YidX, *L. acidophilus* Frc, *L. acidophilus* Eno, *L. johnsonii* EFTu, *B. fragilis* OmpA, *Prevotella* OmpA, *C. perfringens* 10bA, *C. perfringens* SpA, *E. faecalis* Sant, and *L. monocytogenes* Osp), or in combination with at least one mast cell marker (e.g., β-tryptase, histamine, and prostaglandin E2) in a blood and/or serum sample from a subject.

In one aspect, the present invention provides methods for monitoring the progression of IBS in a subject, syndrome based on the presence or level of specific bacterial antigen antibody markers, mast cell markers, or in combination thereof over several time points. In certain embodiments, these methods and assays are related to the detection of the presence and level of various IBS biomarkers in the blood and/or serum of subjects at a plurality to time points and comparing the differences in the levels of the IBS biomarkers. In preferred embodiments, the method comprises the detection of at least one antibody against a bacterial antigen (e.g., *E. coli* FliC, *S. flexneri* FliC, *C. jejuni* FlaA, *C. jejuni* FlaB, *E. coli* O157:H7 FliC, *E. coli* FrvX, *E. coli* GabT, *C. jejuni* 81-045, *C. jejuni* 81-128, and *C. jejuni* 81-008, *E. coli* Era, *E. coli* FocA, *E. coli* FrvX, *E. coli* GabT, *E. coli* YbaN,

*E. coli* YcdG, *E. coli* YhgN, *E. coli* YedK, *E. coli* YidX, *L. acidophilus* Frc, *L. acidophilus* Eno, *L. johnsonii* EFTu, *B. fragilis* OmpA, *Prevotella* OmpA, *C. perfringens* 10bA, *C. perfringens* SpA, *E. faecalis* Sant, and *L. monocytogenes* Osp), or in combination with least one mast cell marker (e.g., β-tryptase, histamine, and prostaglandin E2) in a blood and/or serum sample from a subject at a first time point and a second time point. Optionally, the method also includes the detection of at least one stress factor marker (e.g., cortisol and BDNF). The method further comprises comparing the level(s) of the bacterial antigen antibody (antibodies), the combination of bacterial antigen antibody (antibodies), mast cell marker(s), and optionally, stress factor marker(s), wherein the difference in the level(s) is indicative of the progression of IBS in the subject.

In some aspects, the present invention provides methods for classifying whether a sample from an individual is associated with IBS, the method comprising:

a) determining a diagnostic marker profile detecting the presence or level of at least one bacterial antigen antibody marker or in combination with at least one mast cell marker in the sample; and b) classifying the sample as an IBS sample or a non-IBS sample using an algorithm based on the diagnostic marker profile.

In some aspects, the present invention uses statistical algorithms to aid in the classification of a sample as an IBS sample or a non-IBS sample. In other aspects, the present invention uses statistical algorithms for ruling out other intestinal disorders (e.g., IBD).

In one aspect, the present invention further provides methods and assays to aid in selecting a treatment for an individual with IBS.

II. Definitions

As used herein, the following terms have the meanings ascribed to them unless specified otherwise.

The terms "microbiota," "microflora" and "microbiome" refer to the community of living microorganisms that typically inhabits a bodily organ or part. Members of the gastrointestinal microbiota include, but are not limited to, microorganisms of the phyla of Firmicutes, Bacteroidetes, Proteobacteria, Epsilonproteobacteria, Fusobacteria, Alphaproteobacteria, Betaproteobacteria, Gammaproteobacteria, Verrumicrobia, Deltaproteobacteria, Unclassified near cyanobacteria, and Actinobacteria; microorganisms of the *Bacteroides*, *Prevotella* or *Ruminococcus* genera; microorganisms of the *Bifidobacteria*, *Enterobacteraceae*, *Lactobacillus*, *Veillonella*, *Bacteoides*, *Streptococcus*, *Actinomycinaea*, *Helicobacter*, *Peptostreptococcus*, *Collinsella*, *Clostridium*, *Enterococcus*, *Coprococcus*, *Coprobacillus*, *Proteobacteria*, *Lactobacillus*, *Ruminococus*, *Eubacterium*, *Dorea*, *Acinetobacter*, and *Escherichia coli* species; microorganisms of the *Ruminococcus torques*, *R. torques*-like, *Collinsella aerofaciens*-like, *Clostridium cocleatum*, *Eubacterium rectale*, *Clostridium coccoides*, *Rhinobatos productus* types. In some instances, the gastrointestinal microbiota includes the mucosa-associated microbiota, which is located at the surface or apical end of the gastrointestinal tract, and luminal-associated microbiota, which is found in the lumen of the gastrointestinal tract.

The terms "irritable bowel syndrome" and "IBS" includes a group of functional bowel disorders characterized by one or more symptoms including, but not limited to, abdominal pain, abdominal discomfort, change in bowel pattern, loose or more frequent bowel movements, diarrhea, and constipation, typically in the absence of any apparent structural abnormality. There are at least three forms of IBS, depending on which symptom predominates: (1) diarrhea-predominant (IBS-D); (2) constipation-predominant (IBS-C); and (3) IBS with alternating stool pattern (IBS-A). IBS can also occur in the form of a mixture of symptoms (IBS-M). There are also various clinical subtypes of IBS, such as post-infectious IBS (IBS-PI).

The terms "transforming the sample" and "transforming the biomarker" includes a physical and/or chemical change of the sample to extract a marker or to change or modify a marker as defined herein. An extraction, a manipulation, a chemical precipitation, an ELISA, a complexation, an immuno-extraction, a physical or chemical modification of the sample or marker to measure a level or concentration of a marker all constitute a transformation. As long as the sample or marker is not identical before and after the transformation step, the change or modification is a transformation.

The term "biomarker" or "marker" includes any diagnostic marker such as a biochemical marker, serological marker, genetic marker, microbial marker or other clinical or echographic characteristic that can be used to classify a sample from an individual as an IBS sample or to rule out one or more diseases or disorders associated with IBS-like symptoms in a sample from an individual. The term "biomarker" or "marker" also encompasses any classification marker such as an antibody marker, biochemical marker, serological marker, genetic marker, hormonal marker, microbial marker, or other clinical or echographic characteristic that can be used to classify IBS into one of its various forms or clinical subtypes. Non-limiting examples of diagnostic markers suitable for use in the present invention are described below and include antibodies against bacterial antigens, bacterial antigens, flagellins, cytokines, growth factors, stress hormones, anti-neutrophil antibodies, anti-*Saccharomyces cerevisiae* antibodies, antimicrobial antibodies, anti-tissue transglutaminase (tTG) antibodies, lipocalins, matrix metalloproteinases (MMPs), tissue inhibitor of metalloproteinases (TIMPs), alpha-globulins, actin-severing proteins, S100 proteins, fibrinopeptides, calcitonin gene-related peptide (CGRP), tachykinins, ghrelin, neurotensin, serotonin, corticotropin-releasing hormone (CRH), serine proteases (e.g., β-tryptase, elastase), prostaglandin (e.g., PGE2), histamine, C-reactive protein (CRP), lactoferrin, anti-lactoferrin antibodies, calprotectin, hemoglobin, NOD2/CARD15, serotonin reuptake transporter (SERT), tryptophan hydroxylase-1,5-hydroxytryptamine (5-HT), lactulose, and the like. In preferred embodiments, diagnostic markers suitable for use in the present invention are described herein and include, without limitation, an antibody that binds to a microbiota antigen selected from the group consisting of *E. coli* FliC, *S. flexneri* FliC, *C. jejuni* FlaA, *C. jejuni* FlaB, *E. coli* O157:H7 FliC, *E. coli* FrvX, *E. coli* GabT, *C. jejuni* 81-045, *C. jejuni* 81-128, and *C. jejuni* 81-008, *E. coli* Era, *E. coli* FocA, *E. coli* FrvX, *E. coli* GabT, *E. coli* YbaN, *E. coli* YcdG, *E. coli* YhgN, *E. coli* YedK, *E. coli* YidX, *L. acidophilus* Frc, *L. acidophilus* Eno, *L. johnsonii* EFTu, *B. fragilis* OmpA, *Prevotella* OmpA, *C. perfringens* 10bA, *C. perfringens* SpA, *E. faecalis* Sant, *L. monocytogenes* Osp, and mixtures thereof. Examples of classification markers include, without limitation, leptin, SERT, tryptophan hydroxylase-1,5-HT, antrum mucosal protein 8, keratin-8, claudin-8, zonulin, corticotropin releasing hormone receptor-1 (CRHR1), corticotropin releasing hormone receptor-2 (CRHR2), β-tryptase, histamine, prostaglandin E2 (PGE2) and the like. In some embodiments, diagnostic markers can be used to classify IBS into one of its various forms or clinical subtypes. In other embodiments, classification markers can be used to classify a sample as an IBS sample or to rule out one or more diseases or disorders associated with IBS-like symptoms. One skilled in the art will know of additional diagnostic and classification markers suitable for use in the present invention.

The term "stress factor" or "stress hormone" includes cortisol, corticotrophin releasing hormone, thyrotropin, corticotropin-releasing factor (CRF), brain-derived neurotrophic factor (BDNF), adrenocorticotrophic hormone (ACTH), serotonin, dopamine, glutamate, norephinephrine, and the like.

The term "estimate" refers to the estimated partial correlation coefficient of a logistic regression model. (see, FIG. 4).

The "biological sample" includes any biological specimen obtained from an individual. Suitable samples for use in the present invention include, without limitation, whole blood, plasma, serum, saliva, urine, stool (i.e., feces), tears, and any other bodily fluid, or a tissue sample (i.e., biopsy) such as a small intestine or colon sample, and cellular extracts thereof (e.g., red blood cellular extract). In a preferred embodiment, the sample is a blood, plasma, or serum sample. In a more preferred embodiment, the sample is a serum sample. In certain instances, the term "sample" includes, but is not limited to blood, body tissue, blood serum, lymph fluid, lymph node tissue, spleen tissue, bone marrow, or an immunoglobulin enriched fraction derived from one or more of these tissues. The use of samples such as serum, saliva, and urine is well known in the art (see, e.g., Hashida et al., *J. Clin. Lab. Anal.,* 11:267-86 (1997)). One skilled in the art will appreciate that samples such as serum and blood samples can be diluted prior to the analysis of marker levels.

The term "individual," "subject," or "patient" typically refers to humans, but also to other animals including, e.g., other primates, rodents, canines, felines, equines, ovines, porcines, and the like.

The term "classifying" includes "to associate" or "to categorize" a sample with a disease state. In certain instances, "classifying" is based on statistical evidence, empirical evidence, or both. In certain embodiments, the methods and systems of classifying use a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

As used herein, the term "profile" includes any set of data that represents the distinctive features or characteristics associated with a disease or disorder such as IBS. The term encompasses a "diagnostic marker profile" that analyzes one or more diagnostic markers in a sample, a "symptom profile" that identifies one or more IBS-related clinical factors (i.e., symptoms) an individual is experiencing or has experienced, and combinations thereof. A "symptom profile" can include a set of data that represents the presence, severity, frequency, and/or duration of one or more symptoms associated with IBS. For example, a "diagnostic marker profile" can include a set of data that represents the presence or level of one or more diagnostic markers associated with IBS.

In some embodiments, a panel for measuring one or more of the diagnostic markers and/or diagnostic profiles described above can be constructed and used for classifying the sample as an IBS sample or non-IBS sample. One skilled in the art will appreciate that the presence or level of a plurality of diagnostic markers can be determined simultaneously or sequentially, using, for example, an aliquot or dilution of the individual's sample. In certain instances, the level of a particular diagnostic marker in the individual's sample is considered to be elevated when it is at least about 10%, 15%, 20%, 25%, 50%, 75%, 100%, 125%, 150%, 175%, 200%, 250%, 300%, 350%, 400%, 450%, 500%, 600%, 700%, 800%, 900%, or 1000% greater than the level of the same marker in a comparative sample (e.g., a normal, GI control, IBD, and/or Celiac disease sample) or population of samples (e.g., greater than a median level of the same marker in a comparative population of normal, GI control, IBD, and/or Celiac disease samples). In certain other instances, the level of a particular diagnostic marker in the individual's sample is considered to be lowered when it is at least about 5%, 10%, 15%, 20%, 25%, 30%, 35%, 40%, 45%, 50%, 55%, 60%, 65%, 70%, 75%, 80%, 85%, 90%, or 95% less than the level of the same marker in a comparative sample (e.g., a normal, GI control, IBD, and/or Celiac disease sample) or population of samples (e.g., less than a median level of the same marker in a comparative population of normal, GI control, IBD, and/or Celiac disease samples).

As used herein, the term "substantially the same amino acid sequence" includes an amino acid sequence that is similar, but not identical to, the naturally-occurring amino acid sequence. For example, an amino acid sequence that has substantially the same amino acid sequence as a naturally-occurring peptide, polypeptide, or protein can have one or more modifications such as amino acid additions, deletions, or substitutions relative to the amino acid sequence of the naturally-occurring peptide, polypeptide, or protein, provided that the modified sequence retains substantially at least one biological activity of the naturally-occurring peptide, polypeptide, or protein such as immunoreactivity. Comparison for substantial similarity between amino acid sequences is usually performed with sequences between about 6 and 100 residues, preferably between about 10 and 100 residues, and more preferably between about 25 and 35 residues. A particularly useful modification of a peptide, polypeptide, or protein of the present invention, or a fragment thereof, is a modification that confers, for example, increased stability. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

The terms "complex," "immuno-complex," "conjugate," and "immunoconjugate" include, but are not limited to, peptide or antigen bound (e.g., by non-covalent means) to an antibody or an antibody fragment.

The term "monitoring the progression or regression of IBS" includes the use of the methods, systems, and code of the present invention to determine the disease state (e.g., presence or severity of IBS) of an individual. In some embodiments, the methods, systems, and code of the present invention can be used to predict the progression of IBS, e.g., by determining a likelihood for IBS to progress either rapidly or slowly in an individual based on an analysis of diagnostic markers and/or the identification or IBS-related symptoms. In other embodiments, the methods, systems, and code of the present invention can be used to predict the regression of IBS, e.g., by determining a likelihood for IBS to regress either rapidly or slowly in an individual based on an analysis of diagnostic markers and/or the identification or IBS-related symptoms.

The term "bacterial antigen antibody marker profile" includes 1, 2, 3, 4, 5, 6, 7, 8, 9, 10, 11, 12, 13, 14, 15, 16, 17, 18, 19, 20, 21, 22, 23, 24, 25, 26, 27, or more marker(s) of an individual, wherein the marker(s) can be a bacterial antigen antibody marker, such as, but not limited to, an antibody that recognizes (e.g., specifically bind to, forms a complex) with a bacterial antigen, such as *E. coli* FliC, *S. flexneri* FliC, *C. jejuni* FlaA, *C. jejuni* FlaB, *E. coli* O157:H7 FliC, *E. coli* FrvX, *E. coli* GabT, *C. jejuni* 81-045, *C. jejuni* 81-128, and *C. jejuni* 81-008, *E. coli* Era, *E. coli* FocA, *E. coli* FrvX, *E. coli* GabT, *E. coli* YbaN, *E. coli* YcdG, *E. coli* YhgN, *E. coli* YedK, *E. coli* YidX, *L. acidophilus* Frc, *L. acidophilus* Eno, *L. johnsonii* EFTu, *B. fragilis* OmpA, *Prevotella* OmpA, *C. perfringens* 10bA, *C. perfringens* SpA, *E. faecalis* Sant, *L. monocytogenes* Osp, and the like. A statistical analysis can transform the level of the bacterial antigen antibody marker(s) into a bacterial antigen antibody marker profile. In some instances, a statistical analysis is a quartile score and the quartile score for each of the markers can be summed to generate a quartile sum score. In one aspect, a statistical process comprising a single learning statistical classifier system is applied to the data set of the bacterial antigen antibody marker profile to produce a statistically derived decision classifying a sample as an IBS sample or a non-IBS sample (e.g., healthy control sample) based upon the bacterial antigen antibody marker profile, wherein the bacterial antigen antibody marker profile indicates the level of at least one bacterial antigen antibody marker.

The term "mast cell marker profile" includes 1, 2, 3, 4, 5, 6, 7, 8, 9, 10, or more marker(s) of an individual, wherein the marker(s) can be a mast cell marker, such as, but not limited to β-tryptase, histamine, and prostaglandin E2. A statistical analysis transforms the level of the mast cell marker(s) into a mast cell marker profile. In some instances, a statistical analysis is a quartile score and the quartile score for each of the markers can be summed to generate a quartile sum score. In one aspect, a statistical analysis comprises a single learning statistical classifier system is applied to the data set of the mast cell marker profile to produce a statistically derived decision classifying a sample as an IBS sample or a non-IBS sample based upon the mast cell marker wherein the mast cell marker profile indicates the level of at least one mast cell marker.

In quartile analysis, there are three numbers (values) that divide a range of data into four equal parts. The first quartile (also called the "lower quartile") is the number below which lies the 25 percent of the bottom data. The second quartile (the "median quartile") divides the range in the middle and has 50 percent of the data below it. The third quartile (also called the "upper quartile") has 75 percent of the data below it and the top 25 percent of the data above it. As a non-limiting example, quartile analysis can be applied to the concentration level of a marker such as an antibody or other protein marker described herein, such that a marker level in the first quartile (<25%) is assigned a value of 1, a marker level in the second quartile (25-50%) is assigned a value of 2, a marker level in the third quartile (51%-<75%) is assigned a value of 3, and a marker level in the fourth quartile (75%-100%) is assigned a value of 4.

As used herein, "quartile sum score" or "QSS" includes the sum of quartile scores for all of the markers of interest.

As a non-limiting example, a quartile sum score for a panel of 6 markers (e.g., bacterial antigen antibody markers and/or mast cell markers) may range from 6-24, wherein each of the individual markers is assigned a quartile score of 1-4 based upon the presence or absence of the marker, or the level of the marker.

The terms "statistical algorithm" or "statistical analysis" include a learning statistical classifier system. In some instances, the learning statistical classifier system is selected from the group consisting of a random forest, classification and regression tree, boosted tree, neural network, support vector machine, general chi-squared automatic interaction detector model, interactive tree, multiadaptive regression spline, machine learning classifier, and combinations thereof. In certain instances, the statistical algorithm comprises a single learning statistical classifier system. In other embodiments, the statistical algorithm comprises a combination of at least two learning statistical classifier systems. In some instances, the at least two learning statistical classifier systems are applied in tandem. Non-limiting examples of statistical algorithms and analysis suitable for use in the invention are described in International Application No. PCT/US2011/056777, filed Oct. 18, 2011, the disclosure of which is hereby incorporated by reference in its entirety for all purposes.

The term "diagnostic model" includes a bacterial antigen antibody marker profile, a mast cell marker profile, and a combination thereof. In a preferred aspect, a retrospective analysis is done on a cohort of known disease outcomes with known complications and surgical procedures performed, as well as healthy controls. In one aspect, a regression analysis (e.g., logistic regression) can be performed on the level of one or more bacterial antigen antibody markers and/or the level of one or more mast cell markers to develop a diagnostic model.

III. Description of the Embodiments

A. Methods for Aiding in the Diagnosis of Irritable Bowel Syndrome

In one aspect, the present invention provides methods of aiding in the diagnosis of irritable bowel syndrome (IBS) in a subject. In some embodiments, the method comprises:
  a) measuring the level of an array of bacterial antigen antibody markers in a biological sample taken from the subject;
  b) applying a statistical analysis to the measured level of the array of bacterial antigen antibody markers to generate a bacterial antigen antibody marker profile; and
  c) comparing the bacterial antigen antibody marker profile to a diagnostic model to determine whether the individual has an increased likelihood of having IBS compared to being a healthy control.

In some embodiments, the bacterial antigen antibody marker is an antibody against a bacterial antigen, wherein the bacterial antigen is selected from the group consisting of EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and combinations thereof.

In some embodiments, the statistical analysis transforms the level of the array of bacterial antigen antibody markers into a bacterial antigen antibody marker profile.

In some embodiments, the bacterial antigen antibody marker profile includes an empirically derived profile that is based upon an analysis of a plurality of bacterial antigen antibody markers. In one aspect, the concentration of markers or their measured concentration values are transformed into an index by an algorithm resident on a computer. In certain aspects, the profile is a synthetic or human derived output, score, or cut off value(s), which expresses the biological data in numerical terms. The profile can be used to determine or make or aid in making a clinical decision. A bacterial antigen antibody marker profile can be measured multiple times over the course of time. In one aspect, the algorithm can be trained with known samples and thereafter validated with samples of known identity.

In some embodiments, the diagnostic model comprises a bacterial antigen antibody model. In some embodiments, the diagnostic model is established using a retrospective cohort with known outcomes of a clinical subtype of IBS and healthy controls.

In some embodiments, the bacterial antigen antibody model is derived by applying logistic regression analysis to the level of one or more bacterial antigen antibody markers determined in the retrospective cohort.

In some embodiments the method further comprises, and/or alternatively comprises:
d) determining the level of an array of mast cell markers in a biological sample taken from the subject;
e) applying a statistical analysis to the measured level of the array of mast cell markers to generate a mast cell marker profile; and
f) comparing the mast cell marker profile to a diagnostic model to determine whether the individual has an increased likelihood of having IBS compared to being a healthy control.

In some embodiments, the array of mast cell markers is selected from the group consisting of β-tryptase, histamine, prostaglandin E2, and combinations thereof.

In some embodiments, the statistical analysis transforms the level of the array of mast cell markers into a mast cell profile.

In some embodiments the method further comprises and/or alternatively comprises:
d) determining the level of an array of stress hormones markers in a biological sample taken from the subject;
e) applying a statistical analysis to the measured level of the array of stress hormones markers to generate a stress hormone marker profile; and
f) comparing the stress hormone marker profile to a diagnostic model to determine whether the individual has an increased likelihood of having IBS compared to being a healthy control.

In some embodiments, the array of stress hormone markers is selected from the group consisting of cortisol, BDNF, serotonin, CRF, ACTH, and combinations thereof.

In some embodiments, the statistical analysis transforms the level of the array of mast cell markers into a stress hormone profile.

In some embodiments, the diagnostic model is established using a retrospective cohort with known outcomes of a clinical subtype of IBS and healthy controls. In some embodiments, the diagnostic model comprises a bacterial antigen antibody marker model, a mast cell marker model, a stress hormone marker model, or combinations thereof.

In some embodiments, the bacterial antigen antibody model is derived by applying logistic regression analysis to the level of one or more bacterial antigen antibody markers determined in the retrospective cohort.

In some embodiments, the mast cell marker model is derived by applying logistic regression analysis to the level of one or more mast cell markers determined in the retrospective cohort.

In some embodiments, the stress hormone model is derived by applying logistic regression analysis to the level of one or more stress hormones markers determined in the retrospective cohort.

In some embodiments, the method further comprises classifying a diagnosis of IBS as IBS-constipation (IBS-C), IBS diarrhea (IBS-D), IBS-mixed (IBS-M), IBS-alternating (IBS-A), or post-infectious IBS (IBS-PI).

In one aspect, the present invention provides methods for aiding in the diagnosis of irritable bowel syndrome in a subject by determining the level of at least 1, 2, 3, 4, 5, 6, 7, 8, 9, 10, 11, 12, 13, 14, 15, 16, 17, 18, 19, 20, 21, 22, 23, 24, 25, 26, 27, or more bacterial antigen antibody markers, wherein the bacterial antigen antibody marker(s) recognize at least one of the bacterial antigens shown in Tables 1 and 2. In preferred embodiments, the methods provided herein rely on the detection of an antibody against a bacterial antigen selected from the group consisting of EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and combinations thereof.

In some embodiments, the method for aiding in the diagnosis of irritable bowel syndrome (IBS) in a subject comprise determining the level of at least one bacterial antigen antibody marker, wherein the bacterial antigen antibody marker is selected from the group consisting of an antibody against EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and combinations thereof.

In some embodiments, the method for aiding in the diagnosis of IBS in a subject comprise determining the level of at least two bacterial antigen antibody markers, wherein the bacterial antigen antibody marker is selected from the group consisting of antibodies against EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and combinations thereof. For example, the level of two bacterial antigen antibody markers can be measured, such as bacterial antigen antibodies against: EcFliC and SfFliC; EcFliC and CjFlaA; EcFliC and CjFlaB; EcFliC and EcOFliC; EcFliC and CjGT-A; EcFliC and Cjdmh; EcFliC and CjCgtA; EcFliC and SeFljB; EcFliC and EcEra; EcFliC and EcFocA; EcFliC and EcFrvX; EcFliC and EcGabT; EcFliC and EcYbaN; EcFliC and EcYcdG; EcFliC and EcYhgN; EcFliC and EcYedK; EcFliC and EcYidX; EcFliC and LaFrc; EcFliC and LaEno; EcFliC and LjEFTu; EcFliC and BfOmpA; EcFliC and PrOmpA; EcFliC and Cp10bA; EcFliC and CpSpA; EcFliC and EfSant; EcFliC and LmOsp; SfFliC and CjFlaA; SfFliC and CjFlaB; SfFliC and EcOFliC; SfFliC and CjGT-A; SfFliC and Cjdmh; SfFliC and CjCgtA; SfFliC and SeFljB; SfFliC and EcEra; SfFliC and EcFocA; SfFliC and EcFrvX; SfFliC and EcGabT; SfFliC and EcYbaN; SfFliC and EcYcdG; SfFliC and EcYhgN; SfFliC and EcYedK; SfFliC and EcYidX; SfFliC and LaFrc; SfFliC and LaEno; SfFliC and LjEFTu; SfFliC and BfOmpA; SfFliC and PrOmpA; SfFliC and Cp10bA; SfFliC and CpSpA; SfFliC and EfSant; SfFliC and LmOsp; CjFlaA and CjFlaB;

CjFlaA and EcOFliC; CjFlaA and CjGT-A; CjFlaA and Cjdmh; CjFlaA and CjCgtA; CjFlaA and SeFljB; CjFlaA and EcEra; CjFlaA and EcFocA; CjFlaA and EcFrvX; CjFlaA and EcGabT; CjFlaA and EcYbaN CjFlaA and; CjFlaA and EcYcdG; CjFlaA and EcYhgN; CjFlaA and EcYedK; CjFlaA and EcYidX; CjFlaA and LaFrc; CjFlaA and LaEno; CjFlaA and LjEFTu; BfOmpA; CjFlaA and PrOmpA; CjFlaA and Cp10bA; CjFlaA and CpSpA; CjFlaA and EfSant; CjFlaA and LmOsp; CjFlaB and EcOFliC; CjFlaB and CjGT-A; CjFlaB and Cjdmh; CjFlaB and CjCgtA; CjFlaB and SeFljB; CjFlaB and EcEra; CjFlaB and EcFocA; EcFrvX; CjFlaB and EcGabT; CjFlaB and EcYbaN; CjFlaB and EcYcdG; CjFlaB and EcYhgN; CjFlaB and EcYedK; CjFlaB and EcYidX; CjFlaB and LaFrc; CjFlaB and LaEno; CjFlaB and LjEFTu; CjFlaB and BfOmpA; CjFlaB and PrOmpA; CjFlaB and Cp10bA; CjFlaB and CpSpA; CjFlaB and EfSant; CjFlaB and LmOsp; EcOFliC and CjGT-A; EcOFliC and Cjdmh; EcOFliC and CjCgtA; EcOFliC and SeFljB; EcOFliC and EcEra; EcOFliC and EcFocA; EcOFliC and EcFrvX; EcOFliC and EcGabT; EcOFliC and EcYbaN; EcOFliC and EcYcdG; EcOFliC and EcYhgN; EcOFliC and EcYedK; EcOFliC and EcYidX; EcOFliC and LaFrc; EcOFliC and LaEno; EcOFliC and LjEFTu; EcOFliC and BfOmpA; EcOFliC and PrOmpA; EcOFliC and Cp10bA; EcOFliC and CpSpA; EcOFliC and EfSant; EcOFliC and LmOsp; CjGT-A and Cjdmh; CjGT-A and CjCgtA; CjGT-A and SeFljB; CjGT-A and EcEra; CjGT-A and EcFocA; CjGT-A and EcFrvX; CjGT-A and EcGabT; CjGT-A and EcYbaN; CjGT-A and EcYcdG; CjGT-A and EcYhgN; CjGT-A and EcYedK; CjGT-A and EcYidX; CjGT-A and LaFrc; CjGT-A and LaEno; CjGT-A and LjEFTu; CjGT-A and BfOmpA; CjGT-A and PrOmpA; CjGT-A and Cp10bA; CjGT-A and CpSpA; CjGT-A and EfSant; CjGT-A and LmOsp; Cjdmh and CjCgtA; SeFljB; Cjdmh and EcEra; Cjdmh and EcFocA; Cjdmh and EcFrvX; Cjdmh and EcGabT; Cjdmh and EcYbaN; Cjdmh and EcYcdG; Cjdmh and EcYhgN; Cjdmh and EcYedK; EcYidX; Cjdmh and LaFrc; Cjdmh and LaEno; Cjdmh and LjEFTu; Cjdmh and BfOmpA; Cjdmh and PrOmpA; Cjdmh and Cp10bA; Cjdmh and CpSpA; Cjdmh and EfSant; Cjdmh and LmOsp; CjCgtA and SeFljB; CjCgtA and EcEra; CjCgtA and EcFocA; CjCgtA and EcFrvX; CjCgtA and EcGabT; CjCgtA and EcYbaN; CjCgtA and EcYcdG; CjCgtA and EcYhgN; CjCgtA and EcYedK; CjCgtA and EcYidX; CjCgtA and LaFrc; CjCgtA and LaEno; CjCgtA and LjEFTu; CjCgtA and BfOmpA; CjCgtA and PrOmpA; CjCgtA and Cp10bA; CjCgtA and CpSpA; CjCgtA and EfSant; CjCgtA and LmOsp; SeFljB and EcEra; SeFljB and EcFocA; SeFljB and EcFrvX; SeFljB and EcGabT; SeFljB and EcYbaN; SeFljB and EcYcdG; SeFljB and EcYhgN; SeFljB and EcYedK; SeFljB and EcYidX; SeFljB and LaFrc; SeFljB and LaEno; SeFljB and LjEFTu; SeFljB and BfOmpA; SeFljB and PrOmpA; SeFljB and Cp10bA; SeFljB and CpSpA; SeFljB and EfSant; SeFljB and LmOsp; EcEra and EcFocA; EcEra and EcFrvX; EcEra and EcGabT; EcEra and EcYbaN; EcEra and EcYcdG; EcEra and EcYhgN; EcEra and EcYedK; EcEra and EcYidX; EcEra and LaFrc; EcEra and LaEno; EcEra and LjEFTu; EcEra and BfOmpA; EcEra and PrOmpA; EcEra and Cp10bA; EcEra and CpSpA; EcEra and EfSant; EcEra and LmOsp; EcFocA and EcFrvX; EcFocA and EcGabT; EcFocA and EcYbaN; EcFocA and EcYcdG; EcFocA and EcYhgN; EcFocA and EcYedK; EcFocA and EcYidX; EcFocA and LaFrc; EcFocA and LaEno; EcFocA and LjEFTu; EcFocA and BfOmpA; EcFocA and PrOmpA; EcFocA and Cp10bA; EcFocA and CpSpA; EcFocA and EfSant; EcFocA and LmOsp; EcFrvX and EcGabT; EcFrvX and EcYbaN; EcFrvX and EcYcdG; EcFrvX and EcYhgN; EcFrvX and EcYedK; EcFrvX and EcYidX; EcFrvX and LaFrc; EcFrvX and LaEno; EcFrvX and LjEFTu; EcFrvX and BfOmpA; EcFrvX and PrOmpA; EcFrvX and Cp10bA; EcFrvX and CpSpA; EcFrvX and EfSant; EcFrvX and LmOsp; EcGabT and EcYbaN; EcGabT and EcYcdG; EcGabT and EcYhgN; EcGabT and EcYedK; EcGabT and EcYidX; EcGabT and LaFrc; EcGabT and LaEno; EcGabT and LjEFTu; EcGabT and BfOmpA; EcGabT and PrOmpA; EcGabT and Cp10bA; EcGabT and CpSpA; EcGabT and EfSant; EcGabT and LmOsp; EcYbaN and EcYcdG; EcYbaN and EcYhgN; EcYbaN and EcYedK; EcYbaN and EcYidX; EcYbaN and LaFrc; EcYbaN and LaEno; EcYbaN and LjEFTu; EcYbaN and BfOmpA; EcYbaN and PrOmpA; EcYbaN and Cp10bA; EcYbaN and CpSpA; EcYbaN and EfSant; EcYbaN and LmOsp; EcYcdG and EcYhgN; EcYcdG and EcYedK; EcYcdG and EcYidX; EcYcdG and LaFrc; EcYcdG and LaEno; EcYcdG and LjEFTu; EcYcdG and BfOmpA; EcYcdG and PrOmpA; EcYcdG and Cp10bA; EcYcdG and CpSpA; EcYcdG and EfSant; EcYcdG and LmOsp; EcYhgN and EcYedK; EcYhgN and EcYidX; EcYhgN and LaFrc; EcYhgN and LaEno; EcYhgN and LjEFTu; EcYhgN and BfOmpA; EcYhgN and PrOmpA; EcYhgN and Cp10bA; EcYhgN and CpSpA; EcYhgN and EfSant; EcYhgN and LmOsp; EcYedK and EcYidX; EcYedK and LaFrc; EcYedK and LaEno; EcYedK and LjEFTu; EcYedK and BfOmpA; EcYedK and PrOmpA; EcYedK and Cp10bA; EcYedK and CpSpA; EcYedK and EfSant; EcYedK and LmOsp; EcYidX and LaFrc; EcYidX and LaEno; EcYidX and LjEFTu; EcYidX and BfOmpA; EcYidX and PrOmpA; EcYidX and Cp10bA; EcYidX and CpSpA; EcYidX and EfSant; EcYidX and LmOsp; LaFrc and LaEno; LaFrc and LjEFTu; LaFrc and BfOmpA; LaFrc and PrOmpA; LaFrc and Cp10bA; LaFrc and CpSpA; LaFrc and EfSant; LaFrc and LmOsp; LaEno and LjEFTu; LaEno and BfOmpA; LaEno and PrOmpA; LaEno and Cp10bA; LaEno and CpSpA; LaEno and EfSant; LaEno and LmOsp; LjEFTu and BfOmpA; LjEFTu and PrOmpA; LjEFTu and Cp10bA; LjEFTu and CpSpA; LjEFTu and EfSant; LjEFTu and LmOsp; BfOmpA and PrOmpA; Cp10bA; CpSpA; EfSant; LmOsp; PrOmpA and Cp10bA; PrOmpA and CpSpA; PrOmpA and EfSant; PrOmpA and LmOsp; Cp10bA and CpSpA; Cp10bA and EfSant; Cp10bA and LmOsp; CpSpA and EfSant; CpSpA and LmOsp; and EfSant and LmOsp.

In some embodiments, the methods for aiding in the diagnosis of irritable bowel syndrome (IBS) in a subject comprise determining the level of three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, or all twenty-seven bacterial antigen antibody markers, wherein the bacterial antigen antibody marker is selected from the group consisting of antibodies against EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant and LmOsp.

In some embodiments, the method comprises:
a) contacting a biological sample from the subject with a bacterial antigen antibody-binding moiety (e.g., a bacterial antigen on a multiwell plate) under conditions suitable to transform the bacterial antigen antibody present in the sample into a complex comprising the bacterial antigen antibody and the bacterial antigen antibody-binding moiety; and b) determining the level of the complex, thereby determining the level of the bacterial antigen antibody present in the sample.

In some embodiments, the method further comprises c) comparing the level of the bacterial antigen antibody present in the sample to a control level of the bacterial antigen antibody, wherein the level of the bacterial antigen antibody is indicative of an increased likelihood of the subject having IBS.

In some embodiments, the control level of the bacterial antigen antibody is the level of the bacterial antigen antibody in a sample from a healthy control subject or an average level of the bacterial antigen antibody present in a sample from a cohort of healthy control subjects. In other embodiments, the control level of the bacterial antigen antibody is the level of the bacterial antigen antibody in a sample from a non-IBS subject or an average level of the bacterial antigen antibody present in a sample from a cohort of non-IBS subjects. Non-limiting examples of diseased subjects that are useful for determining a control level from include subjects with a non-IBS gastrointestinal disease, subjects with inflammatory bowel disease (IBD), subjects with ulcerative colitis (UC), subjects with Crohn's disease (CD), subjects with celiac disease, subjects with gastroesophageal reflux disease (GERD), subjects with cancer, subjects with a cancer of the gastrointestinal tract, subjects with a cancer of the stomach, subjects with a cancer of the small or large bowel, and the like.

In some embodiments, the control level is measured by contacting a biological sample from a healthy control subject with a bacterial antigen (e.g., on a multiwall plate) under conditions suitable to transform the bacterial antigen antibody present in the individual sample into a complex comprising the bacterial antigen antibody and the bacterial antigen; and (b) determining the level of the complex, thereby determining the level of the bacterial antigen antibody present in the individual sample. In other instances, the control level is the average level of the complex as measured from samples of a cohort of healthy control subjects.

In some embodiments, a similar level of bacterial antigen antibody in a sample from a subject, relative to control level, is indicative of an increased likelihood of the subject not having IBS. In some embodiments, a difference in the level of bacterial antigen antibody in a sample from a subject, relative to control level, is indicative of an increased likelihood of the subject having IBS.

In more preferred embodiments, the method further comprises detection of at least one mast cell marker selected from β-tryptase, histamine, prostaglandin $E_2$ (PGE2), and a combination thereof. Methods for detecting β-tryptase, histamine and prostaglandin $E_2$ (PGE2) are described in detail in U.S. Pat. No. 8,114,616 and U.S. Patent Application Publication No. 2012/244558, the disclosures of which are herein incorporated by reference in their entirety for all purposes.

In some embodiments, the method for aiding in the diagnosis of IBS in a subject comprises determining the level of at least one mast cell marker, wherein the mast cell marker is selected from the group consisting of β-tryptase, histamine, prostaglandin E2, and combinations thereof. In other embodiments, the method for aiding in the diagnosis of IBS in a subject comprise determining the level of at least two mast cell markers, wherein the mast cell marker is selected from the group consisting of β-tryptase, histamine, prostaglandin E2, and combinations thereof. For instance, the method includes measuring the level of at least two mast cell markers, e.g., β-tryptase and histamine, β-tryptase and prostaglandin E2, and β-tryptase and prostaglandin E2. In yet other embodiments, the method for aiding in the diagnosis of IBS in a subject comprise determining the level of all three mast cell markers as described herein.

In certain embodiments, the methods are provided for aiding in the diagnosis of irritable bowel syndrome in a subject by determining the level of at least one bacterial antigen antibody marker, wherein the bacterial antigen antibody complexes with a bacterial antigen selected from the group consisting of EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and combinations thereof, in conjunction with at least one mast cell marker selected from β-tryptase, histamine, prostaglandin E2 (PGE2), and a combination thereof.

In some embodiments, the method for predicting a diagnosis of IBS in a subject comprise determining the level of at least 1, 2, 3, 4, 5, 6, 7, 8, 9, 10, 11, 12, 13, 14, 15, 16, 17, 18, 19, 20, 21, 22, 23, 24, 25, 26 or 27 bacterial antigen antibody marker(s), wherein the bacterial antigen antibody marker is selected from the group consisting of antibodies against EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant and LmOsp, and at least 1, 2, 3 mast cell marker(s), wherein the mast cell marker is selected from the group consisting of β-tryptase, histamine, prostaglandin E2, and combinations thereof. In some instances, the method includes determining the level of a combination of bacterial antigen antibody marker: mast cell marker, e.g., 1:1 (i.e., EcFliC: β-tryptase), 1:2, 1:3, 2:1, 2:2, 2:3, 3:1, 3:2, 3:3, 4:1, 4:2, 4:3, 5:1, 5:2, 5:3, 6:1, 6:2, 6:3, 7:1, 7:2, 7:3, 8:1, 8:2, 8:3, 9:1, 9:2, 9:3, 10:1, 10:2, 10:3, 11:1, 11:2, 11:3, 12:0, 12:1, 12:2, 12:3, 13:0, 13:1, 13:2, 13:3, 14:1, 14:2, 14:3, 15:1, 15:2, 15:3, 6:1, 16:2, 16:3, 17:1, 17:2, 17:3, 18:1, 18:2, 18:3, 19:1, 19:2, 19:3, 20:1, 20:2, 20:3, 21:1, 21:2, 21:3, 22:1, 22:2, 22:3, 23:1, 23:2, 23:3, 24:1, 24:2, 24:3, 25:1, 25:2, 25:3, 26:1, 26:2, 26:3, 27:1, 27:2, and 27:3 bacterial antigen antibody marker: mast cell marker, respectively.

In another aspect, the invention provides a method of classifying a diagnosis of IBS as IBS-constipation (IBS-C), IBS diarrhea (IBS-D), IBS-mixed (IBS-M), IBS-unsubtyped (IBS-U), IBS-alternating (IBS-A), or post-infectious IBS (IBS-PI).

In some embodiments, the method for aiding in the diagnosis of IBS in a subject comprises determining the level of at least one stress factor marker, wherein the stress factor marker is selected from the group consisting of cortisol, BDNF, serotonin, CRF, ACTH, and combinations thereof. In other embodiments, the method for aiding in the diagnosis of IBS in a subject comprise determining the level of at least two stress factor markers, wherein the stress factor marker is selected from the group consisting of cortisol, BDNF, serotonin, CRF, ACTH, and combinations thereof. For instance, the level of two tress factor markers, such as, cortisol and BDNF, cortisol and serotonin, cortisol and CRF, cortisol and ACTH, BDNF and serotonin, BDNF and CRF, BDNF and ACTH, serotonin and CRF, serotonin and ACTH, and CRF and ACTH, is determined. In yet other embodiments, the method for aiding in the diagnosis of IBS in a subject comprise determining the level of at least three, four or all five stress factor markers, wherein the stress factor marker is selected from the group consisting of cortisol, BDNF, serotonin, CRF, ACTH, and combinations thereof.

In some embodiments, the method for predicting a diagnosis of IBS in a subject comprise determining the level of at least 1, 2, 3, 4, 5, 6, 7, 8, 9, 10, 11, 12, 13, 14, 15, 16, 17, 18, 19, 20, 21, 22, 23, 24, 25, 26 or 27 bacterial antigen antibody marker(s), wherein the bacterial antigen antibody marker is selected from the group consisting of antibodies against EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant and LmOsp, and at least 1, 2, 3 mast cell marker(s), wherein the mast cell marker is selected from the group consisting of β-tryptase, histamine, prostaglandin E2, and combinations thereof. In some instances, the method includes determining the level of a combination of bacterial antigen antibody marker: mast cell marker, e.g., 1:1 (i.e., EcFliC: β-tryptase), 1:2, 1:3, 2:1, 2:2, 2:3, 3:1, 3:2, 3:3, 4:1, 4:2, 4:3, 5:1, 5:2, 5:3, 6:1, 6:2, 6:3, 7:1, 7:2, 7:3, 8:1, 8:2, 8:3, 9:1, 9:2, 9:3, 10:1, 10:2, 10:3, 11:1, 11:2, 11:3, 12:0, 12:1, 12:2, 12:3, 13:0, 13:1, 13:2, 13:3, 14:1, 14:2, 14:3, 15:1, 15:2, 15:3, 6:1, 16:2, 16:3, 17:1, 17:2, 17:3, 18:1, 18:2, 18:3, 19:1, 19:2, 19:3, 20:1, 20:2, 20:3, 21:1, 21:2, 21:3, 22:1, 22:2, 22:3, 23:1, 23:2, 23:3, 24:1, 24:2, 24:3, 25:1, 25:2, 25:3, 26:1, 26:2, 26:3, 27:1, 27:2, and 27:3 bacterial antigen antibody marker: mast cell marker, respectively.

In other embodiments, the method for predicting a diagnosis of IBS in a subject comprise determining the level of at least 1, 2, 3, 4, 5, 6, 7, 8, 9, 10, 11, 12, 13, 14, 15, 16, 17, 18, 19, 20, 21, 22, 23, 24, 25, 26 or 27 bacterial antigen antibody marker(s) as described herein, at least 1, 2, 3 mast cell marker(s) as described herein, and optionally, at least 1, 2, 3, 4, or 5 stress factor marker(s) as described herein. For instance, the method includes determining the level of a combination of bacterial antigen antibody marker: mast cell marker: stress cell marker, e.g., 1:1:1 (i.e., EcFliC: β-tryptase:cortisol), 1:1:2, 1:1:3, 1:1:4, 1:1:5, 1:2:1, 1:2:2, 1:2:3, 1:2:4, 1:2:5, 1:3:1, 1:3:2, 1:3:3, 1:3:4, 1:3:5, 2:1:1, 2:1:2, 2:1:3, 2:1:4, 2:1:5, 2:2:1, 2:2:2, 2:2:3, 2:2:4, 2:2:5, 2:3:1, 2:3:2, 2:3:3, 2:3:4, 2:3:5, 3:1:1, 3:1:2, 3:1:3, 3:1:4, 3:1:5, 3:2:1, 3:2:2, 3:2:3, 3:2:4, 3:2:5, 3:3:1, 3:3:2, 3:3:3, 3:3:4, 3:3:5, 4:1:1, 4:1:2, 4:1:3, 4:1:4, 4:1:5, 4:2:1, 4:2:2, 4:2:3, 4:2:4, 4:2:5, 4:3:1, 4:3:2, 4:3:3, 4:3:4, 4:3:5, 5:1:1, 5:1:2, 5:1:3, 5:1:4, 5:1:5, 5:2:1, 5:2:2, 5:2:3, 5:2:4, 5:2:5, 5:3:1, 5:3:2, 5:3:3, 5:3:4, 5:3:5, 6:1:1, 6:1:2, 6:1:3, 6:1:4, 6:1:5, 6:2:1, 6:2:2, 6:2:3, 6:2:4, 6:2:5, 6:3:1, 6:3:2, 6:3:3, 6:3:4, 6:3:5, 7:1:1, 7:1:2, 7:1:3, 7:1:4, 7:1:5, 7:2:1, 7:2:2, 7:2:3, 7:2:4, 7:2:5, 7:3:1, 7:3:2, 7:3:3, 7:3:4, 7:3:5, 8:1:1, 8:1:2, 8:1:3, 8:1:4, 8:1:5, 8:2:1, 8:2:2, 8:2:3, 8:2:4, 8:2:5, 8:3:1, 8:3:2, 8:3:3, 8:3:4, 8:3:5, 9:1:1, 9:1:2, 9:1:3, 9:1:4, 9:1:5, 9:2:1, 9:2:2, 9:2:3, 9:2:4, 9:2:5, 9:3:1, 9:3:2, 9:3:3, 9:3:4, 9:3:5, 10:1:1, 10:1:2, 10:1:3, 10:1:4, 10:1:5, 10:2:1, 10:2:2, 10:2:3, 10:2:4, 10:2:5, 10:3:1, 10:3:2, 10:3:3, 10:3:4, 10:3:5, 11:1:1, 11:1:2, 11:1:3, 11:1:4, 11:1:5, 11:2:1, 11:2:2, 11:2:3, 11:2:4, 11:2:5, 11:3:1, 11:3:2, 11:3:3, 11:3:4, 11:3:5, 12:1:1, 12:1:2, 12:1:3, 12:1:4, 12:1:5, 12:2:1, 12:2:2, 12:2:3, 12:2:4, 12:2:5, 12:3:1, 12:3:2, 12:3:3, 12:3:4, 12:3:5, 13:1:1, 13:1:2, 13:1:3, 13:1:4, 13:1:5, 13:2:1, 13:2:2, 13:2:3, 13:2:4, 13:2:5, 13:3:1, 13:3:2, 13:3:3, 13:3:4, 13:3:5, 15:1:1, 15:1:2, 15:1:3, 15:1:4, 15:1:5, 15:2:1, 15:2:2, 15:2:3, 15:2:4, 15:2:5, 15:3:1, 15:3:2, 15:3:3, 15:3:4, 15:3:5, 16:1:1, 16:1:2, 16:1:3, 16:1:4, 16:1:5, 16:2:1, 16:2:2, 16:2:3, 16:2:4, 16:2:5, 16:3:1, 16:3:2, 16:3:3, 16:3:4, 16:3:5, 17:1:1, 17:1:2, 17:1:3, 17:1:4, 17:1:5, 17:2:1, 17:2:2, 17:2:3, 17:2:4, 17:2:5, 17:3:1, 17:3:2, 17:3:4, 17:3:5, 18:1:1, 18:1:2, 18:1:3, 18:1:4, 18:1:5, 18:2:1, 18:2:2, 18:2:3, 18:2:4, 18:2:5, 18:3:1, 18:3:2, 18:3:3, 18:3:4, 18:3:5, 19:1:1, 19:1:2, 19:1:3, 19:1:4, 19:1:5, 19:2:1, 19:2:2, 19:2:3, 19:2:4, 19:2:5, 19:3:1, 19:3:2, 19:3:3, 19:3:4, 19:3:5, 20:1:1, 20:1:2, 20:1:3, 20:1:4, 20:1:5, 20:2:1, 20:2:2, 20:2:3, 20:2:4, 20:2:5, 20:3:1, 20:3:2, 20:3:3, 20:3:4, 20:3:5, 21:1:1, 21:1:2, 21:1:3, 21:1:4, 21:1:5, 21:2:1, 21:2:2, 21:2:3, 21:2:4, 21:2:5, 21:3:1, 21:3:2, 21:3:3, 21:3:4, 21:3:5, 22:1:1, 22:1:2, 22:1:3, 22:1:4, 22:1:5, 22:2:1, 22:2:2, 22:2:3, 22:2:4, 22:2:5, 22:3:1, 22:3:2, 22:3:3, 22:3:4, 22:3:5, 23:1:1, 23:1:2, 23:1:3, 23:1:4, 23:1:5, 23:2:1, 23:2:2, 23:2:3, 23:2:4, 23:2:5, 23:3:1, 23:3:2, 23:3:3, 23:3:4, 23:3:5, 24:1:1, 24:1:2, 24:1:3, 24:1:4, 24:1:5, 24:2:1, 24:2:2, 24:2:3, 24:2:4, 24:2:5, 24:3:1, 24:3:2, 24:3:3, 24:3:4, 24:3:5, 25:1:1, 25:1:2, 25:1:3, 25:1:4, 25:1:5, 25:2:1, 25:2:2, 25:2:3, 25:2:4, 25:2:5, 25:3:1, 25:3:2, 25:3:3, 25:3:4, 25:3:5, 26:1:1, 26:1:2, 26:1:3, 26:1:4, 26:1:5, 26:2:1, 26:2:2, 26:2:3, 26:2:4, 26:2:5, 26:3:1, 26:3:2, 26:3:3, 26:3:4, 26:3:5, 27:1:1, 27:1:2, 27:1:3, 27:1:4, 27:1:5, 27:2:1, 27:2:2, 27:2:3, 27:2:4, 27:2:5, 27:3:1, 27:3:2, 27:3:3, 27:3:4, and 27:3:5 bacterial antigen antibody marker: mast cell marker: stress cell marker, respectively.

In another aspect, the present invention provides methods for monitoring the progression or regression of irritable bowel syndrome in a subject by a) determining the level of 1, 2, 3, 4, 5, 6, 7, 8, 9, 10, 11, 12, 13, 14, 15, 16, 17, 18, 19, 20, 21, 22, 23, 24, 25, 26, 27 or more bacterial antigen antibody markers, wherein the bacterial antigen antibody recognizes a bacterial antigen selected from the group consisting of EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and combinations thereof in a first biological sample taken at a first time; b) determining the level of the bacterial antigen antibody marker in a second biological sample taken at a second time; and c) comparing the level of the bacterial antigen antibody marker present in the first sample to the level of the bacterial antigen antibody present in the second sample, wherein the difference in the level of the bacterial antigen antibody marker is indicative of the progression of IBS in the subject.

In some embodiments, the methods for monitoring the progression or regression of irritable bowel syndrome in a subject comprise: a) determining the level of at least one bacterial antigen antibody marker, wherein the antibody marker complexes with a bacterial antigen selected from the group consisting of EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and combinations thereof, in conjunction with at least one mast cell marker selected from β-tryptase, histamine, prostaglandin $E_2$ (PGE2) and a combination thereof in a first sample at a first time point, b) determining the levels of the bacterial antigen antibody marker(s) and the mast cell marker(s) in a second sample at a second time point; and c) comparing the levels of the bacterial antigen antibody marker(s) and the mast cell marker(s), wherein the levels in the first sample compared to the second sample are indicative of progression or regression of IBS in the subject.

In some embodiments, an increase in the level(s) of the bacterial antigen antibody marker(s) and the mast cell marker(s) in the first sample compared to the second sample is indicative of the progression of IBS in the subject. In some embodiments, a decrease in the level(s) of the bacterial antigen antibody marker(s) and the mast cell marker(s) in the first sample compared to the second sample is indicative of regression of IBS in the subject.

In some embodiments, the present invention provides methods for classifying a diagnosis of IBS in a subject, the method comprising:

a) measuring the levels of an array of bacterial antigen antibody markers that recognize a bacterial antigen (e.g., EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, NOmpA, PrOmpA, Cp10bA, CpSpA, EfSant, LmOsp, and the like) and an array of mast cell markers e.g., serum β-tryptase, prostaglandin E2, and the like) in a biological sample taken from the subject;

b) applying a statistical analysis to the measured levels of the selected bacterial antigen antibody markers and mast cell markers to generate a disease classification profile, wherein the disease classification profile comprises a representation of the level of the selected bacterial antigen antibody markers and mast cell markers; and c) comparing the disease classification profile of the subject to that of a control to determine whether the subject has IBS-constipation (IBS-C), IBS diarrhea (IBS-D), IBS-mixed (IBS-M), IBS-alternating (IBS-A), or post-infectious IBS (IBS-PI).

In some embodiments, the disease classification profile includes an empirically derived profile that is based upon an analysis of a plurality of selected bacterial antigen antibody markers and mast cell markers. In one aspect, the concentration of markers or their measured concentration values are transformed into a profile by an algorithm resident on a computer. In certain aspects, the profile is a synthetic or human derived output, score, or cut off value(s), which expresses the biological data in numerical terms. The profile can be used to determine or make or aid in making a clinical decision such as a disease classification of IBS subtypes. A disease classification profile can be measured multiple times over the course of time. In one aspect, the algorithm can be trained with known samples and thereafter validated with samples of known identity.

In some embodiments, the disease classification profile control comprises a disease classification profile from a subject who is a healthy subject, a subject with IBS or a subtype of IBS such as IBS-constipation (IBS-C), IBS diarrhea (IBS-D), IBS-mixed (IBS-M), IBS-alternating (IBS-A), or post-infectious IBS (IBS-PI). In other embodiments, the disease classification profile of the control comprises an average of a plurality of disease classification profiles from a plurality of subjects who represent either healthy controls, subjects with IBS or subjects with a specific subtype of IBS such as IBS-C, IBS-D, IBS-M, IBS-A or IBS-PI.

The sample used for detecting or determining the level of at least one bacterial antigen antibody marker is typically whole blood, plasma, serum, saliva, urine, stool (i.e., feces), tears, and any other bodily fluid, or a tissue sample (i.e., biopsy) such as a small intestine or colon sample. Preferably, the sample is serum, whole blood, plasma, stool, urine, or a tissue biopsy. In certain instances, the methods of the present invention further comprise obtaining the sample from the individual prior to detecting or determining the level of at least one bacterial antigen antibody in the sample. In a preferred embodiment, the additional bacterial antigen antibody and/or mast cell markers is detected from a blood or serum sample. In other embodiments, the additional bacterial antigen and/or mast cell marker is detected from a stool sample or a biopsy from the bowel of the subject.

In certain other embodiments, the level of at least one bacterial antigen antibody marker is determined using an immunoassay (e.g., ELISA) or an immunohistochemical assay. A non-limiting example of an immunoassay suitable for use in the methods of the present invention includes an enzyme-linked immunosorbent assay (ELISA). Examples of immunohistochemical assays suitable for use in the methods of the present invention include, but are not limited to, immunofluorescence assays such as direct fluorescent antibody assays, indirect fluorescent antibody (IFA) assays, anticomplement immunofluorescence assays, and avidin-biotin immunofluorescence assays. Other types of immunohistochemical assays include immunoperoxidase assays. Suitable ELISA kits for determining the presence of level of a bacterial antigen in a serum, plasma, saliva, or urine sample, are available from e.g., Antigenix America Inc. (Huntington station, NY), Promega (Madison, Wis.), R&D Systems, Inc. (Minneapolis, Minn.), Life Technologies (Carlsbad, Calif.), CHEMICON International, Inc. (Temecula, Calif.), Neogen Corp. (Lexington, Ky.), PeproTech (Rocky Hill, N.J.), Alpco Diagnostics (Salem, N.H.), Pierce Biotechnology, Inc. (Rockford, Ill.), and/or Abazyme (Needham, Mass.).

1. Bacterial Antigen Antibodies

As used herein, the term "bacterial antigen antibody" refers to an antibody that specifically binds to a bacterial antigen or an antigenic fragment thereof, such as an anti-bacterial antigen antibody. Without being bound to any particular theory, individuals with IBS or other disorders involving the gastrointestinal microbiota can develop anti-bacterial antigen antibodies.

In one aspect, the present invention provides methods for aiding in the diagnosis of IBS using bacterial antigen antibody markers.

In some embodiments, the method comprises measuring the level of an array of bacterial antigen antibody markers in a biological sample taken from the subject. In some embodiments, the level of at least one bacterial antigen antibody marker is increased in an individual with IBS compared to a healthy control. In other embodiments, the level of at least one bacterial antigen antibody marker is decreased in an individual with IBS compared to a healthy control. In some embodiments, the level of an array of bacterial antigen antibody markers is dysregulated in a sample taken from an individual with IBS compared to one from a healthy control.

In some embodiments, the method comprises:

a) contacting a biological sample from the subject with a bacterial antigen polypeptide or an antigenic fragment thereof under conditions suitable to transform the bacterial antigen antibody present in the sample into a complex comprising the bacterial antigen antibody and the bacterial antigen polypeptide or fragment thereof; and b) determining the level of the complex, thereby determining the level of the bacterial antigen present in the sample. In some embodiments, the method further comprises:

c) comparing the level of the bacterial antigen antibody present in the sample to a control level of the bacterial antigen antibody, wherein the level of the bacterial antigen antibody is indicative of an increased likelihood of the subject having IBS.

The bacterial antigen polypeptide or fragment thereof selectively binds to the bacterial antigen antibody to be measured. For example, the level of an antibody against bacteria flagellin (e.g., SfFliC) can be measured using the flagellin polypeptide or an antigenic fragment thereof.

In a specific embodiment, the invention provides a method to aid in the diagnosis of IBS, the method comprises:
- a) contacting a sample having a bacterial antigen antibody contained therein under conditions suitable to transform the bacterial antigen antibody into a complex comprising the bacterial antigen and the captured antibacterial antigen antibody;
- b) contacting the complex with an enzyme labeled indicator antibody to transform the complex into a labeled complex;
- c) contacting the labeled complex with a substrate for the enzyme; and
- d) detecting the presence or level of the bacterial antigen antibody in the sample.

For example, as illustrated in Examples 3 and 4 described herein, methods of the present invention are used to measure the levels of bacterial antigen antibodies present in a sample.

In certain embodiments, a variety of bacterial antigens are particularly useful in the methods of the present invention for aiding in the diagnosis of IBS. Non-limiting examples of bacterial antigens include flagellin polypeptides or fragments thereof, and other polypeptides or fragments thereof that are expressed by the gastrointestinal microbiota. Microbial flagellin is a protein found in bacterial flagellum that arrange itself in a hollow cylinder to form the filament. Flagellin polypeptides or fragments thereof are typically expressed by bacteria including *Clostridium, Lachnospiraceae* bacterium A4, *E. coli* K12, *E. coli* O157:H7, *Shigella flexneri, Campylobacter jejuni*, and *Salmonella enteritidis*. Non-limiting examples of flagellin polypeptides are presented in Table 1.

preferably greater than about 80%, 85%, 90%, 95%, 96%, 97%, 98%, or 99% amino acid sequence identity with a FlaA protein, with the amino acid identity determined using a sequence alignment program such as CLUSTALW. Such antigens can be prepared, for example, by purification from enteric bacteria such as *Campylobacter jejuni*, by recombinant expression of a nucleic acid encoding a FlaA peptide such as NCBI Accession No. ABC69276.1, by synthetic means such as solution or solid phase peptide synthesis.

The term "CjFlaB" refers to a flagellin B of the *Campylobacter jejuni* that is immunoreactive with an anti-FlaB antibody. Suitable CjFlaB antigens useful in determining anti-FlaB antibody levels in a sample include, without limitation, a FlaB protein, a FlaB polypeptide having substantially the same amino acid sequence as the FlaB protein, or a fragment thereof such as an immunoreactive fragment thereof. A FlaB polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a FlaB protein, with the amino acid identity determined using a sequence alignment program such as CLUSTALW. Such antigens can be prepared, for example, by purification from enteric bacteria such as *Campylobacter jejuni*, by recombinant expression of a nucleic acid encoding a FlaB peptide such as NCBI Accession EAQ72883.1, by synthetic means such as solution or solid phase peptide synthesis.

The term "EcFliC" refers to a flagellin of *Escherichia coli* strain K12 that is immunoreactive with an anti-FliC anti-

TABLE 1

Flagellin and Other Polypeptides (Bacterial Antigens)

| Name | Orig. name | Strain | NCBI GenBank Accession No. | Protein Function |
|---|---|---|---|---|
| CBir1 | CBir1 | Unknown, most similar to *Clostridium* subphylum | AAT06254 | flagellin |
| FlaX | FlaX | Unknown, most similar to *Clostridium* subphylum | AAT06255 | flagellin |
| Fla2 | Fla2 | Lachnospiraceae bacterium A4 | ABI48283 | flagellin |
| EcFliC | FliC | *Escherichia coli* K12 | AAA23950.1 | flagellin |
| SfFliC | FliC | *Shigella flexneri* | BAA04093.1 | flagellin |
| CjFlaA | FlaA | *Campylobacter jejuni* | ABC69276.1 | flagellin |
| CjFlaB | FlaB | *Campylobacter jejuni* | EAQ72883.1 | flagellin |
| EcOFliC | FliC | *Escherichia coli* O157:H7 | BAB36085.1 | flagellin |
| SeFljB | FljB | *Salmonella enteritidis* | AAC43354.1 | flagellin |
| CjGT-A | Cj81-045 | *Campylobacter jejuni* | AAW56124.1 | glycosyltransferase |
| Cjdmh | Cj81-128 | *Campylobacter jejuni* | AAW56187.1 | mannose-heptose |
| CjCgtA | Cj81-008 | *Campylobacter jejuni* | AAW56101.1 | acetylgalactosaminyltransferase |

The term "CjFlaA" refers to a flagellin subunit of the *Campylobacter jejuni* that is immunoreactive with an anti-FlaA antibody. Suitable CjFlaA antigens useful in determining anti-FlaA antibody levels in a sample include, without limitation, a FlaA protein, a FlaA polypeptide having substantially the same amino acid sequence as the FlaA protein, or a fragment thereof such as an immunoreactive fragment thereof. A FlaA polypeptide generally describes polypeptides having an amino acid sequence with greater than about 50% identity, preferably greater than about 60% identity, more preferably greater than about 70% identity, still more body. Suitable EcFliC antigens useful in determining anti-FliC antibody levels in a sample include, without limitation, a FliC protein of *Escherichia coli* strain K12, a FliC polypeptide having substantially the same amino acid sequence as the FliC protein of *Escherichia coli* strain K12, or a fragment thereof such as an immunoreactive fragment thereof. A FliC polypeptide of *Escherichia coli* strain K12 generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a FliC protein of *Escherichia coli* strain K12, with the amino acid identity determined using a sequence alignment program such as CLUSTALW. Such antigens can be prepared, for example, by purification from enteric bacteria such as *E. coli*, by recombinant expression of a nucleic acid encoding a FliC peptide such as NCBI Accession No. AAA23950.1, by synthetic means such as solution or solid phase peptide synthesis.

The term "EcOFliC" refers to a flagellin of *Escherichia coli* strain O157:H7 that is immunoreactive with an anti-FliC antibody. Suitable FliC antigens useful in determining anti-FliC antibody levels in a sample include, without limitation, a FliC protein, a FliC polypeptide having substantially the same amino acid sequence as the FliC protein, or a fragment thereof such as an immunoreactive fragment thereof. A FliC polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a FliC protein, with the amino acid identity determined using a sequence alignment program such as CLUSTALW. Such antigens can be prepared, for example, by purification from enteric bacteria such as *E. coli* strain O157:H7, by recombinant expression of a nucleic acid encoding a FliC peptide such as NCBI Accession No. BAB36085.1, by synthetic means such as solution or solid phase peptide synthesis.

The term "SfFliC" refers to a flagellin of *Shigella flexneri* that is immunoreactive with an anti-FliC antibody. Suitable SfFliC antigens useful in determining anti-FliC antibody levels in a sample include, without limitation, a FliC protein, a FliC polypeptide having substantially the same amino acid sequence as the FliC protein, or a fragment thereof such as an immunoreactive fragment thereof. A FliC polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a FliC protein, with the amino acid identity determined using a sequence alignment program such as CLUSTALW. Such antigens can be prepared, for example, by purification from enteric bacteria such as *Shigella flexneri*, by recombinant expression of a nucleic acid encoding a FliC peptide such as NCBI Accession No. BAA04093.1, by synthetic means such as solution or solid phase peptide synthesis. One skilled in the art will appreciate that *Shigella flexneri* FliC is also known as flagellar filament structural protein, flagellin, and H-antigen.

The term "Cj81-045" or "CjGT-A" refers to a *Campylobacter jejuni* membrane protein that is immunoreactive with an anti-Cj81-045 (CjGT-A) antibody. Suitable Cj81-045 (CjGT-A) antigens useful in determining anti-Cj81-045 (–CjGT-A) antibody levels in a sample include, without limitation, a Cj81-045 (CjGT-A) protein, a Cj81-045 (CjGT-A) polypeptide having substantially the same amino acid sequence as the Cj81-045 (CjGT-A) protein, or a fragment thereof such as an immunoreactive fragment thereof. A Cj81-045 (CjGT-A) polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Cj81-045 (CjGT-A) protein, with the amino acid identity determined using a sequence alignment program such as CLUSTALW. Such antigens can be prepared, for example, by purification from enteric bacteria such as *Campylobacter jejuni*, by recombinant expression of a nucleic acid encoding a Cj81-045 (CjGT-A) peptide such as NCBI Accession AAW56124.1, by synthetic means such as solution or solid phase peptide synthesis.

The term "Cj81-128" or "Cjdmh" refers to a *Campylobacter jejuni* membrane protein that is immunoreactive with an anti-Cj81-128 (–Cjdmh) antibody. Suitable Cj81-128 (Cjdmh) antigens useful in determining anti-Cj81-128 (–Cjdmh) antibody levels in a sample include, without limitation, a Cj81-128 (Cjdmh) protein, a Cj81-128 (Cjdmh) polypeptide having substantially the same amino acid sequence as the Cj81-128 (Cjdmh) protein, or a fragment thereof such as an immunoreactive fragment thereof. A Cj81-128 (Cjdmh) polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Cj81-128 (Cjdmh) protein, with the amino acid identity determined using a sequence alignment program such as CLUSTALW. Such antigens can be prepared, for example, by purification from enteric bacteria such as *Campylobacter jejuni*, by recombinant expression of a nucleic acid encoding a Cj81-128 (Cjdmh) peptide such as NCBI Accession AAW56187.1, by synthetic means such as solution or solid phase peptide synthesis.

The term "Cj81-008" or "CjCgtA" refers to a beta-1,4-N-acetylgalactosaminyltransferase of *Campylobacter jejuni* that is immunoreactive with an anti-Cj81-008 (–CjCgtA) antibody. Suitable Cj81-008 (CjCgtA) antigens useful in determining anti-Cj81-008 (–CjCgtA) antibody levels in a sample include, without limitation, a Cj81-008 (CjCgtA) protein, a Cj81-008 (CjCgtA) polypeptide having substantially the same amino acid sequence as the Cj81-008 (CjCgtA) protein, or a fragment thereof such as an immunoreactive fragment thereof. A Cj81-008 (CjCgtA) polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Cj81-008 (CjCgtA) protein, with the amino acid identity determined using a sequence alignment program such as CLUSTALW. Such antigens can be prepared, for example, by purification from enteric bacteria such as *Campylobacter jejuni*, by recombinant expression of a nucleic acid encoding a Cj81-008 (CjCgtA) peptide such as NCBI Accession AAW56101.1, by synthetic means such as solution or solid phase peptide synthesis.

In some embodiments, the method of the present invention includes determining the level of an antibody against at least one polypeptide or fragment thereof expressed by the gastrointestinal microbiota (e.g., *E. coli* K12). Non-limiting examples of polypeptides expressed by *E. coli* of the gastrointestinal microbiota are presented in Table 2.

TABLE 2

E. Coli strain K12 Polypeptides (Bacterial Antigens)

| Name | Original name | Strain | NCBI GenBank Accession No. | Protein function |
|---|---|---|---|---|
| EcEra | Era | Escherichia coli K12 | AAA03242.1 | Ras-like protein GTPase |
| EcFocA | FocA | Escherichia coli K12 | BAA35639.1 | Formate transporter |
| EcFrvX | FrvX | Escherichia coli K12 | AAB03031.1 | Putative aminopeptidase |
| EcGabT | GabT | Escherichia coli K12 | AAC36832.1 | 4-aminobutyrate aminotransferase |
| EcYbaN | YbaN | Escherichia coli K12 | AAB40222.1 | Unknown inner membrane protein |
| EcYcdG | YcdG | Escherichia coli K12 | AAC74091.2 | Unknown |
| EcYhgN | YhgN | Escherichia coli K12 | AAA58232.1 | Unknown; predicted antibiotic transporter |
| EcYedK | YedK | Escherichia coli K12 | AAT48139.1 | Unknown |
| EcYidX | YidX | Escherichia coli K12 | AAT48200.1 | Unknown; predicted lipoproteinC |

The term "EcEra" refers to a Ras-like membrane-associated, ribosome-binding GTPase of the *Escherichia coli* strain K12 that is immunoreactive with an anti-Era antibody. Suitable EcEra antigens useful in determining anti-Era antibody levels in a sample include, without limitation, an Era protein of the *Escherichia coli* strain K12, an Era polypeptide having substantially the same amino acid sequence as the Era protein of the *E. coli* strain K12, or a fragment thereof such as an immunoreactive fragment thereof. An Era polypeptide of the *E. coli* strain K12 generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an Era protein of the *E. coli* strain K12, with the amino acid identity determined using a sequence alignment program such as CLUSTALW. Such antigens can be prepared, for example, by purification from enteric bacteria such as *E. coli* strain K12, by recombinant expression of a nucleic acid encoding an Era peptide such as NCBI Accession No. AAA03242.1, by synthetic means such as solution or solid phase peptide synthesis. One skilled in the art will appreciate that Era is also known as membrane-associated 16S rRNA-binding GTPase, B2566, SdgE and RbaA.

The term "EcFrvX" refers to a fry operon protein of the *Escherichia coli* strain K12 that is immunoreactive with an anti-FrvX antibody. FrvX is predicted to be an endo-1,4-beta-glucanase. Suitable EcFrvX antigens useful in determining anti-FrvX antibody levels in a sample include, without limitation, a FrvX protein of the *E. coli* strain K12, a FrvX polypeptide having substantially the same amino acid sequence as the FrvX protein of the *E. coli* strain K12, or a fragment thereof such as an immunoreactive fragment thereof. A FrvX polypeptide of the *E. coli* train K12 generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a FrvX protein of the *E. coli* strain K12, with the amino acid identity determined using a sequence alignment program such as CLUSTALW. Such antigens can be prepared, for example, by purification from enteric bacteria such as *E. coli*, by recombinant expression of a nucleic acid encoding a FrvX peptide such as NCBI Accession No. AAB03031.1, by synthetic means such as solution or solid phase peptide synthesis.

The term "EcGabT" refers to a PLP-dependent 4-aminobutyrate aminotransferase of the *Escherichia coli* strain K12 that is immunoreactive with an anti-GabT antibody. Suitable EcGabT antigens useful in determining anti-GabT antibody levels in a sample include, without limitation, a GabT protein of the *E. coli* strain K12, a GabT polypeptide having substantially the same amino acid sequence as the GabT protein of the *Escherichia coli* strain K12, or a fragment thereof such as an immunoreactive fragment thereof. A GabT polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a GabT protein of the *E. coli* strain K12, with the amino acid identity determined using a sequence alignment program such as CLUSTALW. Such antigens can be prepared, for example, by purification from enteric bacteria such as *E. coli*, by recombinant expression of a nucleic acid encoding a GabT peptide such as NCBI Accession No. AAC36832.1, by synthetic means such as solution or solid phase peptide synthesis, or by using phage display. One skilled in the art will appreciate that GabT is also known as (S)-3-amino-2-methylpropionate transaminase, GABA aminotransferase, GABA-AT, Gamma-amino-N-butyrate transaminase, and glutamate: succinic semialdehyde transaminase L-AIBAT.

The term "EcYhgN" refers to a *Escherichia coli* strain K12 membrane protein that is predicted to function as an antibiotic transporter and that is immunoreactive with an anti-YhgN antibody. Suitable EcYhgN antigens useful in determining anti-YhgN antibody levels in a sample include, without limitation, a YhgN protein of the *E. coli* strain K12, a YhgN polypeptide having substantially the same amino acid sequence as the YhgN protein of the *E. coli* strain K12, or a fragment thereof such as an immunoreactive fragment thereof. A YhgN polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a YhgN protein of the *E. coli* strain K12, with the amino acid identity determined using a sequence alignment program such as CLUSTALW. Such antigens can be prepared, for example, by purification from enteric bacteria such as *E. coli*, by recombinant expression of a nucleic acid encoding a YhgN peptide such as NCBI Accession No. AAA58232.1, by synthetic means such as solution or solid phase peptide synthesis, or by using phage display. One skilled in the art will appreciate that YhgN is also known as predicted antibiotic transporter.

The term "EcYedK" refers to a *Escherichia coli* strain K12 predicted protein that is that is immunoreactive with an anti-YedK antibody. Suitable EcYedK antigens useful in determining anti-YedK antibody levels in a sample include, without limitation, a YedK protein of the *E. coli* strain K12, a YedK polypeptide having substantially the same amino acid sequence as the YedK protein of the *E. coli* strain K12, or a fragment thereof such as an immunoreactive fragment thereof. A YedK polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a YedK protein of the *E. coli* strain K12, with the amino acid identity determined using a sequence alignment program such as CLUSTALW. Such antigens can be prepared, for example, by purification from enteric bacteria such as *E. coli*, by recombinant expression of a nucleic acid encoding a YedK peptide such as NCBI Accession No. AA48139, by synthetic means such as solution or solid phase peptide synthesis, or by using phage display.

The term "EcYidX" refers to a putative replicase of the *Escherichia coli* strain K12 that is immunoreactive with an anti-YidX antibody. YidX is predicted to be a lipoprotein C. Suitable YidX antigens useful in determining anti-YidX antibody levels in a sample include, without limitation, a YidX protein of the *E. coli* strain K12, a YidX polypeptide having substantially the same amino acid sequence as the YidX protein, or a fragment thereof such as an immunoreactive fragment thereof. A YidX polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a YidX protein of the *E. coli* strain K12, with the amino acid identity determined using a sequence alignment program such as CLUSTALW. Such antigens can be prepared, for example, by purification from enteric bacteria such as *E. coli*, by recombinant expression of a nucleic acid encoding a YidX peptide such as NCBI Accession No. AAT48200.1, by synthetic means such as solution or solid phase peptide synthesis. One skilled in the art will appreciate that YidX is also known as predicted lipoprotein C.

In some embodiments, the methods for aiding in the diagnosis of irritable bowel syndrome in a subject comprise determining the level of at least one bacterial antigen antibody, wherein the bacterial antigen is selected from the group consisting of EcFliC, SfFliC, CjFlaA, CjFlaB, EcEra, EcOFliC, EcFrvX, EcGabT, Cj81-045, Cj81-128, Cj81-008, and combinations thereof.

In some embodiments, the method of the present invention includes determining the presence of level of an antibody against at least one polypeptide or fragment thereof expressed by a commensal and/or opportunistic bacteria. Non-limiting examples of polypeptides expressed by commensal and/or opportunistic bacteria are presented in Table 3.

TABLE 3

Additional Bacterial Antigens.

| Name | Original name | Strain | NCBI GenBank Accession No.; Swisspro. No. | Protein function |
|---|---|---|---|---|
| LaFrc | Frc | *Lactobacillus acidophilus* | YP_193317; Q5FLY8 | Formyl CoA transferase |
| LaEno | Eno | *Lactobacillus acidophilus* | YP_193779; Q5FKM6 | Phosphopyruvate hydratase (enolase) |
| LjEFTu | EFTu | *Lactobacillus johnsonii* | NP_964865; Q74JU6 | Elongation factor EFTu |
| BfOmpA | OmpA | *Bacteroides fragilis* | YP_098863; Q64VP7 | Outer membrane protein A |
| PrOmpA | OmpA | *Prevotella* sp | EEX54413; C9PT48 | Immunoreactive antigen PG33 (OmpA) |
| Cp10bA | 10bA | *Clostridia perfringens* | EDT23004; B1V1I2 | 10b antigen |
| CpSpA | SpA | *Clostridia perfringens* | YP_209686; Q5DWA9 | Surface protective antigen |
| EfSant | Sant | *Enterococcus faecalis* | EEU72780; C7W575 | Surface antigen |
| LmOsp | Osp | *Listeria monocytogenes* | YP_002349810; B8DFK3 | Outer surface protein |

The term "LaFrc" refers to a protein of the *Lactobacillus acidophilus* that is immunoreactive with an anti-Frc antibody. Frc is predicted to be a formyl CoA transferase. Suitable Frc antigens useful in determining anti-Frc antibody levels in a sample include, without limitation, a Frc protein of the *L. acidophilus*, a Frc polypeptide having substantially the same amino acid sequence as the Frc protein of the *L. acidophilus*, or a fragment thereof such as an immunoreactive fragment thereof. A Frc polypeptide of the *L. acidophilus* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Frc protein of the *L. acidophilus*, with the amino acid identity determined using a sequence alignment program such as CLUSTALW. Such antigens can be prepared, for example, by purification from enteric bacteria such as *L. acidophilus*, by recombinant expression of a nucleic acid encoding a Frc peptide such as NCBI Ref Seq. No. YP_193317 or UniProt. No. Q5FLY8, by synthetic means such as solution or solid phase peptide synthesis.

The term "LaEno" refers to a protein of the *Lactobacillus acidophilus* that is immunoreactive with an anti-Eno antibody. Eno is predicted to be a phosphopyruvate hydratase (enolase). Suitable Eno antigens useful in determining anti-Eno antibody levels in a sample include, without limitation, an Eno protein of the *L. acidophilus*, an Eno polypeptide having substantially the same amino acid sequence as the Eno protein of the *L. acidophilus*, or a fragment thereof such as an immunoreactive fragment thereof. An Eno polypeptide of the *L. acidophilus* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Eno protein of the *L. acidophilus*, with the amino acid identity determined using a sequence alignment program such as CLUSTALW. Such antigens can be prepared, for example, by purification from enteric bacteria such as *L. acidophilus*, by recombinant expression of a nucleic acid encoding an Eno peptide such as NCBI Ref Seq. No. YP_193779 or UniProt. No. Q5FKM6, by synthetic means such as solution or solid phase peptide synthesis.

The term "LjEFTu" refers to a protein of the *Lactobacillus johnsonii* that is immunoreactive with an anti-EFTu antibody. EFTu is predicted to be an elongation factor Tu. Suitable EFTu antigens useful in determining anti-EFTu antibody levels in a sample include, without limitation, an EFTu protein of the *L. johnsonii*, an EFTu polypeptide having substantially the same amino acid sequence as the EFTu protein of the *L. acidophilus*, or a fragment thereof such as an immunoreactive fragment thereof. An EFTu polypeptide of the *L. johnsonii* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an EFTu protein of the *L. johnsonii*, with the amino acid identity determined using a sequence alignment program such as CLUSTALW. Such antigens can be prepared, for example, by purification from enteric bacteria such as *L. johnsonii*, by recombinant expression of a nucleic acid encoding an EFTu peptide such as NCBI Ref Seq. No. NP_964865 or UniProt. No. Q74JU6, by synthetic means such as solution or solid phase peptide synthesis.

The term "BfOmpA" refers to a protein of the *Bacteroides fragilis* that is immunoreactive with an anti-OmpA antibody. OmpA is predicted to be a major outer membrane protein A. Suitable OmpA antigens useful in determining anti-OmpA antibody levels in a sample include, without limitation, an OmpA protein of the *B. fragilis*, an OmpA polypeptide having substantially the same amino acid sequence as the OmpA protein of the *B. fragilis*, or a fragment thereof such as an immunoreactive fragment thereof. An OmpA polypeptide of the *B. fragilis* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an OmpA protein of the *B. fragilis*, with the amino acid identity determined using a sequence alignment program such as CLUSTALW. Such antigens can be prepared, for example, by purification from enteric bacteria such as *B. fragilis*, by recombinant expression of a nucleic acid encoding an OmpA peptide such as NCBI Ref Seq. No. YP_098863 or UniProt. No. Q64VP7, by synthetic means such as solution or solid phase peptide synthesis.

The term "PrOmpA" refers to a protein of the *Prevotella* species, e.g., *Prevotella* sp. oral taxon 472 str. F0295, that is immunoreactive with an anti-OmpA antibody. OmpA is predicted to be a immunoreactive antigen PG33 or major outer membrane protein A. Suitable OmpA antigens useful in determining anti-OmpA antibody levels in a sample include, without limitation, an OmpA protein of the *Prevotella* sp., an OmpA polypeptide having substantially the same amino acid sequence as the OmpA protein of the *Prevotella* sp., or a fragment thereof such as an immunoreactive fragment thereof. An OmpA polypeptide of the *Prevotella* sp. generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an OmpA protein of the *Prevotella* sp., with the amino acid identity determined using a sequence alignment program such as CLUSTALW. Such antigens can be prepared, for example, by purification from enteric bacteria such as *Prevotella* sp., by recombinant expression of a nucleic acid encoding an OmpA peptide such as NCBI GenBank Accession No. EEX54413 or UniProt. No. C9PT48, by synthetic means such as solution or solid phase peptide synthesis.

The term "Cp10bA" refers to a protein of the *Clostridia perfringens* that is immunoreactive with an anti-10bA antibody. 10bA is predicted to be a 10b antigen. Suitable 10bA antigens useful in determining anti-10bA antibody levels in a sample include, without limitation, a 10bA protein of the *C. perfringens*, a 10bA polypeptide having substantially the same amino acid sequence as the 10bA protein of the *C. perfringens*, or a fragment thereof such as an immunoreactive fragment thereof. A 10bA polypeptide of the *C. perfringens* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a 10bA protein of the *C. perfringens*, with the amino acid identity determined using a sequence alignment program such as CLUSTALW. Such antigens can be prepared, for example, by purification from enteric bacteria such as *C. perfringens*, by recombinant expression of a nucleic acid encoding a 10bA peptide such as NCBI GenBank Accession No. EDT72304 or UniProt. No. B1V1I2, by synthetic means such as solution or solid phase peptide synthesis.

The term "CpSpA" refers to a protein of the *Clostridia perfringens* that is immunoreactive with an anti-SpA antibody. SpA is predicted to be a surface protective antigen SpA homolog. Suitable SpA antigens useful in determining anti-SpA antibody levels in a sample include, without limitation, a SpA protein of the *C. perfringens*, a SpA polypeptide having substantially the same amino acid sequence as the SpA protein of the *C. perfringens*, or a fragment thereof such as an immunoreactive fragment thereof. A SpA polypeptide of the *C. perfringens* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a SpA protein of the *C. perfringens*, with the amino acid identity determined using a sequence alignment program such as CLUSTALW. Such antigens can be prepared, for example, by purification from enteric bacteria such as *C. perfringens*, by recombinant expression of a nucleic acid encoding a SpA peptide such as NCBI Ref Seq. No. YP_209686 or UniProt. No. Q5DWA9, by synthetic means such as solution or solid phase peptide synthesis.

The term "EfSant" refers to a protein of the *Enterococcus faecalis* that is immunoreactive with an anti-Sant antibody. Sant is predicted to be a surface antigen. Suitable Sant antigens useful in determining anti-Sant antibody levels in a sample include, without limitation, a Sant protein of the *E. faecalis*, a Sant polypeptide having substantially the same amino acid sequence as the Sant protein of the *E. faecalis*, or a fragment thereof such as an immunoreactive fragment thereof. A Sant polypeptide of the *E. faecalis* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Sant protein of the *E. faecalis*, with the amino acid identity determined using a sequence alignment program such as CLUSTALW. Such antigens can be prepared, for example, by purification from enteric bacteria such as *E. faecalis*, by recombinant expression of a nucleic acid encoding a Sant peptide such as NCBI GenBank Accession No. EEU72780 or UniProt. No. C7W575, by synthetic means such as solution or solid phase peptide synthesis.

The term "LmOsp" refers to a protein of the *Listeria monocytogenes* that is immunoreactive with an anti-Osp antibody. Osp is predicted to be an outer surface antigen. Suitable Osp antigens useful in determining anti-Osp antibody levels in a sample include, without limitation, an Osp protein of the *L. monocytogenes*, an Osp polypeptide having substantially the same amino acid sequence as the Osp protein of the *L. monocytogenes*, or a fragment thereof such as an immunoreactive fragment thereof. An Osp polypeptide of the *L. monocytogenes* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an Osp protein of the *L. monocytogenes*, with the amino acid identity determined using a sequence alignment program such as CLUSTALW. Such antigens can be prepared, for example, by purification from enteric bacteria such as *L. monocytogenes*, by recombinant expression of a nucleic acid encoding an Osp peptide such as NCBI Ref Seq. No. YP_002349810 or UniProt. No. B8DFK3, by synthetic means such as solution or solid phase peptide synthesis.

In some embodiments, the method comprises determining the level of at least one bacterial antigen antibody marker by measuring the level of antibody against the bacterial antigen present in a sample from an individual. In some instances, an individual possessing a bacterial antigen antibody is indicative of IBS. The presence or level of the bacterial antigen antibody in the individual can be correlated to the level of the disease.

In some embodiments, the invention provides a method to aid in the diagnosis of IBS, the assay comprising:
  a) contacting a sample having an anti-bacterial antigen antibody contained therein under conditions suitable to transform the anti-bacterial antigen antibody into a complex comprising the anti-bacterial antigen antibody and a capture bacterial antigen;
  b) contacting the complex with an enzyme labeled indicator antibody to transform the complex into a labeled complex;
  c) contacting the labeled complex with a substrate for the enzyme; and
  d) detecting the presence or level of the anti-bacterial antigen antibody in the sample.

For example, as illustrated in Examples 4 described herein, methods of the present invention are used to measure the levels of antibodies specific to bacterial antigens present in a sample.

In some embodiments, the level of at least one antibody against a bacterial antigen in a patient sample indicates that the patient has IBS, e.g., post-infectious IBS, wherein the bacterial antigen is selected from the group consisting of SfFliC, CjFlaA, CjFlaB, EcOFliC, SeFljB, CjCgtA, CjGT-A, Cjdmh, and combinations thereof.

In some embodiments, the level of at least one antibody against a commensal bacterial antigen in a patient sample indicates that the patient has IBS, wherein the commensal bacterial antigen is selected from the group consisting of LaFrc, LaEno, LjEFTu, BfOmpA, PrOmpA, Cp10bA, CpSpA, EfSant, LmOsp, and combinations thereof. If it is determined that the level of an antibody against a bacterial antigen from the bacterial class *Bacteroides fragilis* or *Prevotella* sp. is reduced in a sample taken from an individual, compared to the level from a normal control sample, then the individual is diagnosed as having IBS. If it is determined that the level of an antibody against a bacterial antigen from the bacterial class selected from the group consisting of *Clostridia perfringens, Enterococcus, Listeria* and other Firmicutes classes is higher in an individual's sample compared to a normal control sample, then the individual is diagnosed as having IBS.

In some embodiments, subjects with a lower level of antibodies against Bacteriodetes class bacteria compared to healthy controls are more likely to have IBS. In contrast, subjects with a higher level of antibodies against Clostridia, Mollicutes and/or Bacilli class bacteria compared to healthy control may be more likely to have IBS.

In other embodiments, the method provided herein is used to determine that a subject with an increased level (e.g., amount, concentration, ratio) of antibodies to a Firmicutes antigen such as a LaFrc, LaEno, LjEfTu, Cp10ba, CpSpaA, EfSant, and LmOsp antigen, over an Bacteriodetes antigen, such as a BfOmpA and PrOmpA antigen, is predicted that the subject has an increased likelihood of having IBS.

2. Mast Cell Marker: β-Tryptase

In one aspect, a method for aiding in the diagnosis of irritable bowel syndrome (IBS) in a subject is provided, the method comprises:
  a) determining the level of β-tryptase present in a sample from a subject; and
  b) comparing the level of β-tryptase present in the sample to that of a control level, wherein an increased level of β-tryptase present in the sample from the subject is indicative of an increase likelihood of the subjecting having IBS.

In some embodiments, the method of determining the level of β-tryptase present in a sample from a subject comprises:
  a) contacting a biological sample from the subject with a β-tryptase binding moiety under conditions suitable to transform β-tryptase present in the sample into a complex comprising β-tryptase and the β-tryptase binding moiety; and
  b) determining the level of the complex, thereby determining the level of β-tryptase present in the sample.

In a specific embodiments, the method of determining the level of β-tryptase present in a sample from a subject comprises: (a) contacting a sample having β-tryptase contained therein under conditions suitable to transform the β-tryptase into a complex comprising β-tryptase and a capture anti-tryptase antibody; (b) contacting the complex with an enzyme labeled indicator antibody to transform the complex into a labeled complex; (c) contacting the labeled complex with a substrate for the enzyme; and (d) detecting the presence or level of β-tryptase in the sample.

In a specific embodiment, the present invention provides an assay to aid in the diagnosis of IBS, the assay comprising:
a) contacting a sample having β-tryptase contained therein under conditions suitable to transform the β-tryptase into a complex comprising β-tryptase and a capture anti-tryptase antibody;
b) contacting the complex with an enzyme labeled indicator antibody to transform the complex into a labeled complex;
c) contacting the labeled complex with a substrate for the enzyme; and
d) detecting the presence or level of β-tryptase in the sample.

In some aspects, the ELISA-based β-tryptase assay comprises the following steps. A 96-well microtiter plate is coated with 100 µl of 2 µg/ml of anti-human β-tryptase antibody in sodium carbonate (pH 9.6) at 4° C. overnight. After washing with wash buffer (e.g., PBST), the plate is incubated with 300 µl/well of blocking/assay buffer (e.g., 5% BSA in PBS) at room temperature (RT) for 30 minutes with gentle agitation. After washing, 100 µl/well of sample, calibrator or control. In some instances, the sample, calibrator or control is serially diluted (1:8 in assay buffer) before adding to the plate. Typically, the calibrators are serial diluted normal pooled serum spiked with a known amount of human β-tryptase. The calibrators are used to generate a calibrator curve (e.g., standard curve) which is used to determine the level of human β-tryptase in the sample. After incubating at RT for another 2 hours, the plate is washed, and then incubated with 100 µl of alkaline phosphatase conjugated anti-human β-tryptase at an optimized dilution in assay buffer. The plate is incubated for 2 hours with gentle agitation and then washed. 100 µl of a chromogenic substrate (e.g. Tropix CSPD) is added to each well and incubated in the dark for 30 minutes before reading the luminescence with a luminescence plate reader. The Relative Luminescent Unit (RLU) and the β-tryptase concentration are plotted using graphing software such as Graphpad (Prism). The levels of β-tryptase in the sample and control are calculated by interpolation from a calibrator curve that is performed in the same assay as the sample.

In an exemplary assay, the detection range was 0.019-5000 ng/ml. The EC50 was 65 ng/ml and the recovery was 81.5% in a sample containing 20 ng of human β-tryptase spiked in normal pooled serum.

An exemplary embodiment of a method for determining the level of β-tryptase present in a sample from a subject is described in U.S. Pat. No. 8,114,616, the disclosure of which is herein incorporated by reference in its entirety for all purposes.

In preferred embodiments, β-tryptase, histamine, and/or PGE2 are detected from the same sample, although in certain instances the biomarkers may be detected in samples taken from the same individual, for example, at the same time or at different times. In certain embodiments, the biomarkers are detected in separate assays performed with different aliquots of a blood or serum sample from a subject. In other embodiments, the biomarkers are detected in a single multiplex detection assay, for example, in a Luminex xAMP assay.

3. Mast Cell Marker: Histamine

In a specific embodiment, the present invention provides an assay to aid in the diagnosis of IBS, the assay comprising:
a) contacting a sample having histamine contained therein under conditions suitable to transform the acetylated histamine into a complex comprising histamine and a capture anti-histamine antibody;
b) contacting the complex with an enzyme labeled indicator antibody to transform the complex into a labeled complex;
c) contacting the labeled complex with a substrate for the enzyme; and
d) detecting the level of histamine in the sample.

An exemplary embodiment of the assay is a histamine enzyme immunoassay such as the EIA Histamine Assay (Cat. No. IM2015, ImmunoTech). Briefly, histamine present in the sample, calibrator or control is acetylated by admixing 25 µl of acylation buffer, 100 µl of samples, calibrators or controls, and 25 µl of acylation reagent, and vortexing immediately. 50 µl of the acylated samples, calibrators or controls are added to the anti-histamine antibody coated wells of the microtiter assay plate. Then, 200 µl of alkaline phosphatase-histamine conjugate is added to the plate. The plate is incubated for 2 hours at 2-8° C. with shaking. The wells are washed with wash solution, and 200 µl of chromogenic substrate is added to the wells. The plate is incubated for 30 minutes at 18-25° C. in the dark with shaking. Then, 50 µl of reaction stop solution is added before reading the luminescence with a luminescence plate reader. The Relative Luminescent Unit (RLU) and the histamine concentration of the calibrators are plotted using graphing software such as Graphpad (Prism). The levels of histamine in the sample and control are calculated by interpolation from a calibrator curve that is performed in the same assay as the sample.

4. Mast Cell Marker: Prostaglandin E2

In a specific embodiment, the present invention provides an assay to aid in the diagnosis of IBS, the assay comprising:
a) contacting a sample having prostaglandin E2 contained therein under conditions suitable to transform the prostaglandin E2 into a complex comprising prostaglandin E2 and a capture anti-prostaglandin E2 antibody;
b) contacting the complex with an enzyme labeled indicator antibody to transform the complex into a labeled complex;
c) contacting the labeled complex with a substrate for the enzyme; and
d) detecting the level of prostaglandin E2 in the sample.

An exemplary embodiment of the assay is a PGE2 competitive enzyme immunoassay such as the Prostaglandin E2 EIA Kit-Monoclonal (Cat. No. 514010, Cayman Chemical). Briefly, 50 µl of calibrator (standard) or sample is added to wells of a precoated goat anti-mouse IgG microtiter assay plate. 50 µl of PGE2 tracer (covalently conjugated PGE2 and acetylcholinesterase) is added, and then 50 µl of anti-PGE2 mouse IgG. The plate is incubated for 18 hours at 4° C. with shaking. The plate is washed 5 times with wash buffer. 200 µl of developing reagent (e.g., Ellman's reagent) is added to the wells. The plate is incubated for 60-90 minutes in the dark with shaking. Luminescence is read at 405 nm with a luminescence plate reader. The Relative Luminescent Unit (RLU) and the prostaglandin E2 concentration of the calibrators are plotted using graphing software such as Graph-Pad Prism (GraphPad Software, La Jolla, Calif.). The levels of prostaglandin E2 in the sample and control are calculated by interpolation from a calibrator curve that is performed in the same assay as the sample.

5. Stress Hormones

The inventors have discovered that cortisol levels in serum can predict whether an individual has IBS. Healthy control individuals have higher levels of cortisol compared to individuals with IBS, including IBS-C, IBS-D and IBS-M.

In some embodiments of the present invention, the method comprises measuring the level of a stress hormone in a sample taken from a subject and comparing it to that of a control, wherein the control is a healthy control or a non-IBS control. In some instances, the stress hormone level is measured in a sample taken from the subject either in the morning or the afternoon, and compared to that of a control sample taken at the corresponding time of day. The predictive value of cortisol level for diagnosing IBS varies depending on the circadian rhythm cycle of the subject from which the sample is obtained. In some instances, the predictive value of cortisol is highest for distinguishing between healthy control and IBS-D in a sample taken in the afternoon (e.g., p.m. or post meridiem). In preferred embodiments, the stress hormone is cortisol.

Stress hormones such as cortisol, brain-derived neurotrophic factor (BDNF), ACTH, and corticotropin-releasing factor (CRF) can be measured from samples including serum, blood, saliva, urine, etc. When measuring cortisol, it is important to recognize that in a normal, healthy individual, the level follows a diurnal rhythm with the highest level in the morning and lowest around midnight. Methods of measuring cortisol levels include an ELISA assay which is available from Arbor Assays (Ann Arbor, Mich.), CisBio Bioassays (Bdford, Mass.), Enzo Life Sciences (Farmingdale, N.Y.).

In some embodiments, the method of the invention further comprises generating a ratio of the level of a stress factor to the level of another stress factor, a bacterial antigen antibody marker (e.g., EcFliC, SfFliC, CjFlaA, CjFlaB, EcEra, EcOFliC, EcFrvX, EcGabT, Cj81-045, Cj81-128, Cj81-008), inflammatory marker, (e.g., CRP, SAA, ICAM, VCAM, PII) or mast cell marker (e.g., PGE2, histamine, tryptase), wherein the ratio is predictive of IBS or an IBS subtype.

B. Methods for Monitoring Disease Progression

In another aspect, the present invention provides methods for monitoring the progression of irritable bowel syndrome in a subject, the method comprising:
a) measuring the levels of an array of bacterial antigen antibody markers (e.g., EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and mixtures thereof) and an array of mast cell markers (e.g., serum β-tryptase, histamine, and prostaglandin E2) in a biological sample taken from the subject at a plurality of time points;
b) applying a statistical analysis to the measured levels of the selected bacterial antigen antibody markers and mast cell markers to generate a disease activity profile over time, wherein the disease activity profile comprises a representation of the level of the selected bacterial antigen antibody markers and mast cell markers over time; and
c) determining whether the subject is undergoing IBS progression.

In certain embodiments, the plurality of time points comprises at least 2, 3, 4, 5, 6, 7, 8, 9, 10, 11, 12, 13, 14, 15, 16, 17, 18, 19, 20, 25, 30, 35, 40, 45, 50, or more time points. In other instances, the first time point in the plurality of time points is during the course of therapy. As non-limiting examples, each of the markers can be measured prior to therapy and/or during the course of therapy at one or more (e.g., a plurality) of the following weeks: 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 52, 54, 56, 58, 60, 62, 64, 66, 68, 70, 80, 90, 100, etc.

In some embodiments, the bacterial antigen antibody marker profile includes an empirically derived profile that is based upon an analysis of a plurality of bacterial antigen antibody markers. In one aspect, the concentration of markers or their measured concentration values are transformed into an index by an algorithm resident on a computer. In certain aspects, the profile is a synthetic or human derived output, score, or cut off value(s), which expresses the biological data in numerical terms. The profile can be used to determine or make or aid in making a clinical decision. A bacterial antigen antibody marker profile can be measured multiple times over the course of time. In one aspect, the algorithm can be trained with known samples and thereafter validated with samples of known identity.

In some embodiments, the mast cell marker profile includes an empirically derived profile that is based upon an analysis of a plurality of mast cell markers. In one aspect, the concentration of markers or their measured concentration values are transformed into a profile by an algorithm resident on a computer. In certain aspects, the profile is a synthetic or human derived output, score, or cut off value(s), which expresses the biological data in numerical terms. The profile can be used to determine or make or aid in making a clinical decision. A mast cell marker profile can be measured multiple times over the course of time. In one aspect, the algorithm can be trained with known samples and thereafter validated with samples of known identity.

In some embodiments, the therapy is the administration of a probiotic and/or a prebiotic. The term "probiotic" includes micro-organisms that are beneficial to the gastrointestinal system of the host organism when consumed. Typically, probiotics improve the interactions between the host and its intestinal microbiota. The term "prebiotic" includes non-digestible consumables that are able to stimulate the growth and/or activity of the intestinal microbiota or part thereof such that the intestinal health of the host improves. In some embodiments, the therapy is nutrition therapy. The term "nutrition therapy" includes a dietary regimen comprising foods that alleviate symptoms of IBS or are beneficial to the health of an individual's gastrointestinal system.

In some embodiments, the method for monitoring the progression or regression of IBS in a subject comprises:
a) determining the levels of 1, 2, 3, 4, 5, 6, 7, 8, or more bacterial antigen antibody marker(s) selected from the group consisting of EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and combinations thereof in a first biological sample taken at a first time; and
b) determining the level(s) of the selected bacterial antigen antibody marker(s) in a second biological sample taken at a second time; and
c) comparing the level(s) of the selected bacterial antigen antibody marker(s) present in the first sample to the level(s) of the selected bacterial antigen antibody marker(s) present in the second sample, wherein the difference in the level(s) of the selected bacterial antigen antibody marker(s) is indicative of the progression of IBS in the subject.

In some embodiments, the method for monitoring the progression or regression of IBS in a subject comprise:

a) determining the level of at least one bacterial antigen antibody marker selected from the group consisting of EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and combinations thereof in conjunction with at least one mast cell marker selected from β-tryptase, histamine, prostaglandin E2 (PGE2), and a combination thereof in a first sample at a first time point, b) determining the level(s) of the selected bacterial antigen antibody marker(s) and the selected mast cell marker(s) in a second sample at a second time point; and c) comparing the level(s) of the selected bacterial antigen antibody marker(s) and the selected mast cell marker(s), wherein the level(s) in the first sample compared to the second sample are indicative of progression or regression of IBS in the subject.

In some embodiments, an increase in the level(s) of the selected bacterial antigen antibody marker(s) and the selected mast cell marker(s) in the first sample compared to the second sample is indicative of the progression of IBS in the subject. In some embodiments, a decrease in the level(s) of the selected bacterial antigen antibody marker(s) and the selected mast cell marker(s) in the first sample compared to the second sample is indicative of regression of IBS in the subject.

In certain embodiments, the method of monitoring progression of IBS in a subject comprises determining the level of eight bacterial antigen antibody markers and two mast cell markers. In preferred embodiments, the method of monitoring progression of IBS in a subject comprises determining the level of antibodies against EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and the level of the mast cell markers tryptase and PGE2.

In some embodiments, the present invention provides a method for monitoring the progression of irritable bowel syndrome (IBS) in a subject, the method comprising:

a) contacting a first biological sample taken from the subject at a first time with a bacterial antigen antibody binding moiety (e.g., bacterial antigen or capture antigen) under conditions suitable to transform the bacterial antigen antibody marker present in the sample into a complex comprising the bacterial antigen antibody marker and the bacterial antigen antibody binding moiety;

b) determining the level of the complex, thereby determining the level of the bacterial antigen antibody marker present in the first sample;

c) contacting a second biological sample taken from the subject at a second time with a bacterial antigen antibody binding moiety under conditions suitable to transform the bacterial antigen antibody marker present in the sample into a complex comprising the bacterial antigen antibody marker and the bacterial antigen antibody binding moiety;

d) determining the level of the complex, thereby determining the level of the bacterial antigen antibody marker present in the second sample; and e) comparing the level of the bacterial antigen antibody marker present in the first sample to the level of the bacterial antigen antibody marker present in the second sample, wherein the difference in the level of the bacterial antigen antibody marker is indicative of the progression of IBS in the subject.

In some embodiments, the bacterial antigen or antibody binding moiety is selected from the group consisting of EcFliC, SfFliC, CjFlaA, CjFlaB, EcOFliC, CjGT-A, Cjdmh, CjCgtA, SeFljB, EcEra, EcFocA, EcFrvX, EcGabT, EcYbaN, EcYcdG, EcYhgN, EcYedK, EcYidX, LaFrc, LaEno, LjEFTu, BfOmpA, PrOmpA, Cp10bA, CpSpA, EfSant, LmOsp, and combinations thereof. In certain embodiments, the method comprises determining the level of at least one bacterial antigen antibody marker. In other embodiments, the method comprises determining the level of an array of bacterial antigen antibody markers.

In some embodiments, the mast cell marker is selected from the group consisting of β-tryptase, histamine, prostaglandin E2, and combinations thereof.

In some embodiment, the method further comprises determining the level of at least one mast cell marker present in the sample. In other embodiment, the method further comprising determining the level of one of a plurality of mast cell markers such as 1, 2, 3, 4, 5, 6, 7, or 8 mast cell markers.

In other embodiments, the bacterial antigen antibody binding moiety is a capture antigen that is recognized by the bacterial antigen antibody to be assayed. In some instance, the capture antigen is a bacterial antigen polypeptide or fragment thereof. Example 6 provides methods for selecting capture antigens based on their immunogenic sites.

The generation and selection of antibodies not already commercially available for analyzing or detecting the level (e.g., amount) of specific antibodies against bacterial antigens in accordance with the present invention can be accomplished several ways. For example, one way is to express and/or purify a polypeptide of interest (i.e., antigen) using protein expression and purification methods known in the art, while another way is to synthesize the polypeptide of interest using solid phase peptide synthesis methods known in the art. See, e.g., *Guide to Protein Purification*, Murray P. Deutcher, ed., *Meth. Enzymol.*, Vol. 182 (1990); *Solid Phase Peptide Synthesis*, Greg B. Fields, ed., *Meth. Enzymol.*, Vol. 289 (1997); Kiso et al., *Chem. Pharm. Bull.*, 38:1192-99 (1990); Mostafavi et al., *Biomed. Pept. Proteins Nucleic Acids*, 1:255-60, (1995); and Fujiwara et al., *Chem. Pharm. Bull.*, 44:1326-31 (1996). Purified or synthesized polypeptides of interest are commercially available from, for example, Accelagen (San Diego, Calif.), Exon Biosystems (San Diego, Calif.), and GenScript (Piscataw, N.J.). The purified or synthesized polypeptide can then be injected, for example, into mice or rabbits, to generate polyclonal or monoclonal antibodies. One skilled in the art will recognize that many procedures are available for the production of antibodies, for example, as described in *Antibodies, A Laboratory Manual*, Harlow and Lane, Eds., Cold Spring Harbor Laboratory, Cold Spring Harbor, N.Y. (1988). One skilled in the art will also appreciate that binding fragments or Fab fragments which mimic (e.g., retain the functional binding regions of) antibodies can also be prepared from genetic information by various procedures. See, e.g., *Antibody Engi-* neering: *A Practical Approach*, Borrebaeck, Ed., Oxford University Press, Oxford (1995); and Huse et al., *J. Immunol.*, 149:3914-3920 (1992).

The sample used for detecting, measuring, or determining the level of at least one bacterial antigen antibody marker and/or at least one mast cell marker is typically whole blood, plasma, serum, saliva, urine, stool (i.e., feces), tears, and any other bodily fluid, or a tissue sample (i.e., biopsy) such as a small intestine or colon sample. Preferably, the sample is serum, whole blood, plasma, stool, urine, or a tissue biopsy. In certain instances, the methods of the present invention further comprise obtaining the sample from the individual prior to detecting or determining the level of at least one bacterial antigen antibody marker in the sample. In a preferred embodiment, an additional bacterial antigen antibody marker and/or mast cell markers is detected from a blood or serum sample. In other embodiments, an additional bacterial antigen and/or mast cell marker is detected from a stool sample or a biopsy from the bowel of the subject.

C. Diagnostic Model

In some embodiments of the present invention, a diagnostic model is established using a retrospective cohort with known outcomes of a clinical subtype of IBS and healthy controls. In some instances, the diagnostic profile comprises a bacterial antigen antibody marker model and/or a mast cell marker model. The diagnostic model is generated by applying the retrospective data on individuals with IBS and healthy controls to statistical algorithms. In some embodiments, the bacterial antigen antibody model is derived by applying logistic regression analysis to the level of one or more bacterial antigen antibody markers determined in a retrospective cohort. In some embodiments, the mast cell marker model is derived by applying logistic regression analysis to the level of one or more mast cell markers determined in a retrospective cohort. For instance, as illustrated in Example 1, a diagnostic model was generated using retrospective data of bacterial antigen antibody markers and mast cell markers and a logistic regression machine learning algorithm.

D. Statistical Analysis

In certain instances, the statistical algorithm or statistical analysis is a learning statistical classifier system. As used herein, the term "learning statistical classifier system" includes a machine learning algorithmic technique capable of adapting to complex data sets (e.g., panel of markers of interest and/or list of IBS-related symptoms) and making decisions based upon such data sets. The learning statistical classifier system can be selected from the group consisting of a random forest (RF), classification and regression tree (C&RT boosted tree, neural network (NN), support vector machine (SVM), general chi-squared automatic interaction detector model, interactive tree, multiadaptive regression spline, machine learning classifier, and combinations thereof. Preferably, the learning statistical classifier system is a tree-based statistical algorithm (e.g., RF, C&RT, etc.) and/or a NN (e.g., artificial NN, etc.). Additional examples of learning statistical classifier systems suitable for use in the present invention are described in U.S. Patent Application Publication Nos. 2008/0085524, 2011/0045476 and 2012/0171672. In certain embodiments, the methods comprise classifying a sample from the subject as an IBS sample or non-IBS sample (e.g., sample from a healthy control).

In certain instances, the statistical algorithm is a single learning statistical classifier system. Preferably, the single learning statistical classifier system comprises a tree-based statistical algorithm such as a RF or C&RT. As a non-limiting example, a single learning statistical classifier system can be used to classify the sample as an IBS sample or non-IBS sample (e.g., healthy control) based upon a prediction or probability value and the presence or level of at least one diagnostic marker (i.e., diagnostic marker profile comprising a bacterial antigen antibody marker profile and/or a mast cell marker profile), alone or in combination with the presence or severity of at least one symptom (i.e., symptom profile). The use of a single learning statistical classifier system typically classifies the sample as an IBS sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. As such, the classification of a sample as an IBS sample or non-IBS sample is useful for aiding in the diagnosis of IBS in a subject.

In certain other instances, the statistical algorithm is a combination of at least two learning statistical classifier systems. Preferably, the combination of learning statistical classifier systems comprises a RF and a NN, e.g., used in tandem or parallel. As a non-limiting example, a RF can first be used to generate a prediction or probability value based upon the diagnostic marker profile, alone or in combination with a symptom profile, and a NN can then be used to classify the sample as an IBS sample or non-IBS sample based upon the prediction or probability value and the same or different diagnostic marker profile or combination of profiles. Advantageously, the hybrid RF/NN learning statistical classifier system of the present invention classifies the sample as an IBS sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In a particularly preferred embodiment, the statistical algorithm is a random forest classifier or a combination of a random forest classifier and a neural network classifier.

In some instances, the data obtained from using the learning statistical classifier system or systems can be processed using a processing algorithm. Such a processing algorithm can be selected, for example, from the group consisting of a multilayer perceptron, backpropagation network, and Levenberg-Marquardt algorithm. In other instances, a combination of such processing algorithms can be used, such as in a parallel or serial fashion.

The various statistical methods and models described herein can be trained and tested using a cohort of samples from healthy individuals and IBS patients. For example, samples from patients diagnosed by a physician, and preferably by a gastroenterologist, as having IBS or a clinical subtype thereof using a biopsy, colonoscopy, or an immunoassay as described in, e.g., U.S. Pat. Publication No. 2010/0094560, are suitable for use in training and testing the statistical methods and models of the present invention. Samples from patients diagnosed with IBS can also be stratified into IBS subtypes using an immunoassay as described in, e.g., U.S. Pat. No. 8,463,553 and U.S. Pat. Publication Nos. 2010/0094560 and 2008/0085524. Samples from healthy individuals can include those that were not identified as IBS samples. One skilled in the art will know of additional techniques and diagnostic criteria for obtaining a cohort of patient samples that can be used in training and testing the statistical methods and models of the present invention.

E. Assays and Kits

In one aspect, the present invention provides an assay for the detection of a bacterial antigen antibody marker in a sample, the method comprising the steps of: (a) coating a solid phase surface with a bacterial antigen or antigenic fragment thereof; (b) contacting the solid phase surface with a sample under conditions suitable to transform the bacterial antigen antibody present in the sample into a complex comprising the bacterial antigen and the bacterial antigen antibody; (c) contacting the bacterial antigen and the bacterial antigen antibody with a detecting antibody under conditions suitable to form a ternary complex; and (d) contacting the ternary complex with a luminescent or chemiluminescent substrate.

In one embodiment, the detecting antibody is conjugated to alkaline phosphatase. In other embodiments, the detecting antibody is not conjugated to an enzyme and the method further comprises the steps of (i) contacting the ternary complex with a third antibody conjugated to alkaline phosphatase under conditions suitable to form a quaternary complex and (ii) contacting the quaternary complex with a luminescent or chemiluminescent substrate.

Any suitable antibody pair may be used for the capture and detecting antibodies in a sandwich ELISA. One of skill in the art will know and appreciate how to select an appropriate antibody pair for the assay. Generally, two antibodies are selected that bind to the target of interest, e.g., .beta.-tryptase, at different epitopes such that the binding of the first (capture) antibody does not interfere with the second (detecting) antibody. In certain embodiments, the detecting antibody will be conjugated to an enzyme, for example, alkaline phosphatase, to aid in the detection of the complex. In other embodiments, a secondary antibody conjugated to an enzyme (e.g., alkaline phosphatase), which binds to the detecting antibody, may be used in the assay.

Generally, the complex will be detected by the use of a luminescent substrate, for example, a luminescent substrate found in a kit such as Ultra LITE (NAG Research Laboratories); SensoLyte (AnaSpec); SuperSignal ELISA Femto Maximum Sensitivity Substrate (Thermo Scientific); SuperSignal ELISA Pico Chemiluminescent Substrate (Thermo Scientific); or CPSD (disodium 3-(4-methoxyspiro{1,2-dioxetane-3,2'-(5'-chloro)tricyclo[3.3.1.13,7]decan}-4-yl) phenyl phosphate; Tropix, Inc).

The amino acid sequence of an antigenic fragment of a bacterial antigen can be identified by predicting the immunogenic sites in silico using software algorithms such as EMBOSS. For instance, the hydrophilicity, accessibility and flexibility properties of a series of peptide fragments of an antigen protein are accessed to determine the peptide fragments that are predicted to be the most antigenic (e.g., have the highest antigenic score). Detailed descriptions of using EMBOSS are found in Example 6.

In one embodiment of an assay to aid in the diagnosis of IBS, the sample is human whole blood or serum.

In another embodiment of an assay to aid in the diagnosis of IBS, the sample is obtained from a subject suspected of having IBS.

In another embodiment of an assay to aid in the diagnosis of IBS, detecting the presence or level of β-tryptase in the sample comprises the use of a detection device. In another embodiment of an assay to aid in the diagnosis of IBS, the detection device comprises a luminescence plate reader. In another embodiment of an assay to aid in the diagnosis of IBS, the detection device comprises a spectrophotometer.

In yet another embodiment, the present invention provides an assay to aid in the diagnosis of IBS, the assay comprising: (a) contacting a sample having β-tryptase, prostaglandin E2, and/or histamine under conditions suitable to transform β-tryptase, prostaglandin E2, and/or histamine into a complex β-tryptase, prostaglandin E2, and/or histamine and a capture anti-β-tryptase, anti-prostaglandin E2, and/or anti-histamine antibody; (b) contacting the complex with an enzyme-labeled indicator antibody to transform the complex into a labeled complex; (c) contacting the labeled complex with a substrate for the enzyme; and (d) detecting the presence or level of β-tryptase, prostaglandin E2, and/or histamine in the sample.

In certain embodiments, the assays provided comprise the detection of at least 1, 2, 3, 4, 5, 6, 7, 8, 9, 10, 11, 12, 13, 14, 15, 16, 17, 18, 19, 20, 21, 22, 23, 24, 25, 26, 27, 29, 30 or more of the biomarkers described herein. In preferred embodiments, the assays provide comprise the detection of at least one bacterial antigen antibody marker, at least one mast cell marker, and optionally at least one stress factor marker.

I. EXAMPLES

The following examples are offered to illustrate, but not to limit, the claimed invention.

Example 1: A Method for Aiding in the Diagnosis of IBS Using Bacterial Antigen Antibody Markers, and in Combination with Mast Cell Markers This example illustrates a method for aiding in the diagnosis of IBS using bacterial antigen antibody markers. It further illustrates a method for diagnosing IBS using a combination of bacterial antigen antibody markers and mast cell markers.

Background: Alterations in the bacterial flora are considered to be relevant pathogenetic factors in IBS. Flagellin, the primary structural component of bacterial flagella, activates both innate and adaptive immune system in individuals due to recognition by Toll-like receptor 5. Antibodies against A4-Fla2 and Fla-X (bacterial flagellin proteins) were found to be present significantly more frequently in patients with IBS compared to healthy controls (p=0.004 and p=0.009, respectively; Schoepfer et al, *Neurogastroenterol. Motil.* 20:1110-1118 (2008)). The IBS treatment rifaximin which targets the gastrointestinal microbiota appears to affect gut bacteria and reduce bacterial products that negatively affect the host individual. The response rate of rifaximin vs. placebo was shown to be 40.7% vs. 31.7% at a first endpoint, and 40.2% vs. 30.3% at a key secondary endpoint. Possible mechanisms of action of rifaximin on gastrointestinal microbiota include reduction of local mucosal engagement of bacteria such as the immune responses of the host individual, and antibiotic alteration of both the bacterial and host individual response.

Antimicrobial antibodies against bacterial flagellin (e.g., Cbir1, FlaX and Fla2) have been proven to be valuable biomarkers of inflammatory bowel disease (IBD). It has been described that subsets of recently discovered antibodies to *Escherichia coli* K12 proteins (e.g., Era, FocA, FrvX, GabT, YbaN, YcdG, YhgN, and YidX) can be used to distinguish between individuals with Crohn's Disease (CD) and healthy controls, and between individuals with CD and ulcerative colitis (Chen et al., *Mol. Cell Proteomics*, 8:1765-1776, (2009)). Individuals with post-infectious small intestine bacterial outgrowth (SIBO) associated with IBS which is often caused by infection from *Campylobacter jejuni* (*C. jejuni*, Cj), *Escherichia coli* (*E. coli*, Ec), *Salmonella enteritidis* (*S. enteritidis*, Se), *Shigella flexneri* (*S. flexneri*, Sf) may possess antibodies against flagellin proteins of the infecting bacteria (Spiller R and Garsed K., Gastroenterology, 136:1979-1988 (2009)). The flagellin proteins include *C. jejuni* FlaA, *C. jejuni* FlaB, *E. coli* FliC, *E. coli* O157:H7 FliC, *S. flexneri* Flic and *S. enteritidis* FlijB. *Salmonella enteriditis* is a species of *Salmonella enterica*. Mast cell hyperplasia is commonly observed following infection by these bacteria in both post-infectious IBS and non-post-infectious IBS.

Mast cells play an important role in the pathogenesis of irritable bowel syndrome (IBS). Increased mast cell infiltration and activation in distal gut segments are associated with symptom onset and severity of IBS. These cells are also implicated in the elevated response of visceral afferent nerves to mucosal stimulus in IBS patients. Measurement of mast cell markers such as β-tryptase, histamine and prostaglandin E2 (PGE2) have important implications in the clinical diagnosis of IBS. These markers have an important immune-regulatory function, especially in the mucosal barrier. A large number of IBS patients have an increase in mast cells markers accompanied with an altered microbiota antigen/antibody composition.

Methods: Provided herein is the development and validation of a method to aid in the diagnosis of IBS by measuring the level of bacterial antigen antibodies and mast cell markers in a sample from an individual, comparing the levels with control levels, and determining whether the individual has an increased likelihood of having IBS. In this method, the serum levels of antibodies against bacterial antigens such as *E. coli* FliC, *S. flexneri* FliC, *C. jejuni* FlaA, *C. jejuni* FlaB, *E. coli* Era, *E. coli* O157:H7 FliC, *E. coli* FrvX, *E. coli* GabT, and mast cell markers such as β-tryptase, histamine and prostaglandin E2 were measured in samples from healthy controls and patients with IBS. A logistic regression machine learning algorithm was performed with the data to select markers that are informative and predictive of a sample taken from a healthy control and an individual with IBS.

Figure 4:
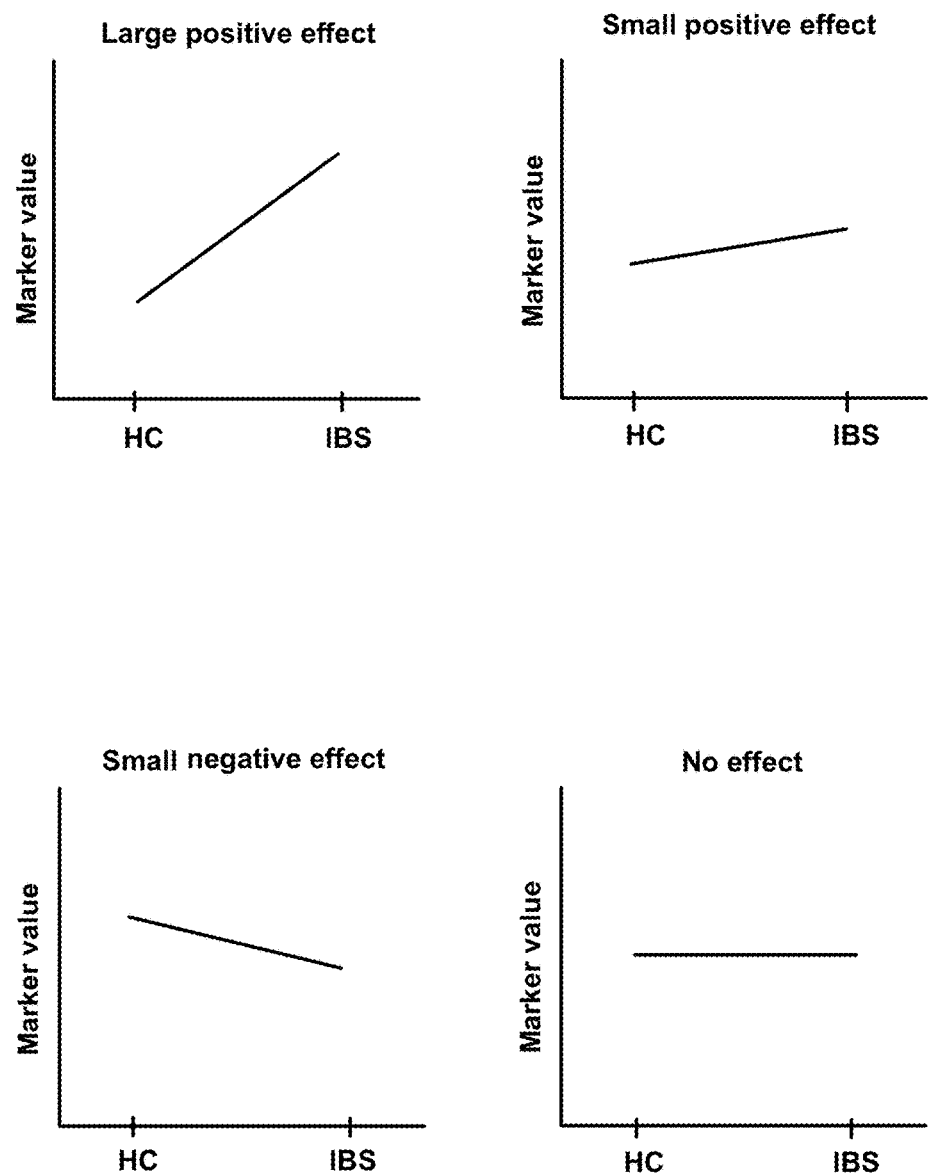
FIG. 4 illustrates the derivation of an estimated correlation coefficient of marker value vs. sample in a logistic regression model. A marker has a positive effect on the prediction of IBS vs. healthy control when the estimate corresponds to a positive slope. A marker has a large negative effect on predicting IBS when the estimate has a large negative slope. When the estimate is approximately 0, the marker provides substantially no predictive contribution to the diagnosis of IBS. The estimate value is used to determine if a specific marker is informative with predicting IBS.

The marker values for bacterial antigen antibodies and mast cell markers for the healthy control samples and the IBS samples were calculated and analyzed by logistic regression modeling. The analysis generated an estimate for each marker which represents whether the level of the marker can predict IBS or HC. FIG. 4 illustrates the derivation of the estimate from marker value and sample. The estimate can have a positive value that signifies that the marker has a positive effect on the prediction of IBS. An estimate with a larger positive value has a larger effect on discriminating IBS from HC. The estimate can have a large negative value that shows that the marker has a large negative effect on the prediction of IBS. In this case, the marker value is lower in IBS samples than HC. An estimate substantially close to 0 indicates that the marker does not contribute to the prediction of IBS.

In this study we used samples from four prospectively-collect clinical trials labeled as cohort #1-4. The samples are from either individuals with IBS and healthy controls. The selection criteria for inclusion and exclusion in the four clinical trials was specific that each particular trial and the requirements are presented in Table 4-Table 7.

TABLE 4

Cohort #1 Selection Criteria.

| | General | Healthy Controls | IBS |
|---|---|---|---|
| Inclusion | | 18-75 years old<br>Recruited from routine CRC screening subjects | 18-49 years old<br>VA/DoD eligible patients referred to GI clinic<br>Fulfil Rome II for D or M<br>No pre-existing organic GI diease that could be responsible for IBS symptoms |
| Exclusion | Pregnancy<br>Presence of "alarm features":<br>Age >= 50 + rectal bleeding + unintentional weight loss (>10 in last 6 monhts)<br>Nocturnal symptoms<br>Family history of CRC or IBD<br>Constipation predominant symptoms (<3 bowel movement in last week)<br>Previous GI evaluation for IBS | IBS-like symptoms | Existing organic disease responsible for IBS-like symptoms |

TABLE 5

Cohort #2 Selection Criteria.

| | General | Healthy Controls | IBS |
|---|---|---|---|
| Inclusion | 18-70; 50+ w/no evidence of CRC | No repeated dyspepsia, abdominal pain, constipation or diarrhea within 12 months | Dx of IBS by GI specialist within last year<br>Evidence of repeated abdominal pain<br>Females: Pain not just during menstruation<br>Pain associated with 2 or more of 1) improvement with defecation, 2) stool frequency change, 3) change |

TABLE 5-continued

Cohort #2 Selection Criteria.

| | General | Healthy Controls | IBS |
|---|---|---|---|
| Exclusion | Dx of CRC | No Rx anti-inflammatory drugs in last 2 weeks | in stool appearance<br>Symptoms occurred for at least 3 days in last 3 months<br>Presence of "alarm signs" such as unintentional weight loss (>10 pounds in 3 months), frequent awakening by symptoms, fever, rectal bleeding or anemia. |
| | Ulcer symptoms | No NSAID use >600 mg/day or 4+ times per week in last 2 weeks | Evidence of any organic, infectious or structural cause of the GI symptoms. |
| | Dx of diabetes | No GI infection in last month | No Rx anti-inflammatory drugs in last 2 weeks |
| | Dx of HIV/AIDs or chronic viral hepatitis | No injury resulting in acute inflammation in last 2 weeks | No NSAID use >600 mg/day or 4+ times per week in last 2 weeks |
| | Anti-virals Rx use | Dx of IBS or other functional GI disease/IBD/microscopic colitis/celiac | Major abdominal surgery (excl. appendectormy, polyp removal or hernia repair) |
| | Non-ambulatory | 1st degree blood relative with Dx of IBS/microscopic colitis/celiac | Dx of IBS or other functional GI disease/IBD/microscopic colitis/celiac |
| | Dx of Auto-immune disease | No travel outside US/Canada in past 30 days | 1st degree blood relative with Dx of IBS/microscopic colitis/celiac |
| | Pregnant or gave birth within 6 months | | No travel outside US/Canada in past 60 days |
| | Use of antibiotics in last month | | |
| | Use of corticosterioids in last month | | |
| | Cancer that required treatment in last 3 years | | |
| | GI symptoms resulting from food intolerance | | |

TABLE 6

Cohort #3 Selection Criteria.

| | General | Healthy Controls | IBS |
|---|---|---|---|
| Inclusion | 18-70 years old | Rome III negative for IBS or other functional GI disorders | Dx of IBS according to Rome III - D or C or M |
| | Not pregnant | No repeated instances of dyspepsia, abdominal pain constipation or diarrhea within last year | Active IBS symptoms >= 2 days in last 4 weeks |
| | Either <50 or >50 with negative colonoscopy results within 5 years | Free of any other illness/infection/significant medical condition | No other functional GI disorders |
| Exclusion | Major abdominal surgery (excl. appendectormy, polyp removal, hysterectomy, C-section or hernia repair) | Illness/infection/significant medical condition | Presence of "alarm signs" such as unintentional weight loss (>10 pounds in 3 months), frequent awakening by nocturnal diarrhea, fever, rectal bleeding not due to anal fissures or hemorrhoids, or anemia |
| | HAD score > 18 for depression/anxiety | | Dx of IBD, microscopic colitis, celiac, esophagitis, or evidence of any organic disease that could account for IBS-like symptoms (GERD excepted)<br>1st degree blood relative with Dx of IBD/celiac<br>Dx of CRC<br>Dx of cancer<br>Dx of diabetes<br>Dx of HIV/AIDs or chronic viral hepatitis<br>Dx of Auto-immune disease<br>Evidence (within the past 6 months) of symptomatic cholelithiasis<br>Bacterial/viral infection in 2 weeks prior to blood draw |

TABLE 6-continued

Cohort #3 Selection Criteria.

| General | Healthy Controls | IBS |
|---|---|---|
| | | Treatment with prohibited medication (see Section 6.2) |
| | | Pregnant/breastfeeding/gave birth in last 6 months |
| | | Dx of co-morbid non-functional GI disease |
| | | Dx of psychiatric disorder in past 2 years requiring hospitalization/suicide attempt |

TABLE 7

Cohort #4 Selection Criteria.

| | General | Healthy Controls | IBS |
|---|---|---|---|
| Inclusion | 18-65 years old | BMI <= 33 | Dx by symptoms/biopsy/procedure of IBS |
| Exclusion | Dx of IBD | Major chronic illness | Dx of Non-IBD inflammatory GI disorders |
| | Dx of auto-immune disease | Dx of Non-IBD inflammatory or inflammatory GI disorders | |

To select markers that are informative for predicting IBS, data of 17 markers including bacterial antigen antibodies and mast cell markers from samples from cohort #1-4 were applied to a logistic regression model. The calculated estimate for each of the markers is presented in Table 8. The Akaike information criterion (AIC) was used to reduce the model down to the potentially informative markers. Markers with a statistically significant estimate ($p<0.1$) were determined to be potentially informative. The bacterial antigen antibody markers determined to be predictive of IBS include E. coli FliC, S. flexneri FliC, C. jejuni FlaA, C. jejuni FlaB, E. coli Era, E. coli O157:H7 FliC, E. coli FrvX, E. coli GabT.

TABLE 8

Selecting Informative Markers For Predicting IBS.

| | Estimate | Std. Error | Z-value | P-value |
|---|---|---|---|---|
| CjFlaA | −7.53E−01 | 4.44E−01 | −1.698 | 0.0896 |
| EcEra | 5.73E+00 | 4.06E+00 | 5.575 | 2.47E−08 |
| EcFliC | −1.47E+00 | 5.88E−01 | −2.764 | 0.00572 |
| EcGabT | −1.47E+00 | 1.08E+00 | −4.618 | 8.98E−06 |
| EcOFliC | −1.02E+00 | 2.55E−01 | −8.999 | 6.87E−05 |
| SfFlic | 1.48E+00 | 8.21E−01 | 4.616 | 8.92E−06 |
| ICAM | −4.16E−06 | 2.78E−08 | −1.524 | 1.28E−01 |
| VCAM | −4.06E−08 | 2.10E−08 | −1.93 | 5.66E−02 |
| TMP1 | −8.18E−08 | 2.18E−08 | −1.484 | 1.52E−01 |
| BDNF | 5.75E−05 | 2.58E−05 | 2.272 | 2.31E−02 |
| MMP9 | 5.70E−04 | 3.84E−04 | 1.484 | 1.38E−01 |
| MP3B | 3.54E−04 | 2.22E−04 | 1.595 | 1.11E−01 |
| TWK | −8.64E−04 | 4.63E−04 | −1.867 | 6.20E−02 |
| VEGF | −9.64E−04 | 4.44E−04 | −2.171 | 9.95E−03 |
| ANCA | −6.93E−02 | 3.27E−02 | −2.122 | 3.38E−02 |
| ASCA-A | −2.86E−02 | 1.65E−02 | −1.731 | 8.35E−02 |
| ASCA-G | 2.55E−02 | 1.56E−02 | 1.638 | 1.02E−01 |

The results of the study show that determining the levels of bacterial antigen antibody markers (e.g., E. coli FliC, S. flexneri FliC, C. jejuni FlaA, C. jejuni FlaB, E. coli Era, E. coli O157:H7 FliC, E. coli FrvX, E. coli GabT) in a sample from an individual is useful in predicting whether the individual has IBS. The results also show that determining the levels of bacterial antigens and mast cell markers (e.g., β-tryptase, histamine and prostaglandin E2) positively contributes to the discrimination of IBS patients from healthy controls.

Figure 5:
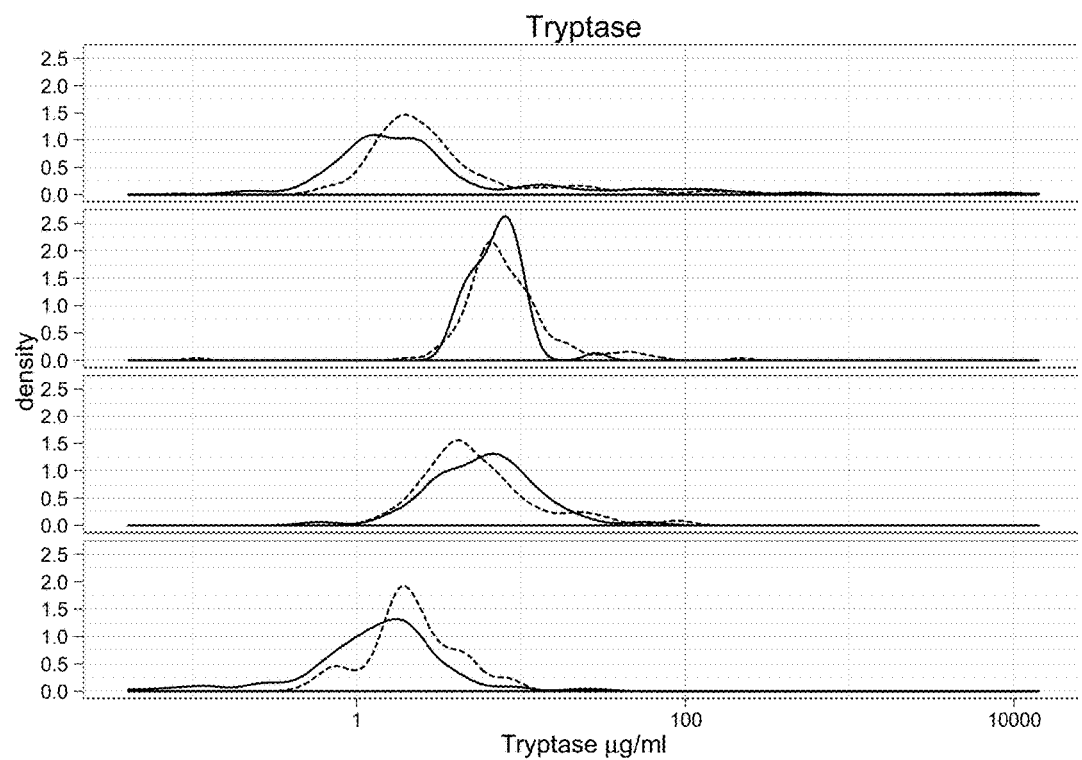
FIG. 5 illustrates a density analysis of β-tryptase data from cohorts #1-4.
Figure 5:
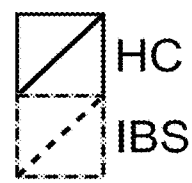

Results: The predictive capability of serum β-tryptase was analyzed using samples from cohorts #1-4. FIG. 5 depicts the distribution of serum β-tryptase in samples of healthy control versus individuals with IBS. For cohort #1, the estimate value of serum β-tryptase was 0.375 ($p=0.00697$), which indicates that the serum β-tryptase level in the sample positively contributes to the discrimination of IBS patients from healthy controls. The estimate value for cohort #2 was 0.115 ($p=0.0771$). For cohort #3, the estimate value was −0.031 ($p=0.657$) and for cohort #4, it was −0.053 ($p=0.403$). In a linear mixed model of all the data where the data is clustered by cohort, the estimate value was 0.115 ($p=0.0166$). In a linear mixed model of all the data except cohort #3, the estimate value was 0.216 ($p<0.0001$). The results showed that the level of serum β-tryptase can predict a diagnosis of IBS or healthy control.

Figure 6:
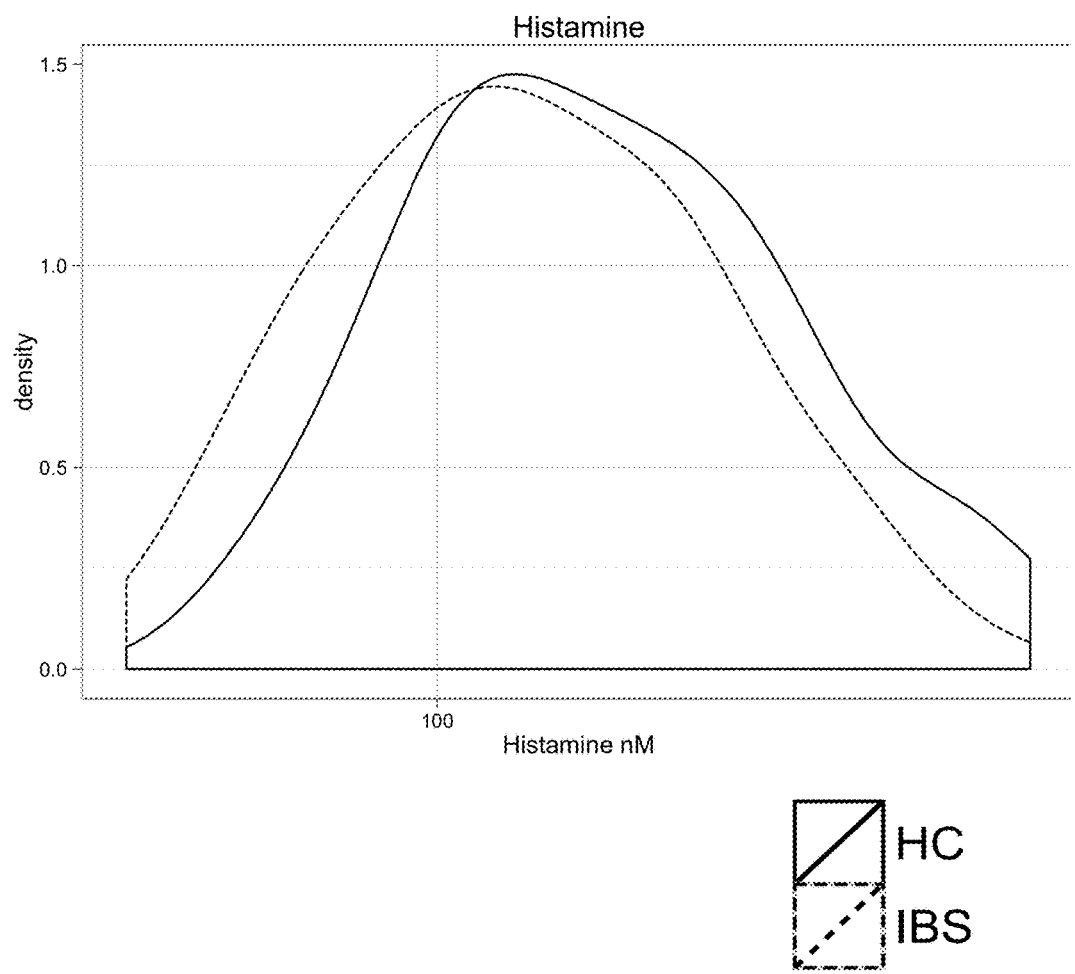
FIG. 6 illustrates a density analysis of histamine data from cohort #3.

Regression analysis of histamine level in samples from cohort #1-4 was performed. The estimate value was 0.2118 ($p=0.0023$) for cohort #1. The result indicates that histamine levels can predict a diagnosis of IBS or healthy control. FIG. 6 shows the serum histamine distribution between samples from healthy control and individuals with IBS.

Figure 7:
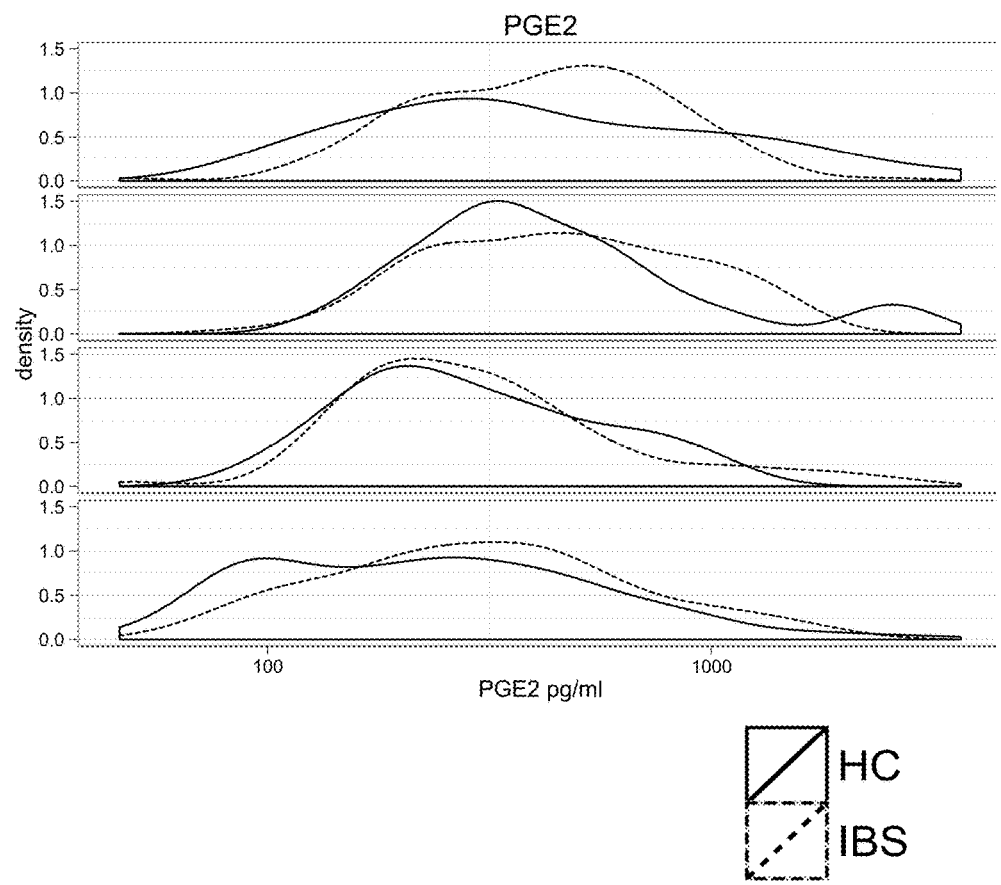
FIG. 7 illustrates a density analysis of prostaglandin $E_2$ data from cohorts #1-4.

The serum PGE2 distribution in samples from healthy control and individuals with IBS that were used in the study are shown in FIG. 7. The regression modeling of PGE2 revealed that the estimate for cohort #1 was −0.012 ($p=0.920$), 0.034 ($p=0.788$) for cohort #2, −0.220 ($p=0.029$) for cohort #3, and 0.032 ($p=0.0005$) for cohort #4. In a linear mixed model of all the data and clusters by cohort, the estimate was 0.0843 ($p=0.1167$). In a linear mixed model of all the data but excluding cohort #3, the estimate was 0.205 ($p<0.0016$). The results shows that the level serum PGE2 in a sample can predict the diagnosis of IBS and can discriminate between IBS and HC.

To determine whether the mast cell markers can be used in combination to predict IBS, we applied data from cohort

Figure 8:
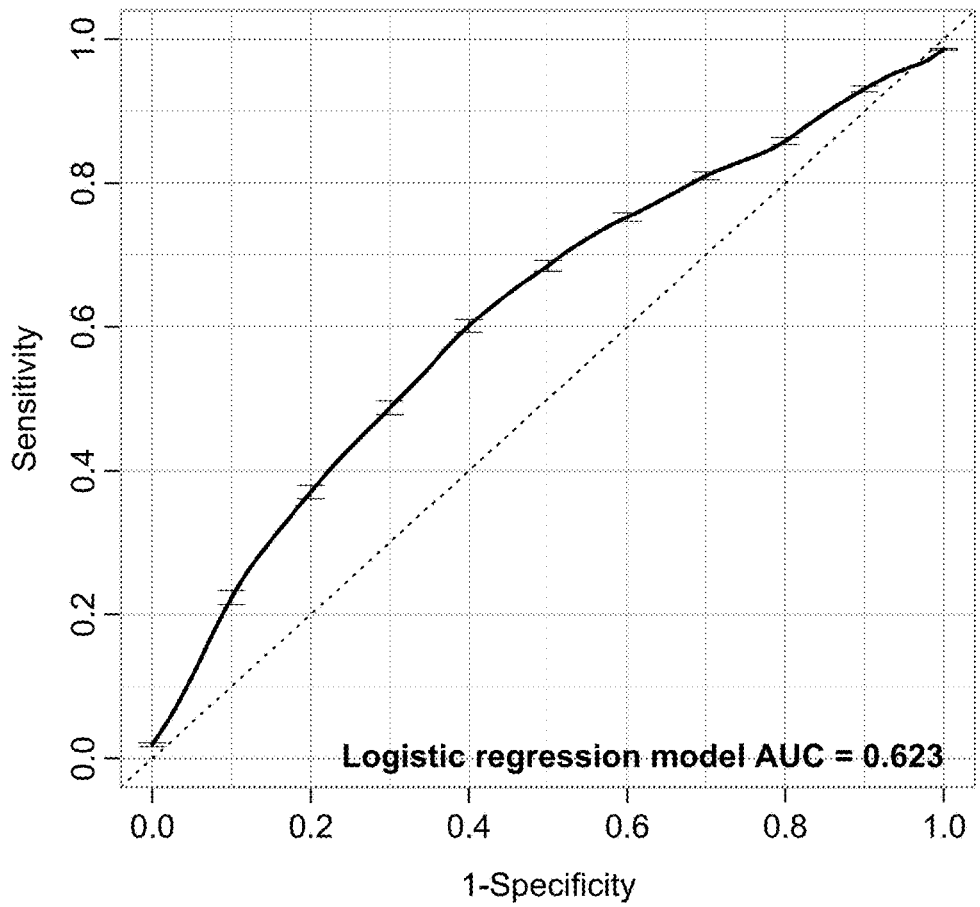
FIG. 8 illustrates a ROC curve based on a logistic regression model for predicting IBS using three mast cell markers (e.g., β-tryptase, histamine and prostaglandin E2).

1-4 for serum β-tryptase, serum histamine and PGE2 to a logistic regression model. 293 samples were analyzed and 100 train-test splits were employed for internal validation. The ROC curve with respect to sensitivity and specificity had a ROC AUC of 0.623 (FIG. 8). The results show that a combination of serum β-tryptase, histamine and prostaglandin E2 can positively contribute to the discrimination of IBS and HC.

Figure 9:
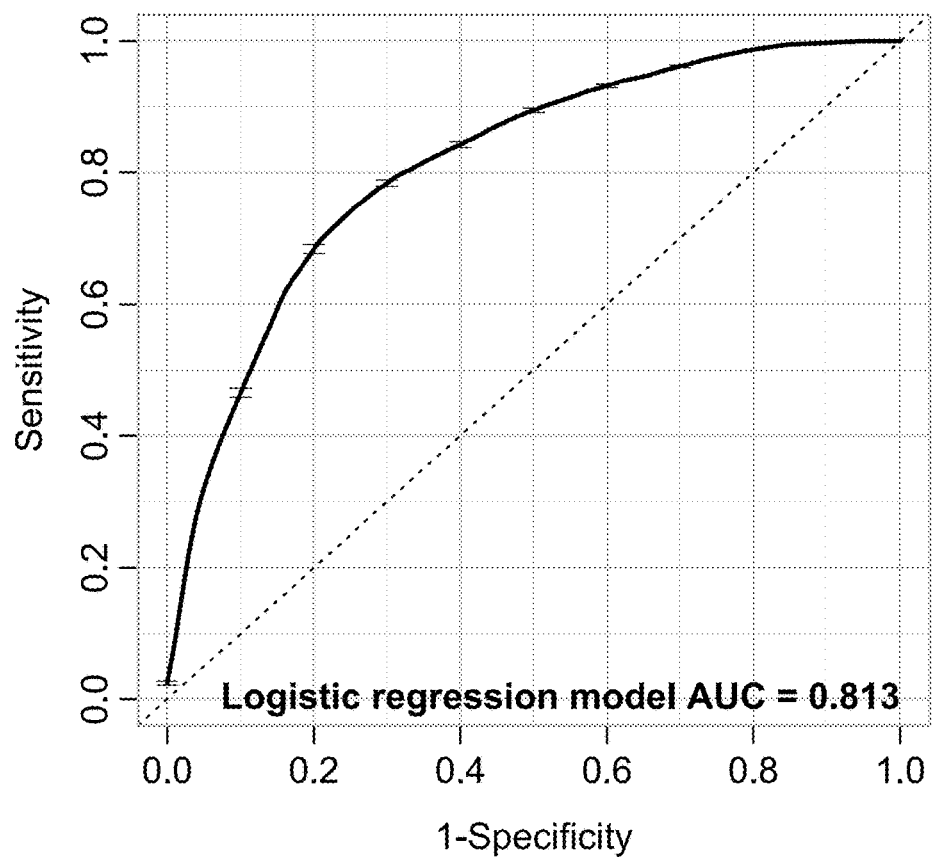
FIG. 9 illustrates a ROC curve based on a logistic regression model for predicting IBS using eight bacterial antigen antibody markers (e.g., antibodies against *E. coli* FliC, *S. flexneri* FliC, *C. jejuni* FlaA, *C. jejuni* FlaB, *E. coli* Era, *E. coli* O157:H7 FliC, *E. coli* FrvX, *E. coli* GabT, *C. jejuni* 81-045, *C. jejuni* 81-128, and *C. jejuni* 81-008).

To assess the diagnostic potential of bacterial antigen antibody markers to predicting IBS versus healthy control, we analyzed data for the bacteria antigens markers (e.g., *E. coli* FliC, *S. flexneri* FliC, *C. jejuni* FlaA, *C. jejuni* FlaB, *E. coli* Era, *E. coli* O157:H7 FliC, *E. coli* FrvX, *E. coli* GabT) from cohorts #1-4 in a logistic regression machine learning algorithm. 511 samples were evaluated and 100 train-test splits were employed for internal validation. The ROC AUC was 0.813 (FIG. 9). The results indicate that a combination of bacterial antigen antibody markers can strongly and positively contribute to the discrimination of HC and IBS in a machine learning algorithm.

Figure 10:
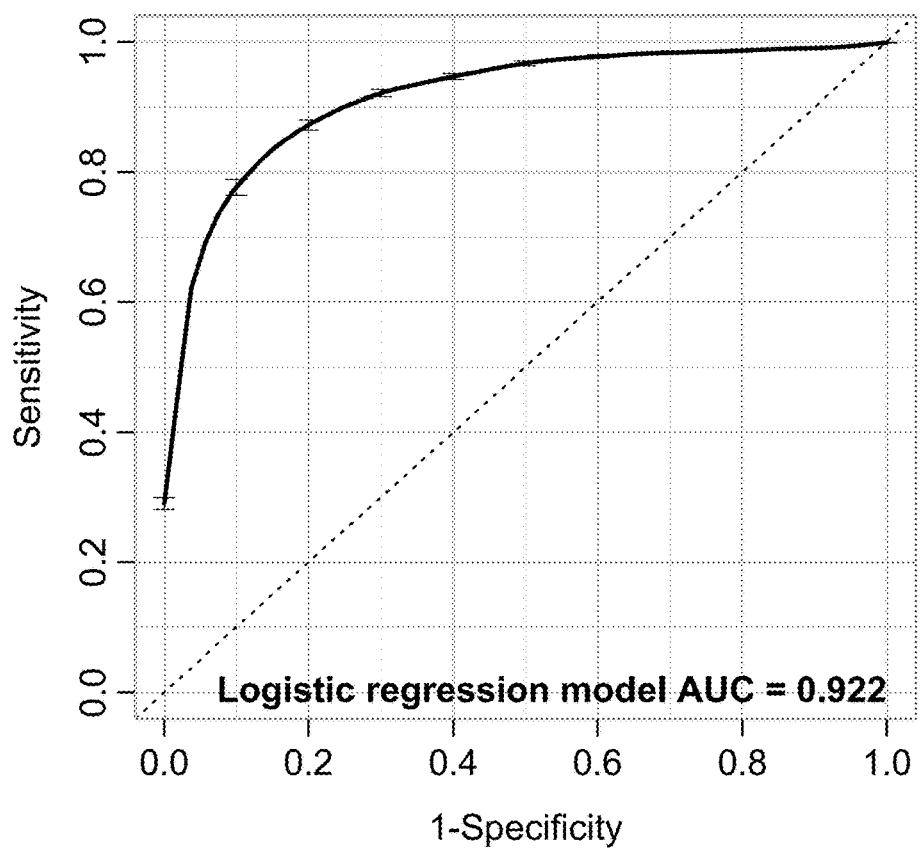
FIG. 10 illustrates a ROC curve based on a logistic regression model for predicting IBS using a combination of eight bacterial antigen antibody markers (e.g., antibodies against *E. coli* FliC, *S. flexneri* FliC, *C. jejuni* FlaA, *C. jejuni* FlaB, *E. coli* Era, *E. coli* O157:H7 FliC, *E. coli* FrvX, *E. coli* GabT *C. jejuni* 81-045, *C. jejuni* 81-128, and *C. jejuni* 81-008) and two mast cell markers (e.g., serum β-tryptase and prostaglandin E2).

To assess the diagnostic potential of bacterial antigen antibody markers and mast cell markers in predicting HC and IBS, the bacterial antigen antibody markers (e.g., antibodies against: *E. coli* FliC, *S. flexneri* FliC, *C. jejuni* FlaA, *C. jejuni* FlaB, *E. coli* Era, *E. coli* O157:H7 FliC, *E. coli* FrvX, *E. coli* GabT and combinations thereof) and the mast cell markers (e.g., PGE2 and β-tryptase) were analyzed in a single, diagnostic logistic regression algorithm. 160 samples were tested from cohort #1-4 and 100 train-test splits were used for internal validation. The ROC AUC was 0.922 (FIG. 10). The data shows that combining mast cell and bacterial antigen antibody markers provides predictive power to discriminate HC from IBS. Mast cell markers contribute additional information, not imparted by bacterial antigen antibody markers, and thus the combination of the two marker sets complement each other in a diagnostic model for predicting IBS.

Conclusion: Bacterial antigen antibody markers such as antibodies against *E. coli* FliC, *S. flexneri* FliC, *C. jejuni* FlaA, *C. jejuni* FlaB, *E. coli* Era, *E. coli* O157:H7 FliC, *E. coli* FrvX, *E. coli* GabT are effective, predictive biomarkers that differentiate IBS from HC. Bacterial antigen antibody levels can be combined with other IBS biomarkers such as mast cell markers (e.g., serum β-tryptase, histamine and prostaglandin E2) to improve the accuracy in diagnosing IBS.

Example 2: Phylogenetic Analysis of Flagellin

Background: We studied the flagellin sequences of the IBS microbiota and compared them to flagellin sequences of typical bacteria in individuals with IBD. The strategy was designed to identify candidate IBS-specific biomarkers that can discriminate IBS from IBD and/or healthy control. Typically, IBD microbiota have flagellin proteins such as CBir1, Fla2 and FlaX, while IBS microbiota have flagellin proteins such as FliC of *Escherichia coli* K12, FliC of *Shigella flexneri*, FliC of *Salmonella enteritidis*, FlaA of *Campylobacter jejuni*, FlaB of *Campylobacter jejuni*, FliC of *Escherichia coli* O157:H7, and FljB of *Salmonella enteritidis* PT4. The causative bacteria of IBS are *Campylobacter jejuni, Shigella flexneri, Escherichia coli* O157:H7, and *Salmonella enteritidis* (in order of decreasing virulence). The flagellin proteins from IBD and IBS associated bacteria used in the amino acid sequence alignment are presented in Table 9.

TABLE 9

Flagellin from IBD and IBS Associated Bacteria

| Display ID | Description |
|---|---|
| Lachnospiraceae bacterium A4 clone | *Lachnospiraceae* bacterium A4 clone 2/04 Fla2 flagellin gene, complete cds |
| bacterium Fla-X | Uncultured bacterium clone Fla-X flagellin gene, complete cds |
| bacterium CBir1 | Uncultured bacterium clone CBir-1 flagellin gene, complete cds |
| *Shigella flexneri* fliC | Flagellin OS = *Shigelia flexneri* GN = fliC PE = 3 SV = 1 |
| *Escherichia coli* fliC | Flagellin OS = *Escherichia coli* O157:H7 GN = fliC PE = 4 SV = 1 |
| *Salmonella enteritidis* fliC | *S. enteritidis* fliC gene for phase-1 flagellin (partial) |
| *Salmonella enteritidis* PT4 ftjB | Flagellin OS = *Salmonella enteritidis* PT4 (strain P125109) GN = fljB PE = 4 SV = 1 |
| *Campylobacter jejuni* flaA | FlaA OS = *Campylobacter jejuni* subsp. *jejuni* serotype O:23/36 (strain 81-176) GN = flaA PE = 4 SV = 1 |
| *Campylobacter jejuni* flaB | Flagellin B OS = *Campylobacter jejuni* subsp. *jejuni* serotype O:23/36 (strain 81-176) GN = CJJ81176_1338 PE = 4 SV = 1 |

Figure 11:
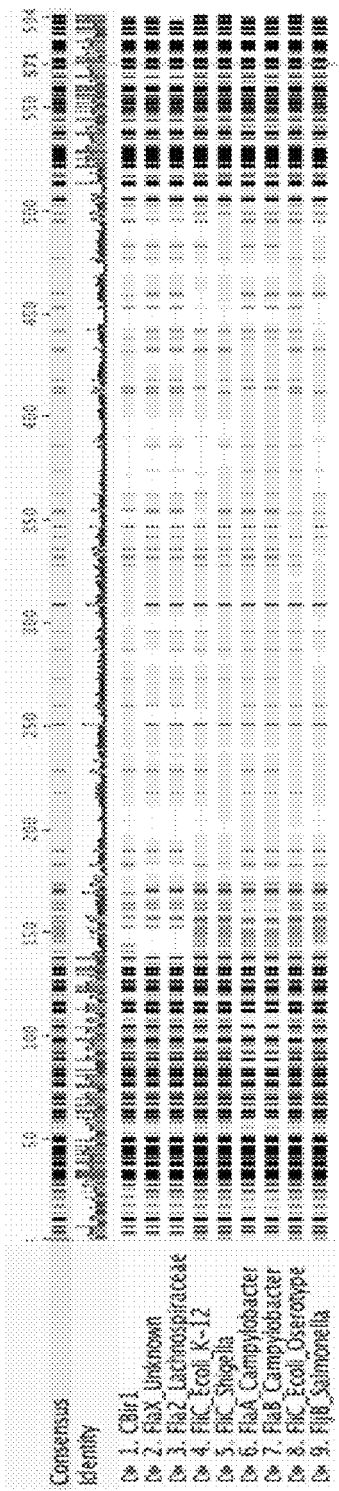
FIG. 11 illustrates an amino acid sequence alignment of flagellin from IBD bacteria, such as CBir1, Fla2 and FlaX, and flagellin from IBS bacteria such as FliC of *Escherichia coli* K12, FliC of *Shigella flexneri*, FlaA of *Campylobacter jejuni*, FlaB of *Campylobacter jejuni*, FliC of *Escherichia E. coli* O157:H7, and FljB of *Salmonella enteritidis* PT4. Green, orange and red bars show similarity levels. Black regions denote sequence similarity.
Figure 12:
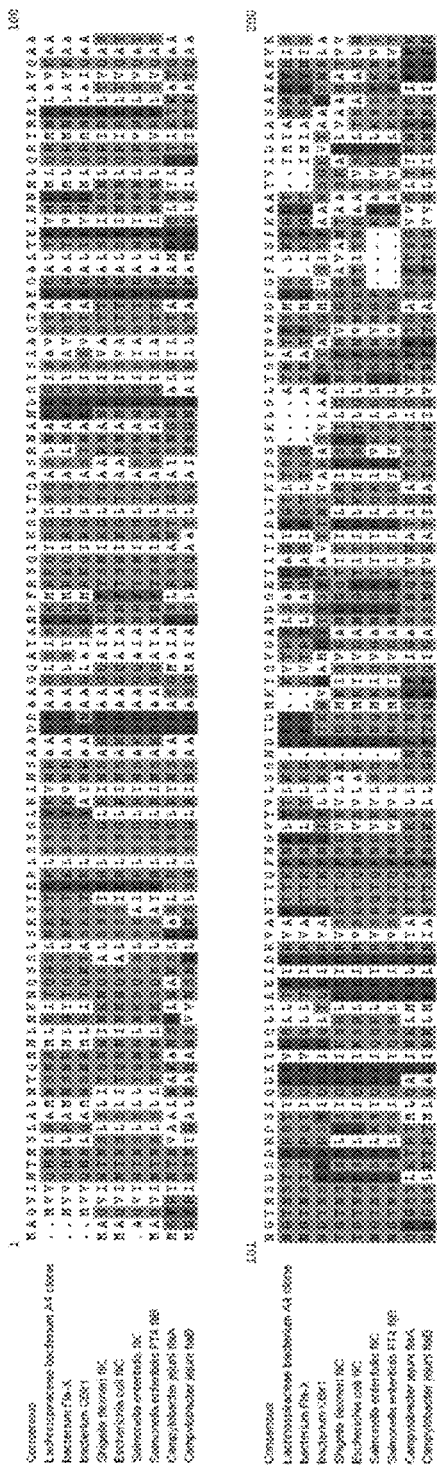
FIG. 12 illustrates an amino acid sequence alignment of the amino-terminal region of flagellin from IBD bacteria (SEQ ID NO: 19), such as CBir1 (SEQ ID NO: 12), Fla2 (Lachnospiraceae bacteria A4 clone) (SEQ ID NO: 10) and FlaX (SEQ ID NO: 11), and flagellin from IBS bacteria such as FliC of *Shigella flexneri* (SEQ ID NO: 13), FliC of *Escherichia coli* K12 (SEQ ID NO: 14), FliC of *Salmonella enteritidis* (SEQ ID NO: 15), FljB of *Salmonella enteritidis* PT4 (SEQ ID NO: 16), FlaA of *Campylobacter jejuni* (SEQ ID NO: 17), and FlaB of *Campylobacter jejuni* (SEQ ID NO: 18).
Figure 13:
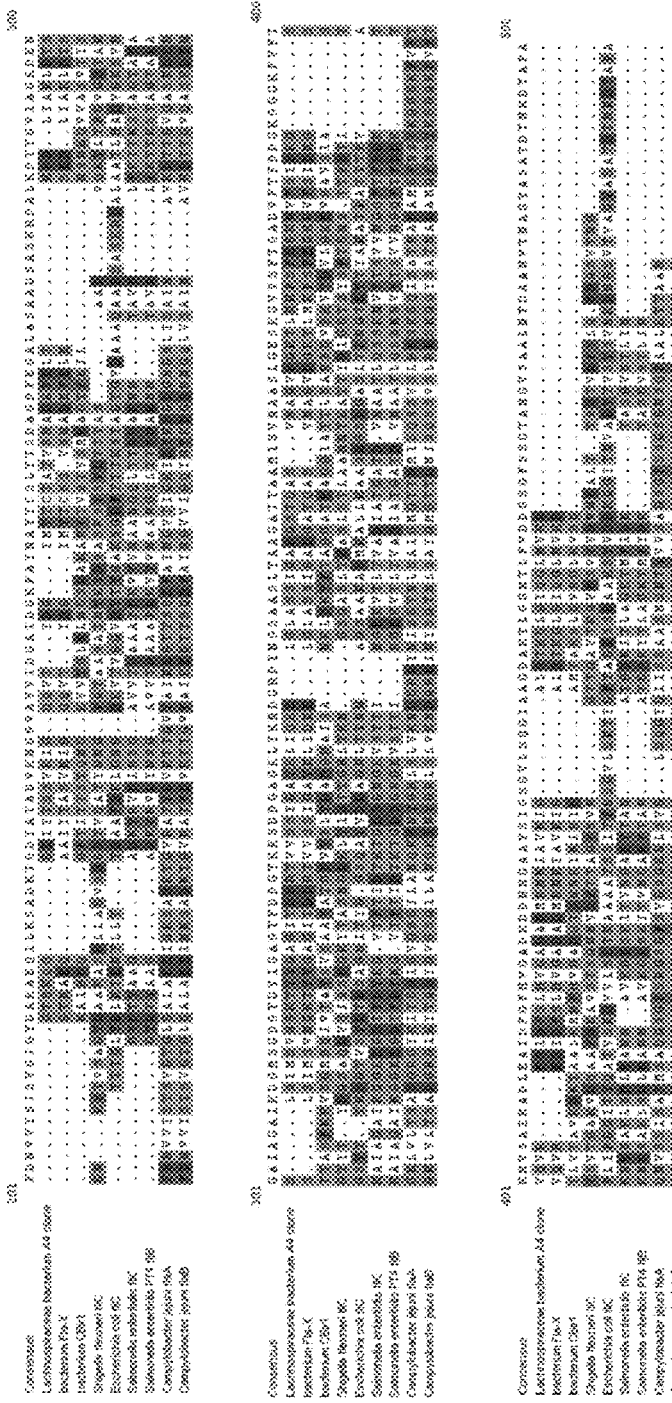
FIG. 13 illustrates an amino acid sequence alignment of the middle region of flagellin from IBD bacteria (SEQ ID NO: 19 cont.), such as CBir1 (SEQ ID NO: 12 cont.), Fla2 (Lachnospiraceae bacteria A4 clone) (SEQ ID NO: 10 cont.) and FlaX (SEQ ID NO: 11 cont.), and flagellin from IBS bacteria such as FliC of *Shigella flexneri* (SEQ ID NO: 13 cont.), FliC of *Escherichia coli* K12 (SEQ ID NO: 14 cont.), FliC of *Salmonella enteritidis* (SEQ ID NO: 15 cont.), FljB of *Salmonella enteritidis* PT4 (SEQ ID NO: 16 cont.), FlaA of *Campylobacter jejuni* (SEQ ID NO: 17 cont.), and FlaB of *Campylobacter jejuni* (SEQ ID NO: 18 cont.).
Figure 14:
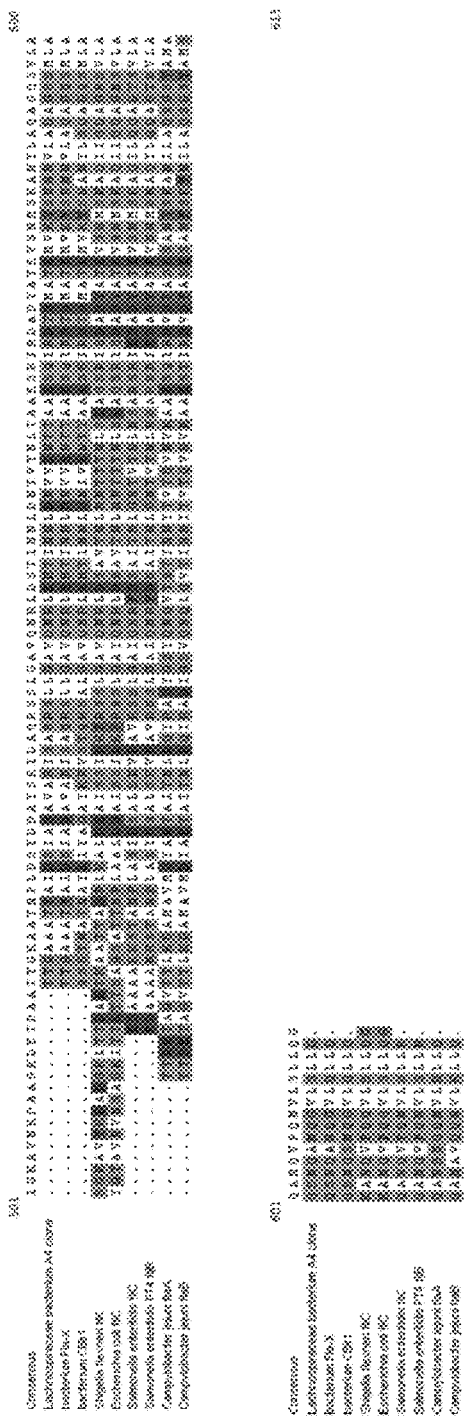
FIG. 14 illustrates an amino acid sequence alignment of the carboxy-terminal terminal region of flagellin from IBD bacteria (SEQ ID NO: 19 cont.), such as CBir1 (SEQ ID NO: 12 cont.), Fla2 (Lachnospiraceae bacteria A4 clone) (SEQ ID NO: 10 cont.) and FlaX (SEQ ID NO: 11 cont.), and flagellin from IBS bacteria such as FliC of *Shigella flexneri* (SEQ ID NO: 13 cont.), FliC of *Escherichia coli* K12 (SEQ ID NO: 14 cont.), FliC of *Salmonella enteritidis* (SEQ ID NO: 15 cont.), FljB of *Salmonella enteritidis* PT4 (SEQ ID NO: 16 cont.), FlaA of *Campylobacter jejuni* (SEQ ID NO: 17 cont.), and FlaB of *Campylobacter jejuni* (SEQ ID NO: 18 cont.).
Figure 15:
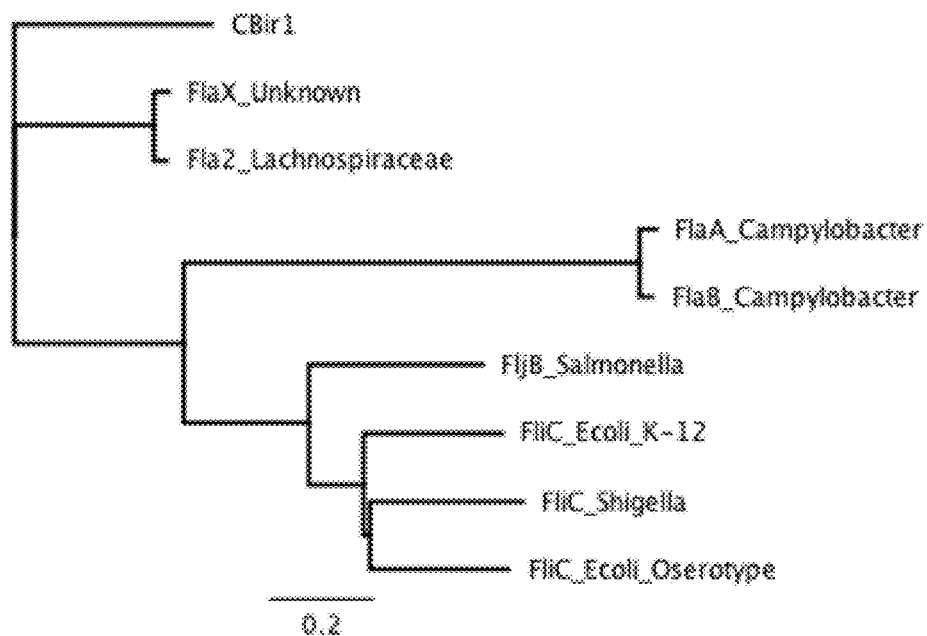
FIG. 15 illustrates a phylogenetic tree of flagellin proteins of IBD versus IBS associated bacteria.

Amino acid alignments were performed using a multiple sequence alignment algorithm. FIG. 11 shows an alignment analysis where green, orange and red bars represent levels of similarity and the black regions represent regions of more similarity. FIG. 12 depicts an alignment of the N-terminal region. FIG. 13 shows an alignment of the middle region and FIG. 14 shows the C-terminal region. At the C-terminal regions, the flagellins, A4-Fla2, FlaX and CBir1, from IBD associated bacteria are more similar to each than to the flagellin from IBS bacteria, which are more similar to each other. Of the flagellin from IBS bacteria, FlaA and FlaB of *Campylobacter jejuni* are more similar to each than to the other IBS associated flagellin. FIG. 15 shows a phylogenetic tree of the alignment data. In particular, it is an unrooted neighbor-joining tree in which CBir1 was chosen as the outgroup and branch length corresponds to distance and sequence dissimilarity. The sequence similarity of IBD vs. IBS associated flagellin is present a percent similarity matrix in Table 10.

TABLE 10

Percent Similarity Matrix of IBD and IBS Associated Flagellin

| | CBir1 | FlaX Unknown | Fla2 Lachnospiraceae | FliC EcoliK12 | FliC Shigella | FlaA Campylobacter | FlaB Campylobacter | FliC EcoliO-serotype | FljB Salmonella |
|---|---|---|---|---|---|---|---|---|---|
| CBir1 | 100.0 | 46.2 | 46.4 | 27.5 | 25.1 | 19.0 | 19.1 | 23.6 | 26.9 |
| FlaX_Unknown | 46.2 | 100.0 | 94.4 | 26.2 | 25.8 | 19.1 | 19.3 | 25.2 | 27.6 |
| Fla2_Lachnospiraceae | 46.4 | 94.4 | 100.0 | 26.4 | 26.3 | 19.3 | 19.3 | 24.9 | 27.4 |
| FliC_Ecoli_K12 | 27.5 | 26.2 | 26.4 | 100.0 | 51.8 | 23.4 | 23.6 | 49.8 | 44.9 |

TABLE 10-continued

Percent Similarity Matrix of IBD and IBS Associated Flagellin

| | CBir1 | FlaX Unknown | Fla2 Lachnos-piraceae | FliC EcoliK12 | FliC Shigella | FlaA Campylo-bacter | FlaB Campylo-bacter | FliC EcoliO-serotype | FljB Salmo-nella |
|---|---|---|---|---|---|---|---|---|---|
| FliC_Shigella | 25.1 | 25.8 | 26.3 | 51.8 | 100.0 | 21.1 | 21.5 | 54.3 | 44.6 |
| FlaA_Campylobacter | 19.0 | 19.1 | 19.3 | 23.4 | 21.1 | 100.0 | 94.8 | 21.6 | 23.0 |
| FlaB_Campylobacter | 19.1 | 19.3 | 19.3 | 23.6 | 21.5 | 94.8 | 100.0 | 21.4 | 22.3 |
| FliC_Ecoli_O serotype | 23.6 | 25.2 | 24.9 | 49.8 | 54.3 | 21.6 | 21.4 | 100.0 | 44.4 |
| FljB_Salmonella | 26.9 | 27.6 | 27.4 | 44.9 | 44.6 | 23.0 | 22.3 | 44.4 | 100.0 |

Example 3: A Serological Assay for Detecting Antibodies Against a Bacterial Antigen (Indirect Coating)

This example describes a serology assay that is useful for detecting the presence or level of a bacterial antigen antibody in a sample from an individual. The assay is detailed herein.

Protocol: A 96-well microtiter plate was coated with 100 μl/well of 1 μg/ml anti-His antibody (diluted in 1×PBS) at 4° C. overnight to allow for antibody binding to the plate. The plate was washed four times in PBS-T. Residual PBS-T was removed. The plates were coated with 100 μl His-tagged antigens at 2 μg/mL in carbonate buffer. The plates were incubated for 1.5 hr at room temperature. 250 μl/well of Blocking Buffer was added to the plate and kept at room temperature for 1 hour. Standards were prepared by making a standard of nominal 100 EU/ml (1:50) in Dilution Buffer, and then subsequently making six two-fold serial dilutions with Dilution Buffer from the 100 EU/ml Standard. The samples and positive control were prepared by making a 1:100 dilution in Dilution Buffer. After sufficient blocking, the blocking solution was removed and 100 μl/well of the standards and samples were added to the plate. The plate was incubated for 1 hour with gentle agitation. Following which, it was washed four times with PBS-T and residual PBS-T was removed. An alkaline phosphatase conjugated antibody (AP-antibody) that recognizes the bacterial antigen antibody bound to the His-tagged antigen was diluted to 1:5000 in Dilution Buffer and 100 μl/well of the diluted AP-antibody was added to the plate. After incubation for 1 hour at room temperature with gentle agitation, the plate was washed four times in PBS-T and residual PBS-T was removed. 100 μl/well of p-Nitrophenyl Phosphate was added and the plate was incubated in the dark for about 15 minutes. The enzymatic reaction was stopped upon the addition of 50 μl/well of 4N NaOH Stop Solution. The plate was read using a luminescent microplate reader at 405 nm.

Example 4: A Serological Assay for Detecting Antibodies Against a Bacterial Antigen (Direct Coating)

This example describes a serology assay that is useful for detecting the presence or level of antibodies against a bacterial antigen (e.g., E. coli FliC, S. flexneri FliC, C. jejuni FlaA, C. jejuni FlaB, E. coli Era, E. coli O157:H7 FliC, E. coli FrvX, E. coli GabT C. jejuni 81-045, C. jejuni 81-128, and C. jejuni 81-008) in a sample from an individual. The assay is detailed herein.

Protocol: A 96-well microtiter plate was coated with 100 μl/well of 1 μg/ml His-tagged bacterial antigen polypeptide or fragment thereof (diluted in 1×PBS) overnight at 4° C. The plate was washed 4 times in PBS-T. Residual PBS-T was removed. 250 μl/well of Blocking Buffer was added to the plate and kept at room temperature for 1 hour to block the plate. Standards were prepared by 1) making a Standard of nominal 100 EU/ml (1:50) using Dilution Buffer, and 2) making six two-fold serial dilutions from the 100 EU/ml Standard. The samples and positive control were prepared by making a 1:100 dilution in Dilution Buffer. After sufficient blocking, the blocking solution was removed and 100 μl/well of the standards and samples were added to the plate. The plate was incubated for 1 hour with gentle agitation. The plate was washed 4 times with PBS-T and residual PBS-T was removed. An alkaline phosphatase conjugated goat anti-human IgG antibody (AP-Goat anti-Hu IgG) was diluted to 1:5000 in Dilution Buffer and 100 μl/well of the diluted AP-Goat anti-Hu IgG was added to the plate. After incubation for 1 hour at room temperature with gentle agitation, the plate was washed 4 times in PBS-T and residual PBS-T was removed. 100 μl/well of p-Nitrophenyl Phosphate was added and the plate was incubated in the dark for about 15 minutes. The reaction was stopped upon the addition of 50 μl/well of 4N NaOH Stop Solution. The plate was read using a luminescent microplate reader at 405 nm.

Example 5: Correlation of Cortisol Levels to IBS Diagnosis

This example describes a method of determining the predictive value of cortisol level in diagnosing IBS and IBS subtypes. It also shows that a ratio of cortisol to a cytokine or bacterial antigen can aid in the diagnosis of IBS.

Figure 16:
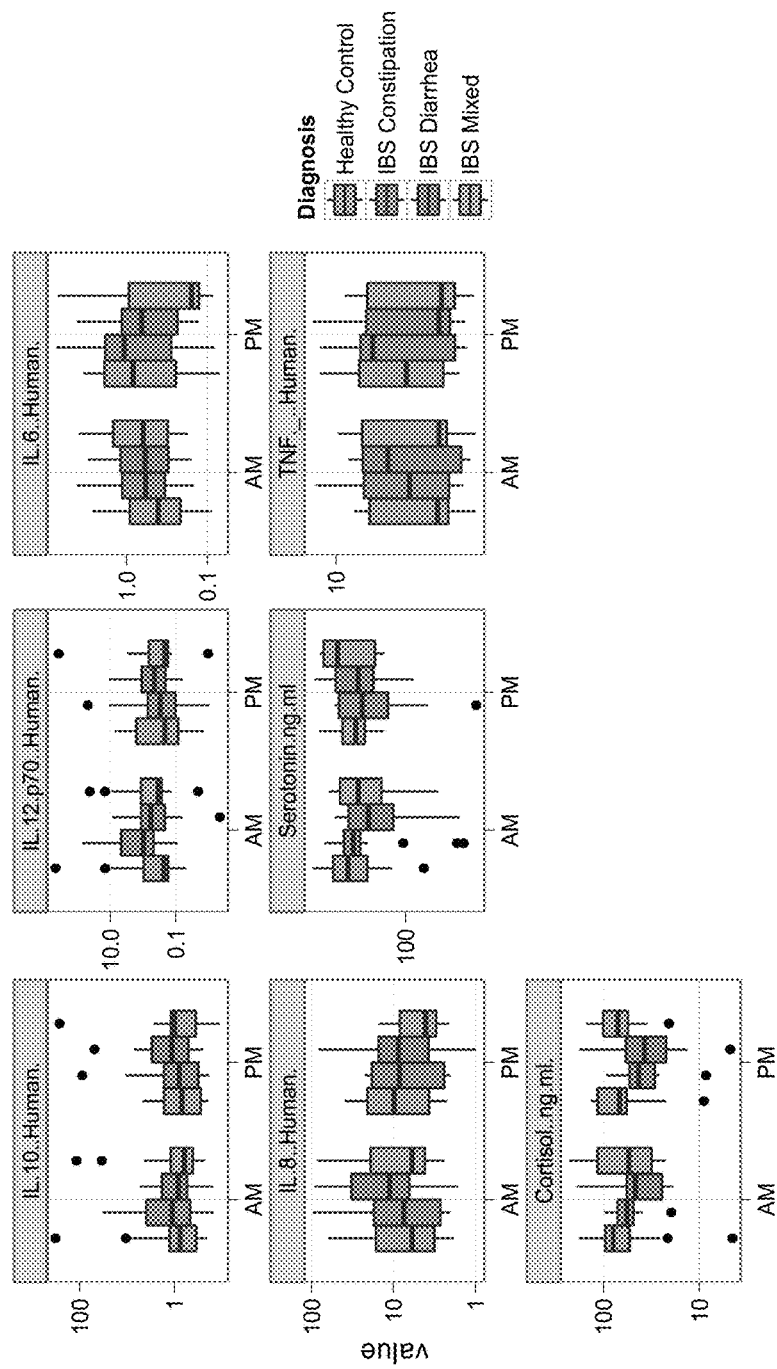
FIG. 16 illustrates levels of various cytokines (e.g., IL-10, IL-12p70, IL-6, IL-8, and TNF) and hormones (e.g., serotonin and cortisol) in the a.m. and p.m. in a retrospective cohort of patients including healthy controls, and those with IBS-C, IBS-D or IBS-M.

FIG. 16 illustrates levels of various cytokines (e.g., IL-10, IL-12p70, IL-6, IL-8, and TNF) and hormones (e.g., serotonin and cortisol) in the a.m. and p.m. in a retrospective cohort of patients including healthy controls, and those with IBS-C, IBS-D or IBS-M. The data shows that the level of IL-8, cortisol, serotonin, IL-6, and TNF are variable depending on the IBS disease state of the patient. Thus, these cytokines and hormones can aid in diagnosing IBS in a subject. Interestingly, the levels of the cytokines and hormones are different depending on the time of day that sample was taken. Linear regression analysis of cortisol levels showed that the cortisol level in a pm sample is highly predictive of healthy control versus IBS-D (FIG. 17).

Figure 18:
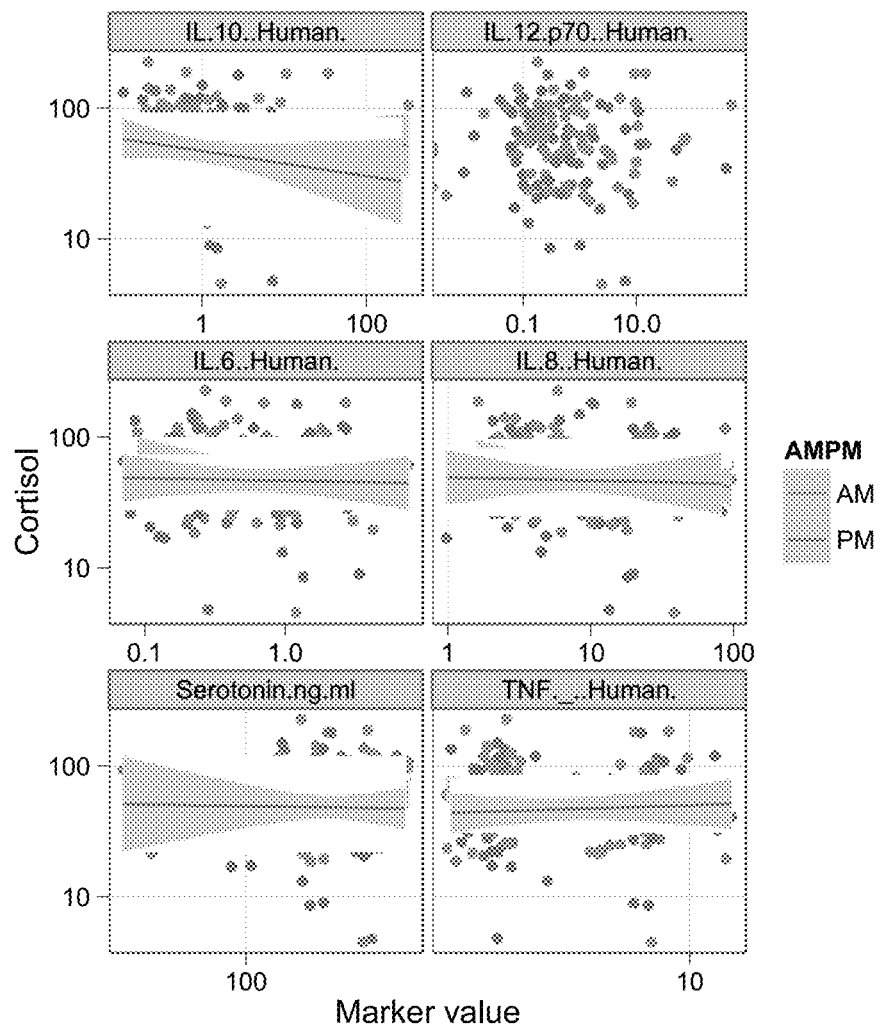
FIG. 18 illustrates the relationship between the level of cortisol and the level of other markers (e.g., IL-10, IL12p70, 11-6, IL-8, serotonin, and TNF-α in the data set from the cohort. No significant associations were identified in the linear regression model.

The relationship between cortisol and either hormones or cytokines was investigated. No other significant associations were found between the level of cortisol and the level of other markers in the data set from the cohort (FIG. 18). There was a non-statistically significant association between IL-6 and cortisol (p=0.0674).

Figure 19:
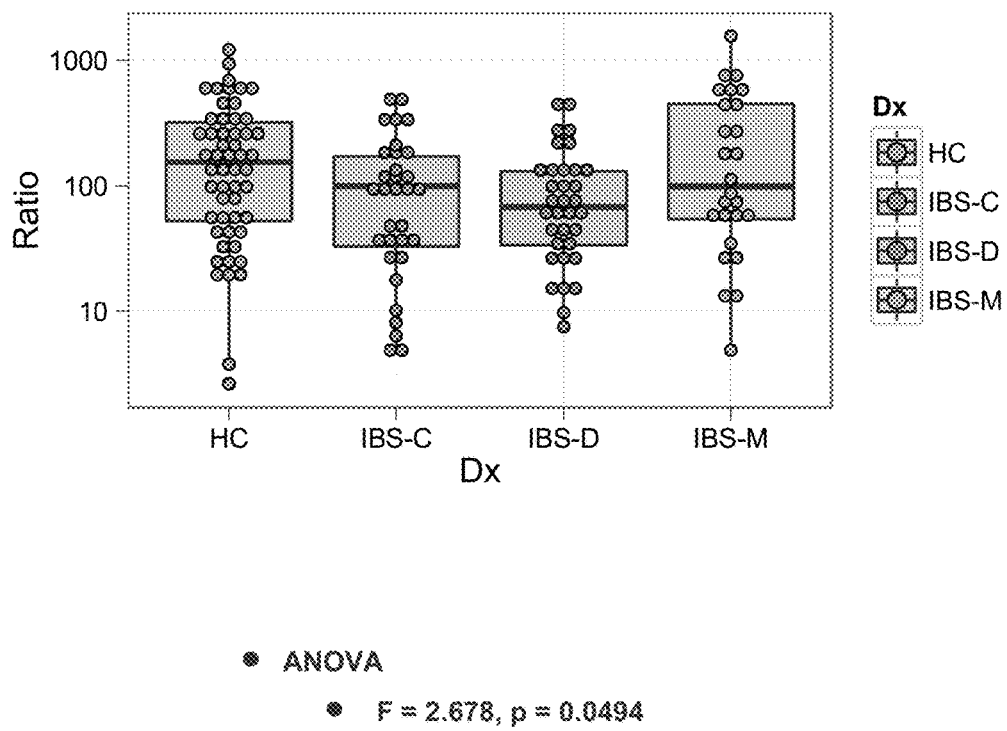
FIG. 19 shows the cortisol:IL-6 ratio for healthy control (HC) patients, and those with IBS-C, IBS-D or IBS-M.

The data was analyzed and used to generate a ratio of cortisol to IL-6 for each patient set. FIG. 19 shows the cortisol:IL-6 ratio for healthy control patients, and those with IBS-C, IBS-D or IBS-M.

Figure 20:
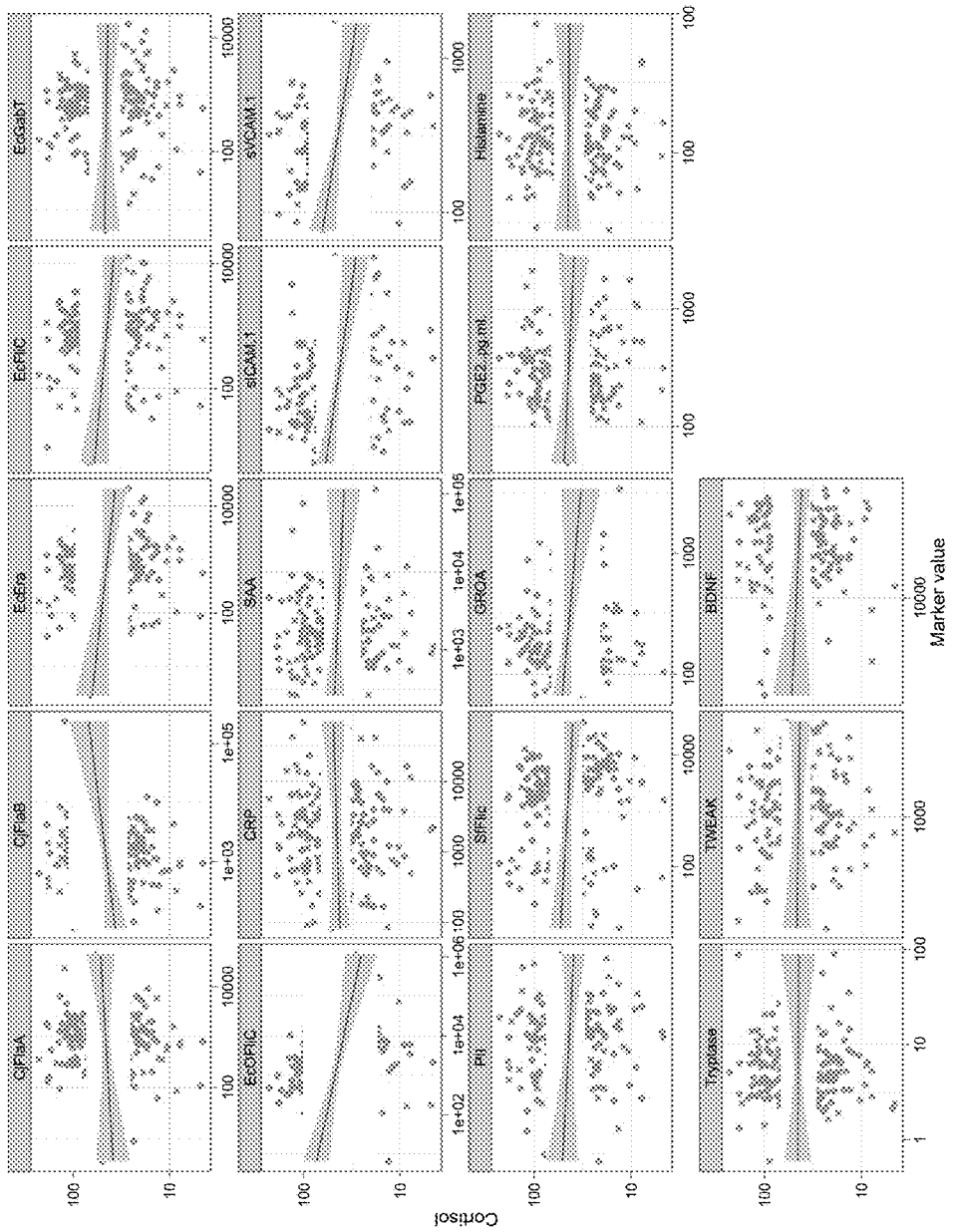
FIG. 20 shows the relationship between cortisol and other markers (e.g., CjFla, CjFlaB, EcEra, EcFlic, EcGabT, EcOFliC, CRP, SAA, sICAM, sVCAM, PII, SfFlic, GROA, PGE2, histamine, tryptase, TWEAK and BDNF) in the data set.
Figure 22:
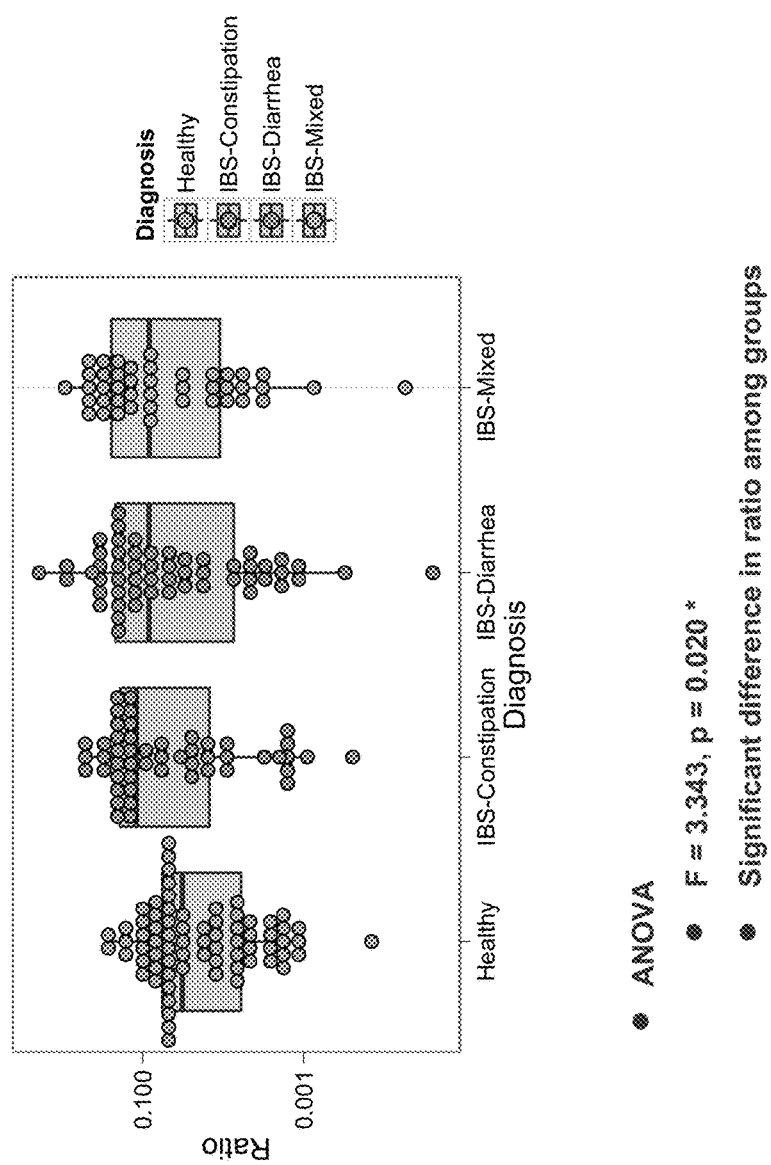
FIG. 22 shows that the ratio of cortisol to the antibodies against the bacterial antigen EcOFliC is significantly different among the healthy control, IBS-C, IBS-D and IBS-M patients (F=3.343, p=0.020). A statistically significant difference in ratio was determined among groups.
Figure 23:
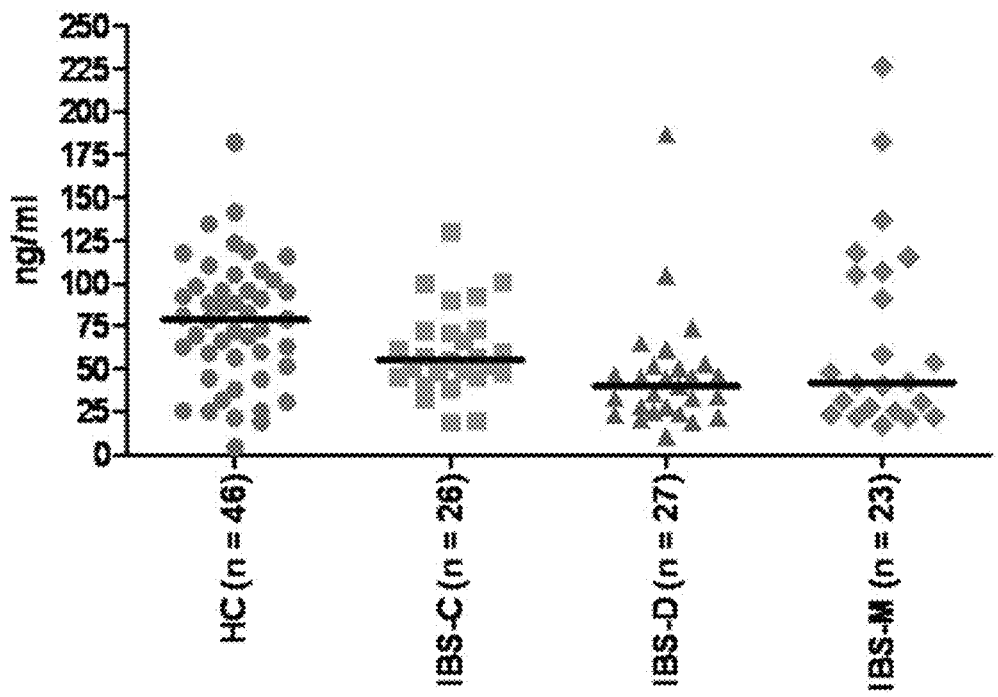
FIG. 23 shows the level of cortisol in the healthy control, IBS-C, IBS-D and IBS-M patients of the cohort.

The analysis was expanded to identify an association between a stress hormone (e.g., cortisol or BDNF) and either another stress factor, a bacterial antigen antibody marker (e.g., EcFliC, SfFliC, CjFlaA, CjFlaB, EcEra, EcOFliC, EcFrvX, EcGabT, Cj81-045, Cj81-128, Cj81-008), inflammatory cytokine marker, (e.g., CRP, SAA, ICAM, VCAM, PII) or mast cell marker (e.g., PGE2, histamine, tryptase). FIG. 20 shows the cortisol based analysis in graphical form. FIG. 21 shows the results of multiple linear regression on log-transformed variables. The method is based on evaluating the relationship of one specific marker to cortisol while controlling for the other markers of the data set. FIG. 22 shows that the ratio of cortisol to the bacterial antigen EcOFliC is significantly different among the patient groups (F=3.343, p=0.020). Thus, the ratio of cortisol: EcOFliC is predictive of IBS and can aid in the diagnosis of IBS and/or subtypes thereof. FIG. 23 shows the level of cortisol in the healthy control, IBS-C, IBS-D, and IBS-M patients.

Example 6: Predicting the Immunogenic Sites of Bacterial Antigen Proteins

This example illustrates a method for predicting the immunogenic sites (e.g., regions) of bacterial antigen proteins. A peptide corresponding to the immunogenic site of a bacterial antigen protein can be generated and used in the methods described in, e.g., to capture antibodies against the bacterial antigen located in a sample, such as a serum sample from a human suspected of having or having IBS.

I. Methods

Using EMBOSS software which is open source (see, e.g., Kolaskar et al. (1990) *FEBS Letters* 276:172-174), it was possible to predict antigenic sites of the antigen proteins. The software incorporated 169 antigenic determinants, which were experimentally determined. It selected those 156 which have less than 20 amino acids per determinant (total 2066 residues) and calculated f(Ag) as frequency of occurrence of each residue in antigenic determinants [f(Ag)=Epitope_occurrence/2066].

Hydrophilicity, accessibility and flexibility of the protein segments was assessed according to known methods (see, e.g., Kolaskar et al.; Parker J M R, et al. (1986) *Biochemistry* 25:5425-5432). In a given protein, the sum of the hydrophilicity, accessibility, and flexibility parameters for each residue of a 7-mer was assigned to central residue of 7-mer. A residue was considered to be on the surface if any of the 7-mer values was above the average for the protein. These results were used to calculate the frequency, f(s), of occurrence of amino acids at the surface. This method was used for the 20 naturally occurring amino acids, as described by Kolaskar et al. Values for B, Z, X were calculated using weighted averages from Edayhoff.dat (Dayhoff data) and were ignored when calculating totals. Antigenic propensity, A(p), was calculated as A(p)=f(Ag)/f(s).

Antigenic determinants were predicted using the following steps:
1) the average propensity for each overlapping 7-mer was calculated and assigned to the central residue (i.e, i+3);
2) the average A(p)$_{av}$ was calculated for the whole protein;
3) (a) If A(p)$_{av}$≥1.0 for the whole protein, then all residues having A(p)≥1.0 were considered potentially antigenic;
3) (b) If A(p)$_{av}$<1.0 for the whole protein, then all residues having A(p)>A(p)$_{av}$ were considered potentially antigenic;
4) 6-mers where all consecutive residues were selected by step 3 were considered to be antigenic determinants.

The parameters selected using the methods are summarized in the following Table 11.

TABLE 11

Parameters for predicting antigenic determinants.

| Antigenic Amino Acid | Occurrence of amino acids in | | | Frequency f(Ag) | Frequency f(s) | Frequency A(p) |
|---|---|---|---|---|---|---|
| | Epitopes | Surface | Protein | | | |
| A | 135 | 328 | 524 | 0.065 | 0.061 | 1.064 |
| B | 107 | 334 | 410 | 0.052 | 0.062 | 0.827 |
| C | 53 | 97 | 186 | 0.026 | 0.018 | 1.412 |
| D | 118 | 352 | 414 | 0.057 | 0.066 | 0.866 |
| E | 132 | 401 | 499 | 0.064 | 0.075 | 0.851 |
| F | 76 | 180 | 365 | 0.037 | 0.034 | 1.091 |
| G | 116 | 343 | 487 | 0.056 | 0.064 | 0.874 |
| H | 59 | 138 | 191 | 0.029 | 0.026 | 1.105 |
| I | 86 | 193 | 437 | 0.042 | 0.036 | 1.152 |
| K | 158 | 439 | 523 | 0.076 | 0.082 | 0.93 |
| L | 149 | 308 | 684 | 0.072 | 0.058 | 1.25 |
| M | 23 | 72 | 152 | 0.011 | 0.013 | 0.826 |
| N | 94 | 313 | 407 | 0.045 | 0.058 | 0.776 |
| P | 135 | 328 | 411 | 0.065 | 0.061 | 1.064 |
| Q | 99 | 252 | 332 | 0.048 | 0.047 | 1.015 |
| R | 106 | 314 | 394 | 0.051 | 0.058 | 0.873 |
| S | 168 | 429 | 553 | 0.081 | 0.08 | 1.012 |
| T | 141 | 401 | 522 | 0.068 | 0.075 | 0.909 |
| V | 128 | 239 | 515 | 0.062 | 0.045 | 1.383 |
| (Withdrawn) | 19 | 55 | 103 | 0.009 | 0.01 | 0.893 |
| X | 118 | 306 | 453 | 0.057 | 0.057 | 1.025 |
| Y | 71 | 158 | 245 | 0.034 | 0.029 | 1.161 |
| Z | 119 | 342 | 433 | 0.058 | 0.064 | 0.916 |
| Total | 2066 | 5340 | 7944 | | | |

II. Results

A. Antigenic Fragments for EcEra

Figure 24:
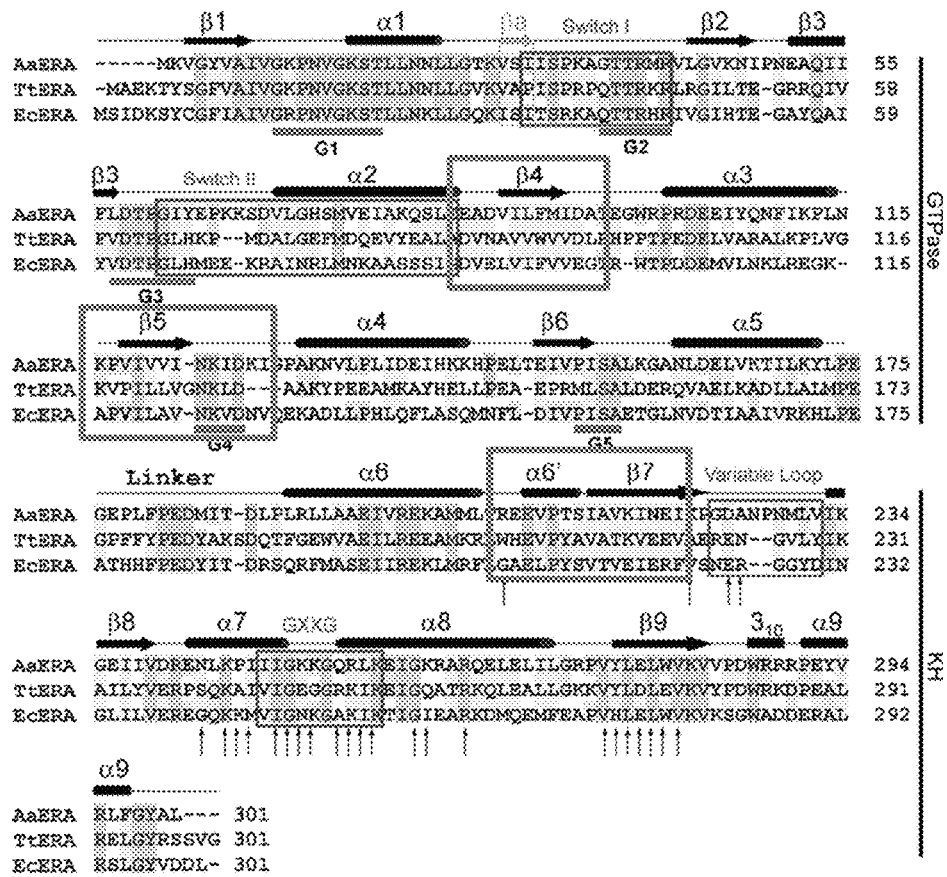
FIG. 24 shows antigenic fragment predictions (boxed) for EcEra using EMBOSS (SEQ ID NO: 20, SEQ ID NO: 21, SEQ ID NO: 22).

Using EMBOSS software available on-line, it was possible to predict antigenic fragment sequences of EcEra. The highest antigenic fragments appear in FIG. 24. The 3 highest antigenic scores for EcERA are as follows:

```
1.  Score 1.213 length 13 at residues 86->98 *
    Sequence: IGDVELVIFVVEG (SEQ ID NO: 1)
    86 98 Max_score_pos: 92

2.  Score 1.194 length 14 at residues 116->129 *
    Sequence: KAPVILAVNKVDNV (SEQ ID NO: 2)
    116 129 Max_score_pos: 120

3.  Score 1.166 length 15 at residues 207->221 *
    Sequence: GAELPYSVTVEIERF (SEQ ID NO: 3)
    207 221 Max_score_pos: 213
```

The foregoing fragments can be used alone or in combination in the methods herein to bind to the autoantibodies in a sample.

B. Antigenic Fragments for EcGabT

Figure 25:
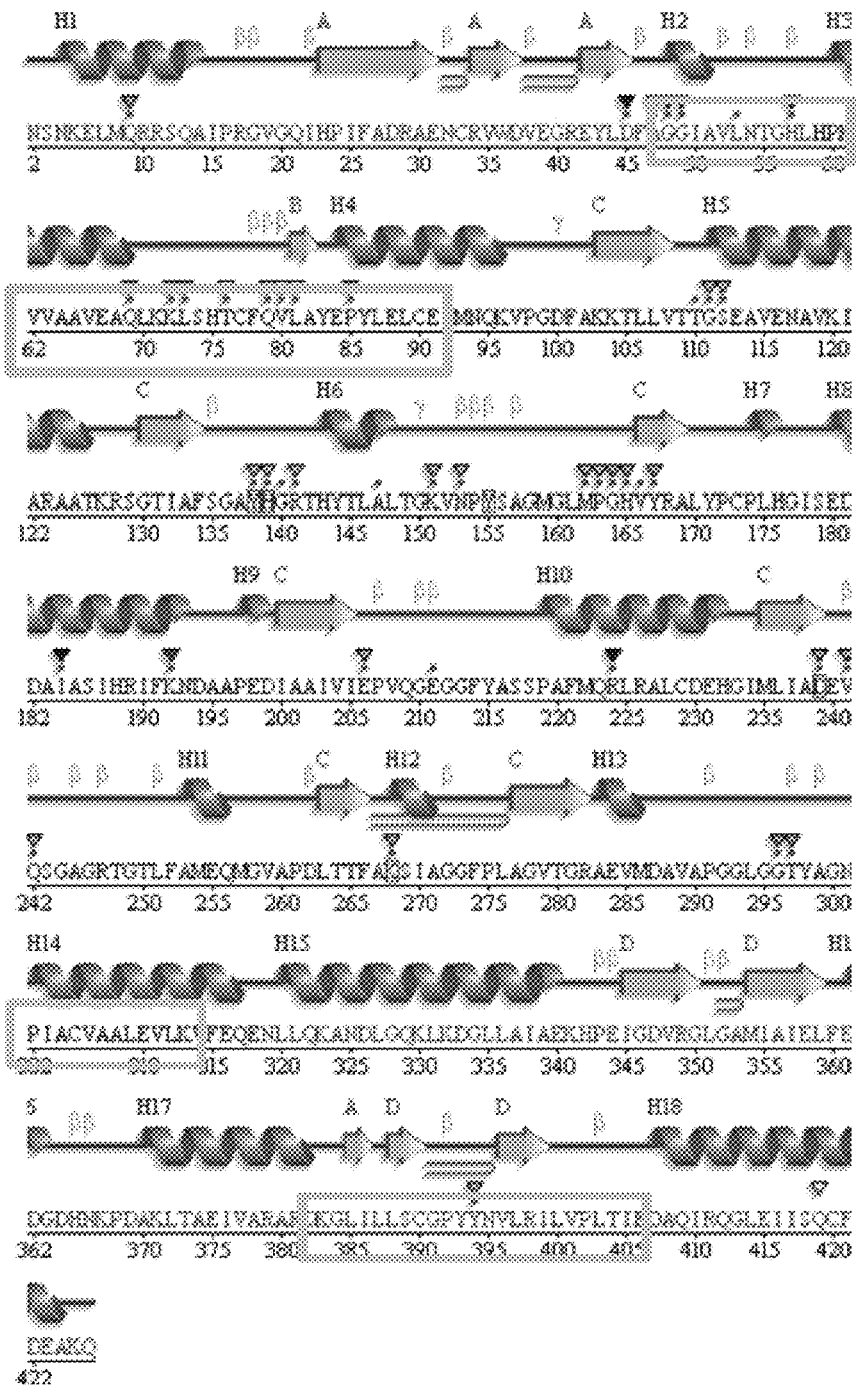
FIG. 25 shows antigenic fragment predictions (boxed) for EcGabt using EMBOSS (SEQ ID NO: 23).
Figure 26:
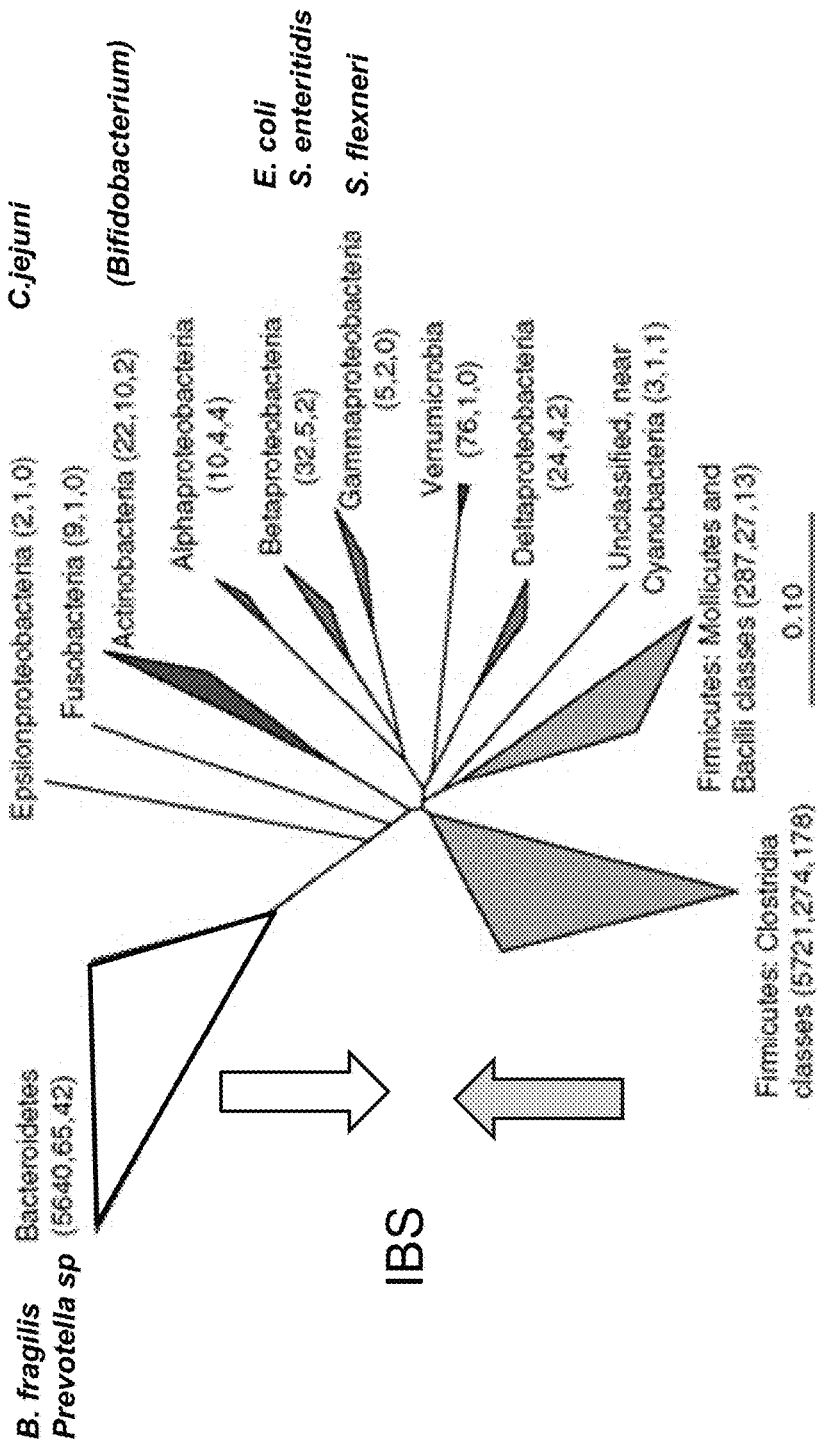
FIG. 26 shows a phylogenetic tree based on the combined human intestinal 16S rDNA sequence data set. Each clade is labeled in parentheses to include the total number of recovered sequences, phylotypes, and novel phylotypes (See, Eckburg et al., Science 308:1635-1638; Jeffery et al., Gut 61:997-1006 (2012)).

Using EMBOSS software as above, it was possible to predict antigenic fragment sequences of EcGabT. The highest antigenic fragments appear in FIG. 25. The 3 highest antigenic scores for EcGabT are as follows:

```
1.  Score 1.201 length 16 at residues 300->315 *
    Sequence: GNPIACVAALEVLKVF (SEQ ID NO: 4)
    300 315 Max_score_pos: 308

2.  Score 1.197 length 44 at residues 49->92 *
    Sequence:
    GIAVLNTGHLHPKVVAAVEAQLKKLSHTCFQVLAYEPYLELCEI
    (SEQ ID NO: 5)
    49 92 Max_score_pos: 80
```

-continued

```
3. Score 1.194 length 25 at residues 383->407 *
   Sequence: KGLILLSCGPYYNVLRILVPLTIED
   (SEQ ID NO: 6)
   383 407 Max_score_pos: 399
```

C. Antigenic Fragments for EcFrvX

Using EMBOSS software as above, it was possible to predict antigenic fragment sequences of EcFrvX. The 3 highest antigenic scores for EcFrvX are as follows:

```
1. Score 1.258 length 15 at residues 303->317 *
   Sequence: RPVVALCLPTRYLHA (SEQ ID NO: 7)
   303 317 Max_score_pos: 307

2. Score 1.212 length 22 at residues 215->236 *
   Sequence: SAEHIKPDVVIVLDTAVAGDVP (SEQ ID NO: 8)
   215 236 Max_score_pos: 224

3. Score 1.160 length 9 at residues 54->62 *
   Sequence: PKVAVVGHM (SEQ ID NO: 9)
   54 62 Max_score_pos: 58
```

A summary of the antigenic peptides for the E. Coli K12 proteins is provided below.

PrOmpA, Cp10bA, CpSpA, EfSant and LmOsp in serum samples from healthy controls and IBS patients using the assay method described in Example 4. The results demonstrate that individuals with IBS-D or IBS-M have a lower level (e.g., amount or concentration) of particular bacterial antigen antibodies compared to normal, healthy individuals.

Figure 27A:
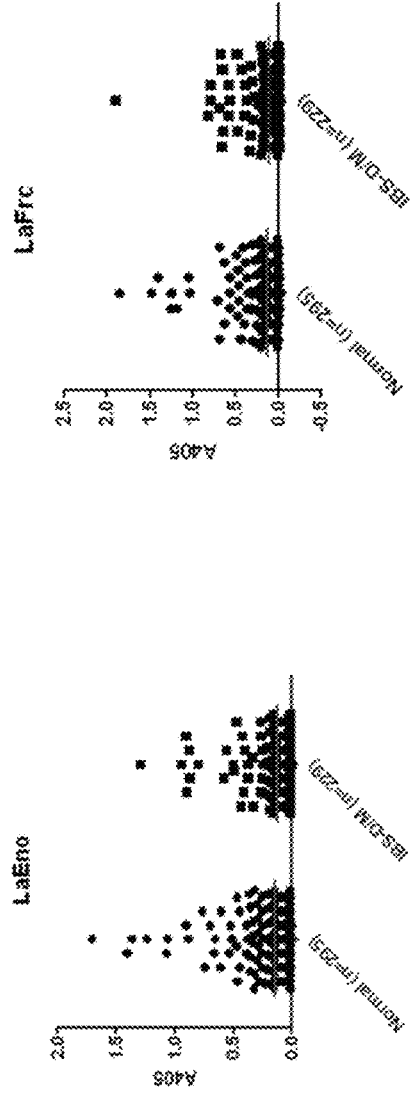
FIGS. 27A-C show the levels of antibodies against *L. acidophilus* Eno (FIG. 27A), antibodies against *L. acidophilus* Frc (FIG. 27B) and antibodies against *L. johnsonii* EFTu (FIG. 27C) in serum samples from normal control individuals and patients with IBS-D or IBS-M.
Figure 27B:
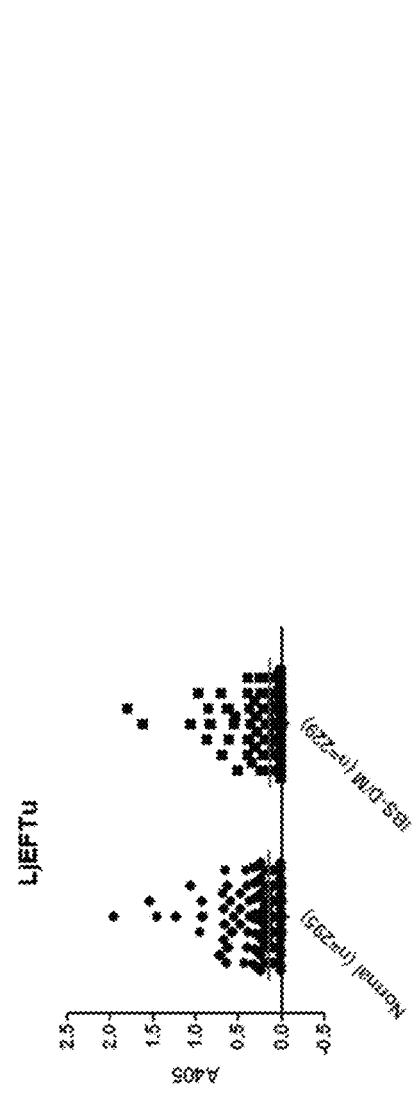
Figure 27C:
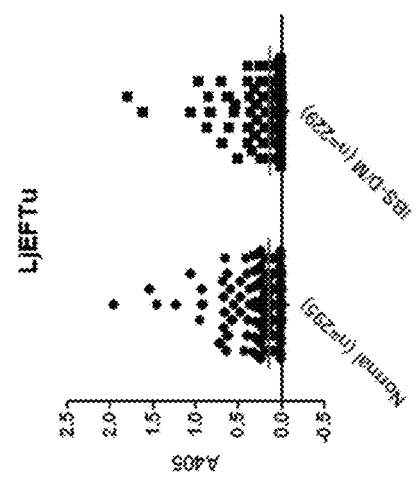

The levels of antibodies against *L. acidophilus* Eno, *L. acidophilus* Frc and *L. johnsonii* EFTu were not statistically different between the healthy control samples (n=295) and the sample taken from IBS-D or IBS-M (IBS-D/M) patients (n=229) (FIG. 27A-C).

Figure 28B:
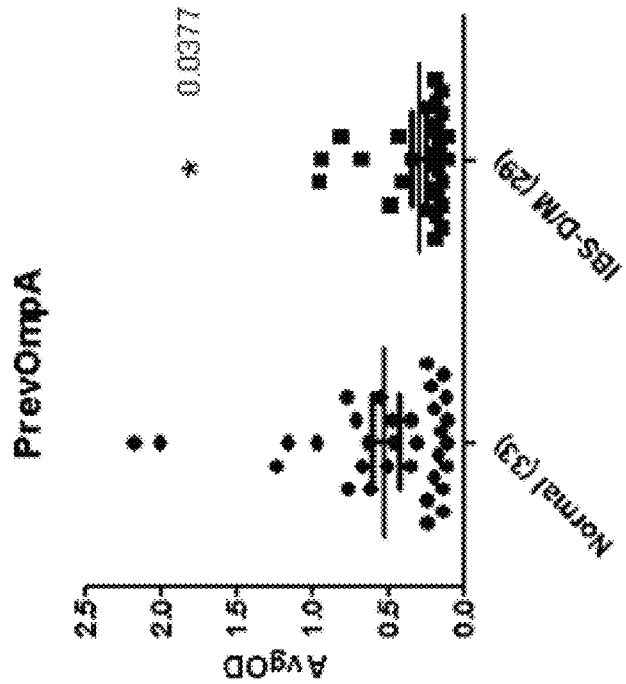
FIGS. 28A-B show the levels of antibodies against *B. fragilis* OmpA (FIG. 28A) and antibodies against *Prevotella* OmpA (FIG. 28B) in serum samples from normal control individuals and patients with IBS-D or IBS-M.
Figure 28A:
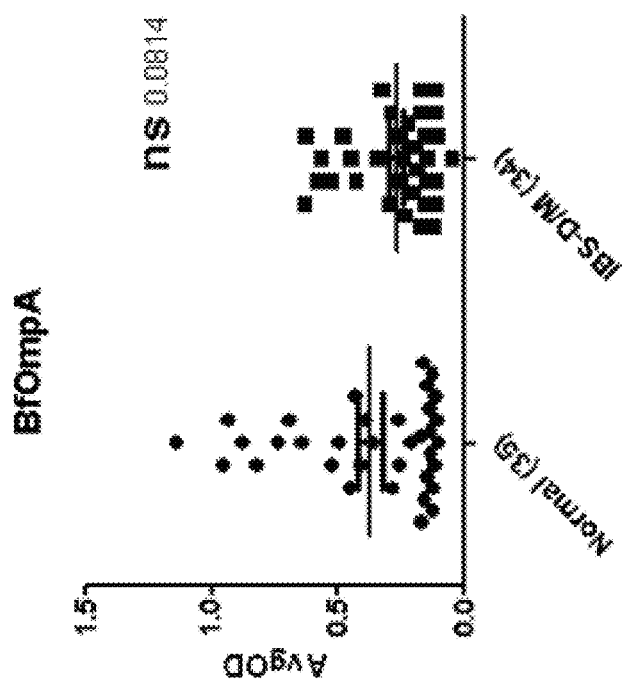
Figure 29B:
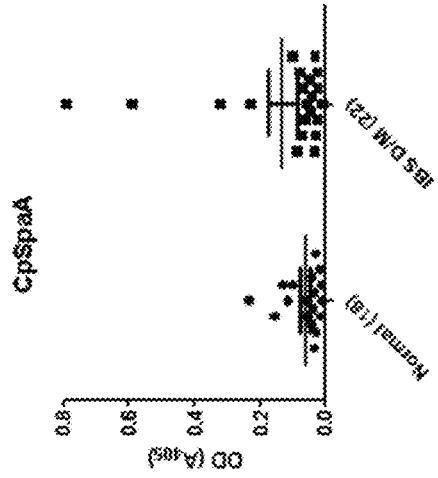
FIGS. 29A-D show the levels of antibodies against *C. perfringens* 10bA (FIG. 29A), antibodies against *C. perfringens* SpA (FIG. 28B), antibodies against *E. faecalis* Sant (FIG. 29C), and antibodies against *L. monocytogenes* Osp (FIG. 29D) in serum samples from normal control individuals and patients with IBS-D or IBS-M.
Figure 29D:
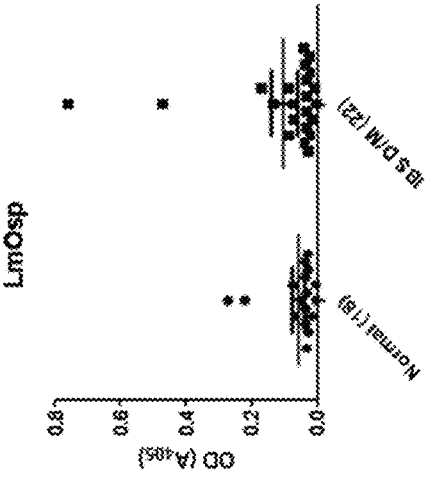
Figure 29A:
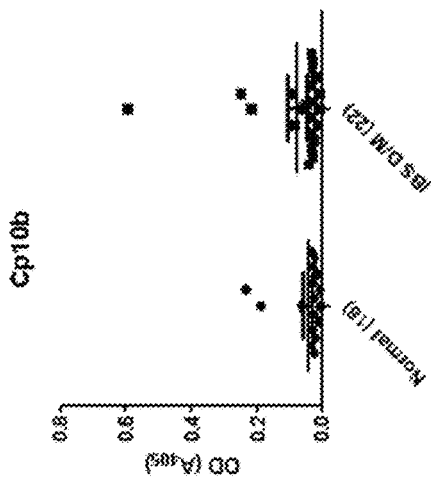
Figure 29C:
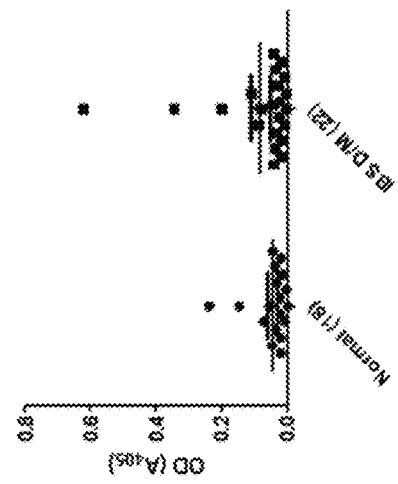

The level of antibodies against *B. fragilis* OmpA also was not statistically different (p-value=0.0814) between the healthy controls (n=35) and the IBS-D/M individuals (n=34) (FIG. 28A). However, the level of antibodies against *Prevotella* OmpA was statistically different (p-value=0.0377) between the healthy group (n=33) and the IBS-D/M group (n=29) (FIG. 28B). In particular IBS-D/M patients had a lower level of PrOmpA (PrevOmpA) compared to normal controls.

The levels of antibodies against *C. perfringens* 10bA, *C. perfringens* SpA, *E. faecalis* SA (Sant) and *L. monocytogenes* Osp were not statistically different between the

TABLE 12

Antigenic peptides for *E. Coli* K12 Proteins

| Antigen | SEQ ID NO: | Peptide sequence | EMBOSS antigenicity score (residue with max score) |
|---|---|---|---|
| EcEra | SEQ ID NO: 1 | $^{86}$IGDVELVIFVVEG$^{98}$ | 1.213 (aa 92) |
|  | SEQ ID NO: 2 | $^{116}$KAPVILAVNKVDNV$^{129}$ | 1.194 (aa 120) |
|  | SEQ ID NO: 3 | $^{207}$GAELPYSVTVEIERF$^{221}$ | 1.166 (aa 213) |
| EcGabT | SEQ ID NO: 4 | $^{300}$GNPIACVAALEVLKVF$^{315}$ | 1.201 (aa 308) |
|  | SEQ ID NO: 5 | $^{49}$GIAVLNTGHLHPKVVAAVEAQLKKLSHTCFQVLAYEPYLELCEI$^{92}$ | 1.212 (aa 80) |
|  | SEQ ID NO: 6 | $^{383}$KGLILLSCGPYYNVLRILVPLTIED$^{407}$ | 1.194 (aa 399) |
| EcFrvX | SEQ ID NO: 7 | $^{303}$RPVVALCLPTRYLHA$^{317}$ | 1.258 (aa 307) |
|  | SEQ ID NO: 8 | $^{215}$SAEHIKPDVVIVLDTAVAGDVP$^{236}$ | 1.212 (aa 224) |
|  | SEQ ID NO: 9 | $^{54}$PKVAVVGHM$^{62}$ | 1.160 (aa 58) |

D. Antigenic Fragments for Flagellins

For flagellins the hypervariable region (approximately aa 200-500) is established in the literature to be antigenic. The highest antigenic fragments of the flagellin peptides of the present invention appear in FIG. 13.

Example 7: The Presence of Antibodies Against Commensal Bacterial Antigens

This example illustrates that detecting the presence or level of bacterial antigen antibody markers in a sample from a subject can be used to determine whether the subject has IBS, e.g., IBS-D or IBS-M (IBS-D/M). The study compared the level of an array of bacterial antigen antibodies such as antibodies against: LaFrc, LaEno, LjEFTu, NOmpA, healthy control samples (n=18) and the sample taken from IBS-D or IBS-M (IBS-D/M) patients (n=22) (FIG. 29A-D).

The example illustrates that the assay method described herein can be used to determine the level of bacterial antigen antibody markers and to aid in the diagnosis of IBS.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

INFORMAL SEQUENCE LISTING

SEQ ID NO: 1
EcEra peptide (position 86-98)
IGDVELVIFVVEG

SEQ ID NO: 2
EcEra peptide (position 116-129)
KAPVILAVNKVDNV

SEQ ID NO: 3
EcEra peptide (position 207-221)
GAELPYSVTVEIERF

SEQ ID NO: 4
EcGabT peptide (position 300-315)
GNPIACVAALEVLKVF

SEQ ID NO: 5
EcGabT peptide (position 49-92)
GIAVLNTGHLHPKVVAAVEAQLKKLSHTCFQVLAYEPYLELCEI SEQ ID NO: 6
EcGabT peptide (position 383-407)
KGLILLSCGPYYNVLRILVPLTIED SEQ ID NO: 7
EcFrvX peptide (position 303-317)
RPVVALCLPTRYLHA SEQ ID NO: 8
EcFrvX peptide (position 215-236)
SAEHIKPDVVIVLDTAVAGDVP SEQ ID NO: 9
EcFrvX peptide (position 54-62)
PKVAVVGHM

---

What is claimed is:

1. A method for aiding in the diagnosis of irritable bowel syndrome (IBS) in a subject, said method comprising:
measuring the level of an array of bacterial antigen antibody markers in a biological sample taken from the subject, wherein the array comprises E. coli FliC;
applying a statistical analysis to the measured level of the array of bacterial antigen antibody markers to generate a bacterial antigen antibody marker profile; and
comparing said bacterial antigen antibody marker profile to a diagnostic model to determine whether the individual has an increased likelihood of having IBS compared to being a healthy control.

2. The method of claim 1, wherein the array of bacterial antigen antibody markers is selected from the group consisting of antibodies against: S. flexneri FliC, C. jejuni FlaA, C. jejuni FlaB, E. coli O157:H7 FliC, E. coli FrvX, E. coli GabT, C. jejuni 81-045, C. jejuni 81-128, and C. jejuni 81-008, E. coli Era, E. coli FocA, E. coli FrvX, E. coli GabT, E. coli YbaN, E. coli YcdG, E. coli YhgN, E. coli YedK, E. coli YidX, L. acidophilus Frc, L. acidophilus Eno, L. johnsonii EFTu, B. fragilis OmpA, Prevotella OmpA, C. perfringens 10bA, C. perfringens SpA, E. faecalis Sant, L. monocytogenes Osp, and combinations thereof.

3. The method of claim 1, wherein the array of bacterial antigen antibody markers is selected from the group consisting of antibodies against: SfFliC, CjFlaA, CjFlaB, EcOFliC, SeFljB, CjGT-A, Cjdmh, CjCgtA and combination thereof.

4. The method of claim 1, wherein the array of bacterial antigen antibody markers is selected from the group consisting of antibodies against: EcFliC, EcEra, EcFocA, EcFrvX, EcGabT, EcYbaN, EcYcdG, EcYhgN, EcYidX, EcYedK, and combinations thereof.

5. The method of claim 1, wherein the array of bacterial antigen antibody markers is selected from the group consisting of antibodies against: LaFrc, LaEno, LjEFTu, BfOmpA, PrOmpA, Cp10bA, CpSpA, EfSant, LmOsp, and combinations thereof.

6. The method of claim 1, wherein the step of measuring the level of an array of bacterial antigen antibody markers comprises:
contacting the sample with at least one bacterial antigen or an antigenic fragment thereof to transform the bacterial antigen antibody present in the sample into a complex comprising the at least one bacterial antigen or the antigenic fragment thereof and the bacterial antigen antibody;
contacting the complex with a detection antibody under conditions suitable to form a ternary complex comprising the at least one bacterial antigen or the antigenic fragment thereof, the bacterial antigen antibody and the detection antibody;
and detecting the ternary complex which correlates to the level of at least one bacterial antigen antibody marker.

7. The method of claim 1, wherein the statistical analysis transforms the level of the array of bacterial antigen antibody markers into a bacterial antigen antibody marker profile.

8. The method of claim 1, wherein the diagnostic model comprises a bacterial antigen antibody model.

9. The method of claim 8, wherein the diagnostic model is established using a retrospective cohort with known outcomes of a clinical subtype of IBS and healthy controls.

10. The method of claim 8, wherein the bacterial antigen antibody model is derived by applying logistic regression analysis to the level of one or more bacterial antigen antibody markers determined in the retrospective cohort.

11. The method of claim 1, wherein (Original) The method further comprises
determining the level of an array of mast cell markers in a biological sample taken from the subject;
applying a statistical analysis to the measured level of the array of mast cell markers to generate a mast cell marker profile; and
comparing said mast cell marker profile to a diagnostic model to determine whether the individual has an increased likelihood of having IBS compared to being a healthy control.

12. The method of claim 11, wherein the array of mast cell markers is selected from the group consisting of β-tryptase, histamine, prostaglandin E2, and combinations thereof.

13. The method of claim 1, wherein (Original) The method further comprises
determining the level of an array of stress factor markers in a biological sample taken from the subject;
applying a statistical analysis to the measured level of the array of stress factor markers to generate a stress factor profile; and
comparing said stress hormone profile to a diagnostic model to determine whether the individual has an increased likelihood of having IBS compared to being a healthy control.

14. The method of claim 13, wherein the array of stress factor markers is selected from the group consisting of cortisol, BDNF, serotonin, CRF, ACTH, and combinations thereof.

15. The method of claim 11, wherein the diagnostic model is established using a retrospective cohort with known outcomes of a clinical subtype of IBS and healthy controls.

16. The method of claim 13, wherein the diagnostic model is established using a retrospective cohort with known outcomes of a clinical subtype of IBS and healthy controls.

17. The method of claim 15, wherein the diagnostic model comprises a bacterial antigen antibody model, a mast cell marker model, a stress factor marker model, or combinations thereof.

18. The method of claim 17, wherein the bacterial antigen antibody model is derived by applying logistic regression analysis to the level of one or more bacterial antigen antibody markers determined in the retrospective cohort.

19. The method of claim 17, wherein the mast cell marker model is derived by applying logistic regression analysis to the level of one or more mast cell markers determined in the retrospective cohort.

20. The method of claim 17, wherein the stress factor marker model is derived by applying logistic regression analysis to the level of one or more stress factor markers determined in the retrospective cohort.

21. The method of claim 17, further comprises classifying a diagnosis of IBS as IBS-constipation (IBS-C), IBS diarrhea (IBS-D), IBS-mixed (IBS-M), IBS-alternating (IBS-A), or post-infectious IBS (IBS-PI).

22. A method for aiding in the diagnosis of irritable bowel syndrome (IBS) in a subject and treating the subject, said method comprising:
    measuring the level of an array of bacterial antigen antibody markers in a biological sample taken from the subject, wherein the array comprises *E. coli* FliC;
    applying a statistical analysis to the measured level of the array of bacterial antigen antibody markers to generate a bacterial antigen antibody marker profile;
    comparing said bacterial antigen antibody marker profile to a diagnostic model to determine whether the individual has an increased likelihood of having IBS compared to being a healthy control; and treating the subject determined to have IBS.

* * * * *

SEQUENCE LISTING

```
<160> NUMBER OF SEQ ID NOS: 23

<210> SEQ ID NO 1
<211> LENGTH: 13
<212> TYPE: PRT
<213> ORGANISM: Artificial Sequence
<220> FEATURE:
<223> OTHER INFORMATION: synthetic Escherichia coli strain K12 Ras-like
      protein GTPase (EcEra, EcERA, era) antigenic fragment, residues
      86-98

<400> SEQUENCE: 1

Ile Gly Asp Val Glu Leu Val Ile Phe Val Val Glu Gly
1               5                   10

<210> SEQ ID NO 2
<211> LENGTH: 14
<212> TYPE: PRT
<213> ORGANISM: Artificial Sequence
<220> FEATURE:
<223> OTHER INFORMATION: synthetic Escherichia coli strain K12 Ras-like
      protein GTPase (EcEra, EcERA, era) antigenic fragment, residues
      115-129

<400> SEQUENCE: 2

Lys Ala Pro Val Ile Leu Ala Val Asn Lys Val Asp Asn Val
1               5                   10

<210> SEQ ID NO 3
<211> LENGTH: 15
<212> TYPE: PRT
<213> ORGANISM: Artificial Sequence
<220> FEATURE:
<223> OTHER INFORMATION: synthetic Escherichia coli strain K12 Ras-like
      protein GTPase (EcEra, EcERA, era) antigenic fragment, residues
      207-221

<400> SEQUENCE: 3

Gly Ala Glu Leu Pro Tyr Ser Val Thr Val Glu Ile Glu Arg Phe
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: synthetic Escherichia coli strain K12 4-
      aminobuutyrate aminotransferase (EcGabT) antigenic fragment,
      residues 300-315
```

-continued

<400> SEQUENCE: 4

Gly Asn Pro Ile Ala Cys Val Ala Ala Leu Glu Val Leu Lys Val Phe
1               5                   10                  15

<210> SEQ ID NO 5
<211> LENGTH: 44
<212> TYPE: PRT
<213> ORGANISM: Artificial Sequence
<220> FEATURE:
<223> OTHER INFORMATION: synthetic Escherichia coli strain K12 4-
      aminobuutyrate aminotransferase (EcGabT) antigenic fragment,
      residues 49-92

<400> SEQUENCE: 5

Gly Ile Ala Val Leu Asn Thr Gly His Leu His Pro Lys Val Val Ala
1               5                   10                  15

Ala Val Glu Ala Gln Leu Lys Lys Leu Ser His Thr Cys Phe Gln Val
                20                  25                  30

Leu Ala Tyr Glu Pro Tyr Leu Glu Leu Cys Glu Ile
            35                  40

<210> SEQ ID NO 6
<211> LENGTH: 25
<212> TYPE: PRT
<213> ORGANISM: Artificial Sequence
<220> FEATURE:
<223> OTHER INFORMATION: synthetic Escherichia coli strain K12 4-
      aminobuutyrate aminotransferase (EcGabT) antigenic fragment,
      residues 383-407

<400> SEQUENCE: 6

Lys Gly Leu Ile Leu Leu Ser Cys Gly Pro Tyr Tyr Asn Val Leu Arg
1               5                   10                  15

Ile Leu Val Pro Leu Thr Ile Glu Asp
                20                  25

<210> SEQ ID NO 7
<211> LENGTH: 15
<212> TYPE: PRT
<213> ORGANISM: Artificial Sequence
<220> FEATURE:
<223> OTHER INFORMATION: synthetic Escherichia coli strain K12 putative
      aminopeptidase (EcFrvX) antigenic fragment, residues 303-317

<400> SEQUENCE: 7

Arg Pro Val Val Ala Leu Cys Leu Pro Thr Arg Tyr Leu His Ala
1               5                   10                  15

<210> SEQ ID NO 8
<211> LENGTH: 22
<212> TYPE: PRT
<213> ORGANISM: Artificial Sequence
<220> FEATURE:
<223> OTHER INFORMATION: synthetic Escherichia coli strain K12 putative
      aminopeptidase (EcFrvX) antigenic fragment, residues 303-317

<400> SEQUENCE: 8

Ser Ala Glu His Ile Lys Pro Asp Val Val Ile Val Leu Asp Thr Ala
1               5                   10                  15

Val Ala Gly Asp Val Pro
            20

<210> SEQ ID NO 9
<211> LENGTH: 9

<212> TYPE: PRT
<213> ORGANISM: Artificial Sequence
<220> FEATURE:
<223> OTHER INFORMATION: synthetic Escherichia coli strain K12 putative
      aminopeptidase (EcFrvX) antigenic fragment, residues 54-62

<400> SEQUENCE: 9

Pro Lys Val Ala Val Val Gly His Met
1               5

<210> SEQ ID NO 10
<211> LENGTH: 460
<212> TYPE: PRT
<213> ORGANISM: Lachnospiraceae sp.
<220> FEATURE:
<221> NAME/KEY: MISC_FEATURE
<222> LOCATION: (1)..(460)
<223> OTHER INFORMATION: Lachnospiraceae bacteria A4 clone 2/04
      flagellin Fla2

<400> SEQUENCE: 10

Met Val Val Gln His Asn Leu Arg Ala Met Asn Ser Asn Arg Met Leu
1               5                   10                  15

Gly Ile Thr Gln Gly Ser Leu Asn Lys Ser Thr Glu Lys Leu Ser Ser
            20                  25                  30

Gly Tyr Lys Val Asn Arg Ala Ala Asp Asp Ala Ala Gly Leu Ser Ile
        35                  40                  45

Ser Glu Lys Met Arg Lys Gln Ile Arg Gly Leu Ser Gln Ala Ser Leu
    50                  55                  60

Asn Ala Glu Asp Gly Ile Ser Ala Val Gln Thr Ala Glu Gly Ala Leu
65                  70                  75                  80

Thr Glu Val His Asp Met Leu Gln Arg Met Asn Glu Leu Ala Val Lys
                85                  90                  95

Ala Ala Asn Gly Thr Asn Ser Thr Ser Asp Arg Gln Thr Ile Gln Asp
            100                 105                 110

Glu Val Asp Gln Leu Leu Thr Glu Ile Asp Arg Val Ala Glu Thr Thr
        115                 120                 125

Lys Phe Asn Glu Leu Tyr Thr Leu Lys Gly Asp Glu Asp Lys Val Thr
    130                 135                 140

Arg Tyr Leu Ser Ala His Asp Ala Gly Ile Glu Gly Thr Leu Thr Gln
145                 150                 155                 160

Gly Ala Thr Asn Ala Thr Phe Ser Met Asp Gln Leu Lys Phe Gly Asp
                165                 170                 175

Thr Ile Met Ile Ala Gly Arg Glu Tyr His Ile Ser Gly Thr Gln Lys
            180                 185                 190

Gln Gln Gly Glu Ile Ile Thr Ser Ser Val Lys Ile Gly Gln Gln Val
        195                 200                 205

Thr Ile Asp Gly Ile Met Tyr Thr Cys Thr Ala Thr Val Ser Asn Ala
    210                 215                 220

Asp Lys Phe Glu Leu Thr Lys Asp Asp Leu Ile Ala Lys Leu Asp Thr
225                 230                 235                 240

Ser Ser Leu Ser Ile Met Ser Val Asn Gly Lys Thr Tyr Tyr Gly Ala
                245                 250                 255

Gly Ile Thr Asp Asp Arg Thr Val Val Ser Ser Ile Gly Ala Tyr Lys
            260                 265                 270

Leu Ile Gln Lys Glu Leu Gly Leu Ala Ser Ser Ile Gly Ala Asp Gly
        275                 280                 285

Ser Thr Gln Ala Ser Val Asn Ala Gly Val Asp Gly Lys Thr Leu Lys

```
                290                 295                 300
Lys Pro Ser Phe Glu Gly Lys Trp Val Phe Ser Ile Asp Lys Gly Ser
305                 310                 315                 320

Val Gln Val Arg Glu Asp Ile Asp Phe Ser Leu His Val Gly Ala Asp
                325                 330                 335

Ala Asp Met Asn Asn Lys Ile Ala Val Lys Ile Gly Ala Leu Asp Thr
            340                 345                 350

Lys Gly Leu Gly Ile Gln Gly Leu Asn Val Lys Asp Thr Thr Gly Ala
        355                 360                 365

Ala Ala Thr Tyr Ala Ile Asp Ser Ile Ala Asp Ala Val Ala Arg Ile
    370                 375                 380

Ser Ala Gln Arg Ser Leu Leu Gly Ala Val Gln Asn Arg Leu Glu His
385                 390                 395                 400

Thr Ile Asn Asn Leu Asp Asn Val Val Glu Asn Thr Thr Ala Ala Glu
                405                 410                 415

Ser Gln Ile Arg Asp Thr Asp Met Ala Thr Glu Met Val Lys Tyr Ser
            420                 425                 430

Asn Asn Asn Val Leu Ala Gln Ala Gly Gln Ser Met Leu Ala Gln Ser
        435                 440                 445

Asn Gln Ala Asn Gln Gly Val Leu Ser Leu Leu Gly
    450                 455                 460

<210> SEQ ID NO 11
<211> LENGTH: 459
<212> TYPE: PRT
<213> ORGANISM: Unknown
<220> FEATURE:
<223> OTHER INFORMATION: unknown mouse cecum uncultured bacterium clone
      Fla-X flagellin FlaX

<400> SEQUENCE: 11

Met Val Val Gln His Asn Leu Arg Ala Met Asn Ser Asn Arg Met Leu
1               5                   10                  15

Gly Ile Thr Gln Gly Ser Leu Asn Lys Ser Thr Glu Lys Leu Ser Ser
            20                  25                  30

Gly Tyr Lys Val Asn Arg Ala Ala Asp Ala Ala Gly Leu Ser Ile
        35                  40                  45

Ser Glu Lys Met Arg Lys Gln Ile Arg Gly Leu Ser Gln Ala Ser Leu
50                  55                  60

Asn Ala Glu Asp Gly Ile Ser Ala Val Gln Thr Ala Glu Gly Ala Leu
65                  70                  75                  80

Thr Glu Val His Asp Met Leu Gln Arg Met Asn Glu Leu Ala Val Lys
                85                  90                  95

Ala Ala Asn Gly Thr Asn Ser Thr Ser Asp Arg Gln Thr Ile Gln Asp
            100                 105                 110

Glu Val Asp Gln Leu Leu Thr Glu Ile Asp Arg Val Ala Glu Thr Thr
        115                 120                 125

Lys Phe Asn Glu Leu Tyr Thr Leu Lys Gly Asp Glu Asp Lys Val Thr
    130                 135                 140

Arg Tyr Leu Ser Ala His Asp Ala Gly Ile Glu Gly Thr Leu Thr Gln
145                 150                 155                 160

Gly Ala Thr Asn Ala Thr Phe Ser Met Asp Gln Leu Lys Phe Gly Asp
                165                 170                 175

Thr Ile Met Ile Ala Gly Arg Glu Tyr His Ile Ser Gly Thr Lys Ala
            180                 185                 190
```

```
Glu Gln Ala Ala Ile Ile Thr Ala Ser Val Lys Ile Gly Gln Gln Val
            195                 200                 205

Thr Ile Asp Gly Ile Met Tyr Thr Cys Ser Ser Val Ser Asn Ala Asp
    210                 215                 220

Lys Phe Glu Leu Lys Ser Glu Asp Leu Ile Ala Lys Leu Asp Thr Ser
225                 230                 235                 240

Ser Leu Ser Ile Met Ser Val Asn Gly Lys Thr Tyr Tyr Gly Ala Gly
                245                 250                 255

Ile Thr Asp Asp Arg Thr Val Val Ser Ile Gly Ala Tyr Lys Leu
            260                 265                 270

Ile Gln Lys Glu Leu Gly Leu Ala Ser Ser Ile Gly Ala Asp Gly Ala
            275                 280                 285

Thr Gln Ala Ser Val Asn Ala Gly Val Asp Gly Lys Thr Leu Met Lys
    290                 295                 300

Pro Ser Phe Glu Gly Lys Trp Val Phe Ser Ile Asp Lys Gly Ser Val
305                 310                 315                 320

Gln Val Arg Glu Asp Ile Asp Phe Ser Leu His Val Gly Ala Asp Ala
                325                 330                 335

Asp Met Asn Asn Lys Ile Ala Val Lys Ile Gly Ala Leu Asp Thr Lys
            340                 345                 350

Gly Leu Gly Ile Gln Gly Leu Asn Val Lys Asp Thr Thr Gly Ala Ala
        355                 360                 365

Ala Thr Tyr Ala Ile Asp Ser Ile Ala Asp Ala Val Ala Arg Ile Ser
    370                 375                 380

Ala Gln Arg Ser Leu Leu Gly Ala Val Gln Asn Arg Leu Glu His Thr
385                 390                 395                 400

Ile Asn Asn Leu Asp Asn Val Val Glu Asn Thr Thr Ala Ala Glu Ser
                405                 410                 415

Gln Ile Arg Asp Thr Asp Met Ala Thr Glu Met Val Lys Tyr Ser Asn
            420                 425                 430

Asn Asn Val Leu Ala Gln Ala Gly Gln Ser Met Leu Ala Gln Ser Asn
            435                 440                 445

Gln Ala Asn Gln Gly Val Leu Gln Leu Leu Gln
        450                 455

<210> SEQ ID NO 12
<211> LENGTH: 493
<212> TYPE: PRT
<213> ORGANISM: Unknown
<220> FEATURE:
<223> OTHER INFORMATION: unknown mouse cecum uncultured bacterium clone
      CBir-1 flagellin CBir1

<400> SEQUENCE: 12

Met Val Val Gln His Asn Leu Gln Ala Met Asn Ser Asn Arg Met Leu
1               5                   10                  15

Gly Ile Thr Gln Lys Thr Ala Ser Lys Ser Thr Glu Lys Leu Ser Ser
            20                  25                  30

Gly Tyr Ala Ile Asn Arg Ala Ala Asp Asn Ala Ala Gly Leu Ala Ile
        35                  40                  45

Ser Glu Lys Met Arg Lys Gln Ile Arg Gly Leu Thr Gln Ala Ser Thr
    50                  55                  60

Asn Ala Glu Asp Gly Ile Ser Ser Val Gln Thr Ala Glu Gly Ala Leu
65              70                  75                  80

Thr Glu Val His Asp Met Leu Gln Arg Met Asn Glu Leu Ala Ile Gln
                85                  90                  95
```

```
Ala Ala Asn Gly Thr Asn Ser Glu Asp Asp Arg Ser Tyr Ile Gln Asp
            100                 105                 110

Glu Ile Asp Gln Leu Thr Gln Glu Ile Asp Arg Val Ala Glu Thr Thr
        115                 120                 125

Lys Phe Asn Glu Thr Tyr Leu Leu Lys Gly Asp Thr Lys Asn Val Asp
    130                 135                 140

Ala Met Asp Tyr Thr Tyr Ser Tyr Lys Ala Val Thr Thr Asn Thr Val
145                 150                 155                 160

Ala Arg Ala Ser Val Leu Ala Ala Glu Asn Thr Ala Thr Gly Met Ser
                165                 170                 175

Val Ser Ile Ser Phe Ala Ala Asn Ser Gly Lys Val Thr Ala Ala Asp
            180                 185                 190

Ser Asn Asn Leu Ala Lys Ala Ile Arg Asp Gln Gly Phe Thr Ile Thr
        195                 200                 205

Thr Ser Thr Gln Asn Gly Lys Val Val Tyr Gly Leu Glu Leu Asn Gly
    210                 215                 220

Ser Asp Ala Lys Ala Asn Tyr Thr Val Ser Thr Val Ser Met Glu Ala
225                 230                 235                 240

Gly Thr Phe Lys Ile Leu Asn Ser Asn Lys Gln Val Val Ala Ser Val
                245                 250                 255

Thr Ile Ser Thr Thr Ala Ser Phe Lys Lys Val Ser Gly Met Ser Gln
            260                 265                 270

Ile Val Thr Ala Tyr Ser Val Ser Ala Ala Tyr Ala Thr Gly Asp Val
        275                 280                 285

Tyr Ser Leu Tyr Asp Ala Asp Gly Asn Ala Ile Ser Ala Asn Lys Leu
    290                 295                 300

Asp Lys Tyr Phe Thr Ala Gly Gly Ala Thr Glu Ala Gly Gly Ile Ala
305                 310                 315                 320

Thr Thr Leu Ser Ala Asn Ser Gly Val Pro Lys Val Tyr Asp Val Leu
                325                 330                 335

Gly Lys Glu Val Ser Ala Val Ser Ile Ala Ser Thr Leu Val Thr Ala
            340                 345                 350

Val Lys Asp Lys Thr Ala Ala Leu Lys Met Asn Phe His Val Gly Ala
        355                 360                 365

Asp Gly Thr Asp Asn Asn Lys Ile Lys Ile Asn Ile Glu Ala Met Thr
370                 375                 380

Ala Lys Ser Leu Gly Val Asn Gly Leu Lys Val Ser Gly Ser Ser Gly
385                 390                 395                 400

Thr Asn Ala Thr Asn Ala Ile Glu Ile Ile Ala Gly Ala Ile Lys Lys
                405                 410                 415

Val Ser Thr Gln Arg Ser Ala Leu Gly Ala Val Gln Asn Arg Leu Glu
            420                 425                 430

His Thr Ile Asn Asn Leu Asp Asn Ile Val Glu Asn Thr Thr Ala Ala
        435                 440                 445

Glu Ser Gly Ile Arg Asp Thr Asp Met Ala Thr Glu Met Val Lys Tyr
    450                 455                 460

Ser Asn Ala Asn Ile Leu Ser Gln Ala Gly Gln Ser Met Leu Ala Gln
465                 470                 475                 480

Ser Asn Gln Ser Asn Gln Gly Val Leu Gln Leu Leu Gln
                485                 490

<210> SEQ ID NO 13
<211> LENGTH: 550
```

```
<212> TYPE: PRT
<213> ORGANISM: Shigella flexneri
<220> FEATURE:
<221> NAME/KEY: MISC_FEATURE
<222> LOCATION: (1)..(550)
<223> OTHER INFORMATION: flagellin FliC (SfFliC, fliC)

<400> SEQUENCE: 13
```

| Met

```
                 370                 375                 380
Val Asp Phe Thr Thr Ala Gly Tyr Ser Val Asn Gly Thr Thr Gly Ala
385                 390                 395                 400

Val Thr Lys Gly Val Asp Ser Val Tyr Val Asp Asn Asn Glu Ala Leu
                405                 410                 415

Thr Thr Ser Asp Thr Val Asp Phe Tyr Leu Gln Asp Asp Gly Ser Val
                420                 425                 430

Thr Asn Gly Ser Gly Lys Ala Val Tyr Lys Asp Ala Asp Gly Lys Leu
                435                 440                 445

Thr Thr Asp Ala Glu Thr Lys Ala Ala Thr Thr Ala Asp Pro Leu Lys
                450                 455                 460

Ala Leu Asp Glu Ala Ile Ser Ser Ile Asp Lys Phe Arg Ser Ser Leu
465                 470                 475                 480

Gly Ala Val Gln Asn Arg Leu Asp Ser Ala Val Thr Asn Leu Asn Asn
                485                 490                 495

Thr Thr Thr Asn Leu Ser Glu Ala Gln Ser Arg Ile Gln Asp Ala Asp
                500                 505                 510

Tyr Ala Thr Glu Val Ser Asn Met Ser Lys Ala Gln Ile Ile Gln Gln
                515                 520                 525

Ala Gly Asn Ser Val Leu Ala Lys Ala Asn Gln Val Pro Gln Gln Val
                530                 535                 540

Leu Ser Leu Leu Gln Gly
545                 550

<210> SEQ ID NO 14
<211> LENGTH: 585
<212> TYPE: PRT
<213> ORGANISM: Escherichia coli
<220> FEATURE:
<221> NAME/KEY: MISC_FEATURE
<222> LOCATION: (1)..(585)
<223> OTHER INFORMATION: Escherichia coli strain K12 flagellin FliC
      (EcFliC, fliC)

<400> SEQUENCE: 14

Met Ala Gln Val Ile Asn Thr Asn Ser Leu Ser Leu Ile Thr Gln Asn
1               5                   10                  15

Asn Ile Asn Lys Asn Gln Ser Ala Leu Ser Ser Ser Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ser Asn Ile Lys Gly Leu Thr Gln Ala
50              55                  60

Ala Arg Asn Ala Asn Asp Gly Ile Ser Val Ala Gln Thr Thr Glu Gly
65              70                  75                  80

Ala Leu Ser Glu Ile Asn Asn Asn Leu Gln Arg Ile Arg Glu Leu Thr
                85                  90                  95

Val Gln Ala Thr Thr Gly Thr Asn Ser Asp Ser Asp Leu Asp Ser Ile
                100                 105                 110

Gln Asp Glu Ile Lys Ser Arg Leu Asp Glu Ile Asp Arg Val Ser Gly
            115                 120                 125

Gln Thr Gln Phe Asn Gly Val Asn Val Leu Ala Lys Asp Gly Ser Met
            130                 135                 140

Lys Ile Gln Val Gly Ala Asn Asp Gly Glu Thr Ile Thr Ile Asp Leu
145                 150                 155                 160

Lys Lys Ile Asp Ser Asp Thr Leu Gly Leu Asn Gly Phe Asn Val Asn
```

-continued

```
                165                 170                 175
Gly Lys Gly Thr Ile Thr Asn Lys Ala Ala Thr Val Ser Asp Leu Thr
            180                 185                 190

Ser Ala Gly Ala Lys Leu Asn Thr Thr Thr Gly Leu Tyr Asp Leu Lys
        195                 200                 205

Thr Glu Asn Thr Leu Leu Thr Thr Asp Ala Ala Phe Asp Lys Leu Gly
    210                 215                 220

Asn Gly Asp Lys Val Thr Val Gly Gly Val Asp Tyr Thr Tyr Asn Ala
225                 230                 235                 240

Lys Ser Gly Asp Phe Thr Thr Thr Lys Ser Thr Ala Gly Thr Gly Val
                245                 250                 255

Asp Ala Ala Ala Gln Ala Ala Asp Ser Ala Ser Lys Arg Asp Ala Leu
            260                 265                 270

Ala Ala Thr Leu His Ala Asp Val Gly Lys Ser Val Asn Gly Ser Tyr
        275                 280                 285

Thr Thr Lys Asp Gly Thr Val Ser Phe Glu Thr Asp Ser Ala Gly Asn
    290                 295                 300

Ile Thr Ile Gly Gly Ser Gln Ala Tyr Val Asp Asp Ala Gly Asn Leu
305                 310                 315                 320

Thr Thr Asn Asn Ala Gly Ser Ala Ala Lys Ala Asp Met Lys Ala Leu
                325                 330                 335

Leu Lys Ala Ala Ser Glu Gly Ser Asp Gly Ala Ser Leu Thr Phe Asn
            340                 345                 350

Gly Thr Glu Tyr Thr Ile Ala Lys Ala Thr Pro Ala Thr Thr Pro
        355                 360                 365

Val Ala Pro Leu Ile Pro Gly Ile Thr Tyr Gln Ala Thr Val Ser
    370                 375                 380

Lys Asp Val Val Leu Ser Glu Thr Lys Ala Ala Ala Thr Ser Ser
385                 390                 395                 400

Ile Thr Phe Asn Ser Gly Val Leu Ser Lys Thr Ile Gly Phe Thr Ala
                405                 410                 415

Gly Glu Ser Ser Asp Ala Ala Lys Ser Tyr Val Asp Lys Gly Gly
            420                 425                 430

Ile Thr Asn Val Ala Asp Tyr Thr Val Ser Tyr Ser Val Asn Lys Asp
        435                 440                 445

Asn Gly Ser Val Thr Val Ala Gly Tyr Ala Ser Ala Thr Asp Thr Asn
    450                 455                 460

Lys Asp Tyr Ala Pro Ala Ile Gly Thr Ala Val Asn Val Asn Ser Ala
465                 470                 475                 480

Gly Lys Ile Thr Thr Glu Thr Thr Ser Ala Gly Ser Ala Thr Thr Asn
                485                 490                 495

Pro Leu Ala Ala Leu Asp Asp Ala Ile Ser Ser Ile Asp Lys Phe Arg
            500                 505                 510

Ser Ser Leu Gly Ala Ile Gln Asn Arg Leu Asp Ser Ala Val Thr Asn
        515                 520                 525

Leu Asn Asn Thr Thr Thr Asn Leu Ser Glu Ala Gln Ser Arg Ile Gln
    530                 535                 540

Asp Ala Asp Tyr Ala Thr Glu Val Ser Asn Met Ser Lys Ala Gln Ile
545                 550                 555                 560

Ile Gln Gln Ala Gly Asn Ser Val Leu Ala Lys Ala Asn Gln Val Pro
                565                 570                 575

Gln Gln Val Leu Ser Leu Leu Gln Gly
            580                 585
```

<210> SEQ ID NO 15
<211> LENGTH: 504
<212> TYPE: PRT
<213> ORGANISM: Salmonella enteritidis
<220> FEATURE:
<221> NAME/KEY: MISC_FEATURE
<222> LOCATION: (1)..(504)
<223> OTHER INFORMATION: phase-1 flagellin FliC (fliC)

<400> SEQUENCE: 15

```
Ala Gln Val Ile Asn Thr Asn Ser Leu Ser Leu Leu Thr Gln Asn Asn
1               5                   10                  15

Leu Asn Lys Ser Gln Ser Ser Leu Ser Ser Ala Ile Glu Arg Leu Ser
            20                  25                  30

Ser Gly Leu Arg Ile Asn Ser Ala Lys Asp Asp Ala Ala Gly Gln Ala
        35                  40                  45

Ile Ala Asn Arg Phe Thr Ser Asn Ile Lys Gly Leu Thr Gln Ala Ser
    50                  55                  60

Arg Asn Ala Asn Asp Gly Ile Ser Ile Ala Gln Thr Thr Glu Gly Ala
65                  70                  75                  80

Leu Asn Glu Ile Asn Asn Asn Leu Gln Arg Val Arg Glu Leu Ser Val
                85                  90                  95

Gln Ala Thr Asn Gly Thr Asn Ser Asp Ser Asp Leu Lys Ser Ile Gln
            100                 105                 110

Asp Glu Ile Gln Gln Arg Leu Glu Glu Ile Asp Arg Val Ser Asn Gln
        115                 120                 125

Thr Gln Phe Asn Gly Val Lys Val Leu Ser Gln Asp Asn Gln Met Lys
130                 135                 140

Ile Gln Val Gly Ala Asn Asp Gly Glu Thr Ile Thr Ile Asp Leu Gln
145                 150                 155                 160

Lys Ile Asp Val Lys Ser Leu Gly Leu Asp Gly Phe Asn Val Asn Gly
                165                 170                 175

Pro Lys Glu Ala Thr Val Gly Asp Leu Lys Ser Ser Phe Lys Asn Val
            180                 185                 190

Thr Gly Tyr Asp Thr Tyr Ala Ala Gly Ala Asp Lys Tyr Arg Val Asp
        195                 200                 205

Ile Asn Ser Gly Ala Val Val Thr Asp Ala Ala Pro Asp Lys Val
    210                 215                 220

Tyr Val Asn Ala Ala Asn Gly Gln Leu Thr Thr Asp Asp Ala Glu Asn
225                 230                 235                 240

Asn Thr Ala Val Asp Leu Phe Lys Thr Thr Lys Ser Thr Ala Gly Thr
                245                 250                 255

Ala Glu Ala Lys Ala Ile Ala Gly Ala Ile Lys Gly Gly Lys Glu Gly
            260                 265                 270

Asp Thr Phe Asp Tyr Lys Gly Val Thr Phe Thr Ile Asp Thr Lys Thr
        275                 280                 285

Gly Asp Asp Gly Asn Gly Lys Val Ser Thr Thr Ile Asn Gly Glu Lys
    290                 295                 300

Val Thr Leu Thr Val Ala Asp Ile Ala Thr Gly Ala Thr Asp Val Asn
305                 310                 315                 320

Ala Ala Thr Leu Gln Ser Ser Lys Asn Val Tyr Thr Ser Val Val Asn
                325                 330                 335

Gly Gln Phe Thr Phe Asp Asp Lys Thr Lys Asn Glu Ser Ala Lys Leu
            340                 345                 350
```

Ser Asp Leu Glu Ala Asn Asn Ala Val Lys Gly Glu Ser Lys Ile Thr
            355                 360                 365

Val Asn Gly Ala Glu Tyr Thr Ala Asn Ala Thr Gly Asp Lys Ile Thr
370                 375                 380

Leu Ala Gly Lys Thr Met Phe Ile Asp Lys Thr Ala Ser Gly Val Ser
385                 390                 395                 400

Thr Leu Ile Asn Glu Asp Ala Ala Ala Lys Lys Ser Thr Ala Asn
            405                 410                 415

Pro Leu Ala Ser Ile Asp Ser Ala Leu Ser Lys Val Asp Ala Val Arg
                420                 425                 430

Ser Ser Leu Gly Ala Ile Gln Asn Arg Phe Asp Ser Ala Ile Thr Asn
            435                 440                 445

Leu Gly Asn Thr Val Thr Asn Leu Asn Ser Ala Arg Ser Arg Ile Glu
            450                 455                 460

Asp Ala Asp Tyr Ala Thr Glu Val Ser Asn Met Ser Lys Ala Gln Ile
465                 470                 475                 480

Leu Gln Gln Ala Gly Thr Ser Val Leu Ala Gln Ala Asn Gln Val Pro
                485                 490                 495

Gln Asn Val Leu Ser Leu Leu Arg
            500

<210> SEQ ID NO 16
<211> LENGTH: 505
<212> TYPE: PRT
<213> ORGANISM: Salmonella enteritidis
<220> FEATURE:
<221> NAME/KEY: MISC_FEATURE
<222> LOCATION: (1)..(505)
<223> OTHER INFORMATION: Salmonella enteritidis PT4 strain P125109
      flagellin FljB (SeFljB, fljB)

<400> SEQUENCE: 16

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
    130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Gly Pro Lys Glu Ala Thr Val Gly Asp Leu Lys Ser Ser Phe Lys Asn
            180                 185                 190

```
Val Thr Gly Tyr Asp Thr Tyr Ala Ala Gly Ala Asp Lys Tyr Arg Val
            195                 200                 205

Asp Ile Asn Ser Gly Ala Val Val Thr Asp Ala Ala Pro Asp Lys
    210                 215                 220

Val Tyr Val Asn Ala Ala Asn Gly Gln Leu Thr Thr Asp Asp Ala Glu
225                 230                 235                 240

Asn Asn Thr Ala Val Asp Leu Phe Lys Thr Thr Lys Ser Thr Ala Gly
                245                 250                 255

Thr Ala Glu Ala Lys Ala Ile Ala Gly Ala Ile Lys Gly Gly Lys Glu
            260                 265                 270

Gly Asp Thr Phe Asp Tyr Lys Gly Val Thr Phe Thr Ile Asp Thr Lys
            275                 280                 285

Thr Gly Asp Asp Gly Asn Gly Lys Val Ser Thr Ile Asn Gly Glu
    290                 295                 300

Lys Val Thr Leu Thr Val Ala Asp Ile Ala Thr Gly Ala Thr Asp Val
305                 310                 315                 320

Asn Ala Ala Thr Leu Gln Ser Ser Lys Asn Val Tyr Thr Ser Val Val
                325                 330                 335

Asn Gly Gln Phe Thr Phe Asp Asp Lys Thr Lys Asn Glu Ser Ala Lys
            340                 345                 350

Leu Ser Asp Leu Glu Ala Asn Asn Ala Val Lys Gly Glu Ser Lys Ile
        355                 360                 365

Thr Val Asn Gly Ala Glu Tyr Thr Ala Asn Ala Thr Gly Asp Lys Ile
    370                 375                 380

Thr Leu Ala Gly Lys Thr Met Phe Ile Asp Lys Thr Ala Ser Gly Val
385                 390                 395                 400

Ser Thr Leu Ile Asn Glu Asp Ala Ala Ala Lys Lys Ser Thr Ala
                405                 410                 415

Asn Pro Leu Ala Ser Ile Asp Ser Ala Leu Ser Lys Val Asp Ala Val
            420                 425                 430

Arg Ser Ser Leu Gly Ala Ile Gln Asn Arg Phe Asp Ser Ala Ile Thr
        435                 440                 445

Asn Leu Gly Asn Thr Val Thr Asn Leu Asn Ser Ala Arg Ser Arg Ile
    450                 455                 460

Glu Asp Ala Asp Tyr Ala Thr Glu Val Ser Asn Met Ser Lys Ala Gln
465                 470                 475                 480

Ile Leu Gln Gln Ala Gly Thr Ser Val Leu Ala Gln Ala Asn Gln Val
                485                 490                 495

Pro Gln Asn Val Leu Ser Leu Leu Arg
            500                 505

<210> SEQ ID NO 17
<211> LENGTH: 576
<212> TYPE: PRT
<213> ORGANISM: Campylobacter jejuni
<220> FEATURE:
<221> NAME/KEY: MISC_FEATURE
<222> LOCATION: (1)..(576)
<223> OTHER INFORMATION: Campylobacter jejuni subspecies jejuni strain
      81-176 serotype O:23/36 flagellin FlaA (flaA)

<400> SEQUENCE: 17

Met Gly Phe Arg Ile Asn Thr Asn Val Ala Ala Leu Asn Ala Lys Ala
1               5                   10                  15

Asn Ser Asp Leu Asn Ala Lys Ser Leu Asp Ala Ser Leu Ser Arg Leu
            20                  25                  30
```

```
Ser Ser Gly Leu Arg Ile Asn Ser Ala Ala Asp Asp Ala Ser Gly Met
         35                  40                  45

Ala Ile Ala Asp Ser Leu Arg Ser Gln Ala Asn Thr Leu Gly Gln Ala
 50                  55                  60

Ile Ser Asn Gly Asn Asp Ala Leu Gly Ile Leu Gln Thr Ala Asp Lys
 65                  70                  75                  80

Ala Met Asp Glu Gln Leu Lys Ile Leu Asp Thr Ile Lys Thr Lys Ala
                 85                  90                  95

Thr Gln Ala Ala Gln Asp Gly Gln Ser Leu Lys Thr Arg Thr Met Leu
                100                 105                 110

Gln Ala Asp Ile Asn Lys Leu Met Glu Glu Leu Asp Asn Ile Ala Asn
                115                 120                 125

Thr Thr Ser Phe Asn Gly Lys Gln Leu Leu Ser Gly Asn Phe Thr Asn
130                 135                 140

Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Val Thr Arg Phe Glu Thr
                165                 170                 175

Gly Ala Gln Ser Phe Thr Ser Gly Val Val Gly Leu Thr Ile Lys Asn
                180                 185                 190

Tyr Asn Gly Ile Glu Asp Phe Lys Phe Asp Asn Val Val Ile Ser Thr
                195                 200                 205

Ser Val Gly Thr Gly Leu Gly Ala Leu Ala Glu Glu Ile Asn Lys Ser
                210                 215                 220

Ala Asp Lys Thr Gly Val Arg Ala Thr Tyr Asp Val Lys Thr Thr Gly
225                 230                 235                 240

Val Tyr Ala Ile Lys Glu Gly Thr Thr Ser Gln Glu Phe Ala Ile Asn
                245                 250                 255

Gly Val Thr Ile Gly Lys Ile Glu Tyr Lys Asp Gly Asp Gly Asn Gly
                260                 265                 270

Ser Leu Ile Ser Ala Ile Asn Ala Val Lys Asp Thr Thr Gly Val Gln
                275                 280                 285

Ala Ser Lys Asp Glu Asn Gly Lys Leu Val Leu Thr Ser Ala Asp Gly
290                 295                 300

Arg Gly Ile Lys Ile Thr Gly Asp Ile Gly Val Gly Ser Gly Ile Leu
305                 310                 315                 320

Ala Asn Gln Lys Glu Asn Tyr Gly Arg Leu Ser Leu Val Lys Asn Asp
                325                 330                 335

Gly Arg Asp Ile Asn Ile Ser Gly Thr Asn Leu Ser Ala Ile Gly Met
                340                 345                 350

Gly Thr Thr Asp Met Ile Ser Gln Ser Ser Val Ser Leu Arg Glu Ser
                355                 360                 365

Lys Gly Gln Ile Ser Ala Thr Asn Ala Asp Ala Met Gly Phe Asn Ser
                370                 375                 380

Tyr Lys Gly Gly Lys Phe Val Phe Thr Gln Asn Val Ser Ser Ile
385                 390                 395                 400

Ser Ala Phe Met Ser Ala Gln Gly Ser Gly Phe Ser Arg Gly Ser Gly
                405                 410                 415

Phe Ser Val Gly Ser Gly Lys Asn Leu Ser Val Gly Leu Ser Gln Gly
                420                 425                 430

Ile Gln Ile Ile Ser Ser Ala Ala Ser Met Ser Asn Thr Tyr Val Val
                435                 440                 445

Ser Ala Gly Ser Gly Phe Ser Ser Gly Ser Gly Asn Ser Gln Phe Ala
```

```
                450             455             460
Ala Leu Lys Thr Thr Ala Ala Asn Thr Thr Asp Glu Thr Ala Gly Val
465                 470                 475                 480

Thr Thr Leu Lys Gly Ala Met Ala Val Met Asp Ile Ala Glu Thr Ala
                485                 490                 495

Ile Thr Asn Leu Asp Gln Ile Arg Ala Asp Ile Gly Ser Ile Gln Asn
            500                 505                 510

Gln Val Thr Ser Thr Ile Asn Asn Ile Thr Val Thr Gln Val Asn Val
        515                 520                 525

Lys Ala Ala Glu Ser Gln Ile Arg Asp Val Asp Phe Ala Ser Glu Ser
530                 535                 540

Ala Asn Tyr Ser Lys Ala Asn Ile Leu Ala Gln Ser Gly Ser Tyr Ala
545                 550                 555                 560

Met Ala Gln Ala Asn Ser Ser Gln Gln Asn Val Leu Arg Leu Leu Gln
                565                 570                 575

<210> SEQ ID NO 18
<211> LENGTH: 576
<212> TYPE: PRT
<213> ORGANISM: Campylobacter jejuni
<220> FEATURE:
<221> NAME/KEY: MISC_FEATURE
<222> LOCATION: (1)..(576)
<223> OTHER INFORMATION: Campylobacter jejuni subspecies jejuni strain
      81-176 serotype O:23/36 flagellin FlaB (flaB)

<400> SEQUENCE: 18

Met Gly Phe Arg Ile Asn Thr Asn Ile Gly Ala Leu Asn Ala His Ala
1               5                   10                  15

Asn Ser Val Val Asn Ser Asn Glu Leu Asp Lys Ser Leu Ser Arg Leu
            20                  25                  30

Ser Ser Gly Leu Arg Ile Asn Ser Ala Ala Asp Asp Ala Ser Gly Met
        35                  40                  45

Ala Ile Ala Asp Ser Leu Arg Ser Gln Ala Ala Thr Leu Gly Gln Ala
    50                  55                  60

Ile Asn Asn Gly Asn Asp Ala Ile Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Lys Leu Met Glu Glu Leu Asp Asn Ile Ala Asn
        115                 120                 125

Thr Thr Ser Phe Asn Gly Lys Gln Leu Leu Ser Gly Asn Phe Thr Asn
    130                 135                 140

Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Val Thr Arg Phe Glu Thr
                165                 170                 175

Gly Ala Gln Ser Phe Thr Ser Gly Val Val Gly Leu Thr Ile Lys Asn
            180                 185                 190

Tyr Asn Gly Ile Glu Asp Phe Lys Phe Asp Asn Val Val Ile Ser Thr
        195                 200                 205

Ser Val Gly Thr Gly Leu Gly Ala Leu Ala Glu Glu Ile Asn Lys Ser
    210                 215                 220

Ala Asp Lys Thr Gly Val Arg Ala Thr Tyr Asp Val Lys Thr Thr Gly
```

```
        225                 230                 235                 240
Val Tyr Ala Ile Lys Glu Gly Thr Thr Ser Gln Asp Phe Ala Ile Asn
                    245                 250                 255
Gly Val Val Ile Gly Gln Ile Asn Tyr Lys Asp Gly Asp Asn Asn Gly
                    260                 265                 270
Gln Leu Val Ser Ala Ile Asn Ala Val Lys Asp Thr Thr Gly Val Gln
                    275                 280                 285
Ala Ser Lys Asp Glu Asn Gly Lys Leu Val Leu Thr Ser Ala Asp Gly
            290                 295                 300
Arg Gly Ile Lys Ile Thr Gly Asp Ile Gly Val Gly Ser Gly Ile Leu
305                 310                 315                 320
Ala Asn Gln Lys Glu Asn Tyr Gly Arg Leu Ser Leu Val Lys Asn Asp
                    325                 330                 335
Gly Arg Asp Ile Asn Ile Ser Gly Thr Asn Leu Ser Ala Ile Gly Met
                    340                 345                 350
Gly Thr Thr Asp Met Ile Ser Gln Ser Ser Val Ser Leu Arg Glu Ser
                    355                 360                 365
Lys Gly Gln Ile Ser Ala Thr Asn Ala Asp Ala Met Gly Phe Asn Ser
            370                 375                 380
Tyr Lys Gly Gly Gly Lys Phe Val Phe Thr Gln Asn Val Ser Ser Ile
385                 390                 395                 400
Ser Ala Phe Met Ser Ala Gln Gly Ser Gly Phe Ser Arg Gly Ser Gly
                    405                 410                 415
Phe Ser Val Gly Ser Gly Lys Asn Leu Ser Val Gly Leu Ser Gln Gly
                    420                 425                 430
Ile Gln Ile Ile Ser Ser Ala Ala Ser Met Ser Asn Thr Tyr Val Val
                    435                 440                 445
Ser Ala Gly Ser Gly Phe Ser Ser Gly Ser Gly Asn Ser Gln Phe Ala
            450                 455                 460
Ala Leu Lys Thr Thr Ala Ala Asn Thr Thr Asp Glu Thr Ala Gly Val
465                 470                 475                 480
Thr Thr Leu Lys Gly Ala Met Ala Val Met Asp Ile Ala Glu Thr Ala
                    485                 490                 495
Ile Thr Asn Leu Asp Gln Ile Arg Ala Asp Ile Gly Ser Val Gln Asn
                    500                 505                 510
Gln Leu Gln Val Thr Ile Asn Asn Ile Thr Val Thr Gln Val Asn Val
                    515                 520                 525
Lys Ala Ala Glu Ser Thr Ile Arg Asp Val Asp Phe Ala Ser Glu Ser
            530                 535                 540
Ala Asn Phe Ser Lys Tyr Asn Ile Leu Ala Gln Ser Gly Ser Tyr Ala
545                 550                 555                 560
Met Ser Gln Ala Asn Ala Val Gln Gln Asn Val Leu Lys Leu Leu Gln
                    565                 570                 575

<210> SEQ ID NO 19
<211> LENGTH: 615
<212> TYPE: PRT
<213> ORGANISM: Artificial Sequence
<220> FEATURE:
<223> OTHER INFORMATION: synthetic consensus flagellin sequence from
      inflammatory bowel disease (IBD) bacteria

<400> SEQUENCE: 19

Met Ala Gln Val Ile Asn Thr Asn Ser Leu Ala Leu Asn Thr Gln Asn
1               5                   10                  15
```

```
Asn Leu Asn Lys Asn Gln Ser Ser Leu Ser Lys Ser Ile Glu Arg Leu
             20                  25                  30
Ser Ser Gly Leu Arg Ile Asn Ser Ala Ala Asp Asp Ala Ala Gly Gln
         35                  40                  45
Ala Ile Ala Asn Arg Phe Arg Ser Gln Ile Lys Gly Leu Thr Gln Ala
     50                  55                  60
Ser Arg Asn Ala Asn Asp Gly Ile Ser Ile Ala Gln Thr Ala Glu Gly
65                  70                  75                  80
Ala Leu Thr Glu Ile Asn Asn Asn Leu Gln Arg Ile Arg Glu Leu Ala
                 85                  90                  95
Val Gln Ala Ala Asn Gly Thr Asn Ser Asp Ser Asp Arg Asp Ser Ile
             100                 105                 110
Gln Asp Glu Ile Asp Gln Leu Leu Glu Glu Ile Asp Arg Val Ala Asn
         115                 120                 125
Thr Thr Gln Phe Asn Gly Val Tyr Val Leu Ser Gly Asn Asp Thr Asp
130                 135                 140
Met Lys Ile Gln Val Gly Ala Asn Asp Gly Glu Thr Ile Thr Ile Asp
145                 150                 155                 160
Leu Thr Lys Ile Asp Ser Ser Lys Leu Gly Leu Thr Gly Phe Asn Val
                 165                 170                 175
Asn Gly Asp Gly Phe Ile Ser Phe Lys Ala Ala Thr Val Ile Asp Leu
             180                 185                 190
Ala Ser Ala Glu Ala Asn Val Lys Phe Asp Asn Val Val Ile Ser Thr
         195                 200                 205
Ser Val Gly Thr Gly Tyr Asp Ala Lys Ala Glu Gln Ile Leu Lys Ser
210                 215                 220
Ala Asp Lys Thr Gly Asp Ile Ala Thr Ala Asp Val Lys Asn Gly Gly
225                 230                 235                 240
Val Ala Val Val Thr Asp Gly Ala Thr Asp Gly Lys Phe Ala Ile Asn
                 245                 250                 255
Ala Tyr Thr Cys Ser Leu Thr Thr Ser Asp Ala Gly Asp Phe Glu Gly
             260                 265                 270
Ala Leu Ala Ser Ala Ala Asp Ser Ala Ser Lys Arg Asp Ala Leu Lys
         275                 280                 285
Asp Thr Thr Gly Val Ile Ala Gly Lys Asp Glu Asn Gly Ala Ile Ala
290                 295                 300
Gly Ala Ile Lys Asp Gly Met Ser Gly Asp Gly Thr Asp Tyr Ile Gly
305                 310                 315                 320
Ala Gly Thr Phe Asp Asp Gly Thr Lys Lys Ser Asp Asp Gly Ala Gly
                 325                 330                 335
Lys Leu Ile Lys Asn Asp Gly Arg Asp Ile Asn Gly Ser Ala Ala Ser
             340                 345                 350
Leu Thr Ala Ala Gly Ala Thr Thr Ala Ala Met Ile Ser Val Asn Ala
         355                 360                 365
Ala Ser Leu Gly Glu Ser Lys Gly Val Tyr Ser Phe Thr Gly Ala Asp
370                 375                 380
Val Phe Thr Phe Asp Asp Gly Lys Gly Gly Lys Phe Val Phe Thr
385                 390                 395                 400
Lys Asn Val Ser Ala Ile Lys Ala Asp Leu Glu Ala Ile Asp Phe Gly
                 405                 410                 415
Phe His Val Gly Ala Asp Lys Asp Asn Asn Gly Ala Ala Tyr Ser
             420                 425                 430
Ile Gly Ser Gly Val Leu Ser Gln Gly Ile Ala Ala Gly Asp Ala Lys
```

```
                435                 440                 445
Thr Leu Gly Gly Asn Thr Leu Phe Val Asp Asp Gly Ser Gly Phe Ser
    450                 455                 460

Ser Gly Thr Ala Asn Gly Val Ser Ala Ala Leu Asn Thr Asp Ala Ala
465                 470                 475                 480

Asn Val Thr Asn Ala Gly Tyr Ala Ser Ala Thr Asp Thr Asn Lys Asp
                485                 490                 495

Tyr Ala Pro Ala Ile Gly Lys Ala Val Asn Lys Asp Ala Ala Gly Lys
            500                 505                 510

Asp Glu Thr Asp Ala Ala Thr Thr Gly Lys Ala Ala Thr Asn Pro Leu
        515                 520                 525

Asp Ser Ile Asp Asp Ala Ile Ser Lys Ile Asp Ala Gln Arg Ser Ser
    530                 535                 540

Leu Gly Ala Val Gln Asn Arg Leu Asp Ser Thr Ile Asn Asn Leu Asp
545                 550                 555                 560

Asn Thr Val Thr Asn Leu Thr Ala Ala Glu Ser Arg Ile Arg Asp Ala
                565                 570                 575

Asp Tyr Ala Thr Glu Val Ser Asn Met Ser Lys Ala Asn Ile Leu Ala
            580                 585                 590

Gln Ala Gly Gln Ser Val Leu Ala Gln Ala Asn Gln Val Pro Gln Asn
        595                 600                 605

Val Leu Ser Leu Leu Gln Gly
    610                 615

<210> SEQ ID NO 20
<211> LENGTH: 301
<212> TYPE: PRT
<213> ORGANISM: Aquifex aeolicus
<220> FEATURE:
<221> NAME/KEY: MISC_FEATURE
<222> LOCATION: (1)..(301)
<223> OTHER INFORMATION: Ras-like protein GTPase (AaERA, Era)

<400> SEQUENCE: 20

Met Lys Val Gly Tyr Val Ala Ile Val Gly Lys Pro Asn Val Gly Lys
1               5                   10                  15

Ser Thr Leu Leu Asn Asn Leu Leu Gly Thr Lys Val Ser Ile Ile Ser
                20                  25                  30

Pro Lys Ala Gly Thr Thr Arg Met Arg Val Leu Gly Val Lys Asn Ile
            35                  40                  45

Pro Asn Glu Ala Gln Ile Ile Phe Leu Asp Thr Pro Gly Ile Tyr Glu
        50                  55                  60

Pro Lys Lys Ser Asp Val Leu Gly His Ser Met Val Glu Ile Ala Lys
65                  70                  75                  80

Gln Ser Leu Glu Glu Ala Asp Val Ile Leu Phe Met Ile Asp Ala Thr
                85                  90                  95

Glu Gly Trp Arg Pro Arg Asp Glu Glu Ile Tyr Gln Asn Phe Ile Lys
            100                 105                 110

Pro Leu Asn Lys Pro Val Ile Val Ile Asn Lys Ile Asp Lys Ile
        115                 120                 125

Gly Pro Ala Lys Asn Val Leu Pro Leu Ile Asp Glu Ile His Lys Lys
130                 135                 140

His Pro Glu Leu Thr Glu Ile Val Pro Ile Ser Ala Leu Lys Gly Ala
145                 150                 155                 160

Asn Leu Asp Glu Leu Val Lys Thr Ile Leu Lys Tyr Leu Pro Glu Gly
                165                 170                 175
```

Glu Pro Leu Phe Pro Glu Asp Met Ile Thr Asp Leu Pro Leu Arg Leu
                180                 185                 190

Leu Ala Ala Glu Ile Val Arg Glu Lys Ala Met Met Leu Thr Arg Glu
            195                 200                 205

Glu Val Pro Thr Ser Ile Ala Val Lys Ile Asn Glu Ile Lys Pro Gly
        210                 215                 220

Asp Ala Asn Pro Asn Met Leu Val Ile Lys Gly Glu Ile Ile Val Asp
225                 230                 235                 240

Arg Glu Asn Leu Lys Pro Ile Ile Ile Gly Lys Lys Gly Gln Arg Leu
                245                 250                 255

Lys Glu Ile Gly Lys Arg Ala Arg Gln Glu Leu Glu Leu Ile Leu Gly
            260                 265                 270

Arg Pro Val Tyr Leu Glu Leu Trp Val Lys Val Val Pro Asp Trp Arg
        275                 280                 285

Arg Arg Pro Glu Tyr Val Arg Leu Phe Gly Tyr Ala Leu
                290                 295                 300

<210> SEQ ID NO 21
<211> LENGTH: 301
<212> TYPE: PRT
<213> ORGANISM: Thermus thermophilus
<220> FEATURE:
<221> NAME/KEY: MISC_FEATURE
<222> LOCATION: (1)..(301)
<223> OTHER INFORMATION: Ras-like protein GTPase (TtERA, Era)

<400> SEQUENCE: 21

Met Ala Glu Lys Thr Tyr Ser Gly Phe Val Ala Ile Val Gly Lys Pro
1               5                   10                  15

Asn Val Gly Lys Ser Thr Leu Leu Asn Asn Leu Leu Gly Val Lys Val
            20                  25                  30

Ala Pro Ile Ser Pro Arg Pro Gln Thr Thr Arg Lys Arg Leu Arg Gly
        35                  40                  45

Ile Leu Thr Glu Gly Arg Arg Gln Ile Val Phe Val Asp Thr Pro Gly
    50                  55                  60

Leu His Lys Pro Met Asp Ala Leu Gly Glu Phe Met Asp Gln Glu Val
65                  70                  75                  80

Tyr Glu Ala Leu Ala Asp Val Asn Ala Val Val Trp Val Val Asp Leu
                85                  90                  95

Arg His Pro Pro Thr Pro Glu Asp Glu Leu Val Ala Arg Ala Leu Lys
            100                 105                 110

Pro Leu Val Gly Lys Val Pro Ile Leu Leu Val Gly Asn Lys Leu Asp
        115                 120                 125

Ala Ala Lys Tyr Pro Glu Glu Ala Met Lys Ala Tyr His Glu Leu Leu
130                 135                 140

Pro Glu Ala Glu Pro Arg Met Leu Ser Ala Leu Asp Glu Arg Gln Val
145                 150                 155                 160

Ala Glu Leu Lys Ala Asp Leu Leu Ala Leu Met Pro Glu Gly Pro Phe
                165                 170                 175

Phe Tyr Pro Glu Asp Tyr Ala Lys Ser Asp Gln Thr Phe Gly Glu Trp
            180                 185                 190

Val Ala Glu Ile Leu Arg Glu Glu Ala Met Lys Arg Leu Trp His Glu
        195                 200                 205

Val Pro Tyr Ala Val Ala Thr Lys Val Glu Glu Val Ala Glu Arg Glu
        210                 215                 220

Asn Gly Val Leu Tyr Ile Lys Ala Ile Leu Tyr Val Glu Arg Pro Ser
225                 230                 235                 240

Gln Lys Ala Ile Val Ile Gly Glu Gly Arg Lys Ile Lys Glu Ile
            245                 250                 255

Gly Gln Ala Thr Arg Lys Gln Leu Glu Ala Leu Leu Gly Lys Lys Val
            260                 265                 270

Tyr Leu Asp Leu Glu Val Lys Val Tyr Pro Asp Trp Arg Lys Asp Pro
        275                 280                 285

Glu Ala Leu Arg Glu Leu Gly Tyr Arg Ser Ser Val Gly
    290                 295                 300

<210> SEQ ID NO 22
<211> LENGTH: 301
<212> TYPE: PRT
<213> ORGANISM: Eschericia coli
<220> FEATURE:
<221> NAME/KEY: MISC_FEATURE
<222> LOCATION: (1)..(301)
<223> OTHER INFORMATION: Escherichia coli strain K12 Ras-like protein
      GTPase (EcERA, Era), 16S rRNA-binding GTPase, B2566, SdgE, RbaA

<400> SEQUENCE: 22

Met Ser Ile Asp Lys Ser Tyr Cys Gly Phe Ile Ala Ile Val Gly Arg
1               5                   10                  15

Pro Asn Val Gly Lys Ser Thr Leu Leu Asn Lys Leu Leu Gly Gln Lys
            20                  25                  30

Ile Ser Ile Thr Ser Arg Lys Ala Gln Thr Thr Arg His Arg Ile Val
        35                  40                  45

Gly Ile His Thr Glu Gly Ala Tyr Gln Ala Ile Tyr Val Asp Thr Pro
    50                  55                  60

Gly Leu His Met Glu Glu Lys Arg Ala Ile Asn Arg Leu Met Asn Lys
65                  70                  75                  80

Ala Ala Ser Ser Ser Ile Gly Asp Val Glu Leu Val Ile Phe Val Val
                85                  90                  95

Glu Gly Thr Arg Trp Thr Pro Asp Asp Glu Met Val Leu Asn Lys Leu
            100                 105                 110

Arg Glu Gly Lys Ala Pro Val Ile Leu Ala Val Asn Lys Val Asp Asn
        115                 120                 125

Val Gln Glu Lys Ala Asp Leu Leu Pro His Leu Gln Phe Leu Ala Ser
130                 135                 140

Gln Met Asn Phe Leu Asp Ile Val Pro Ile Ser Ala Glu Thr Gly Leu
145                 150                 155                 160

Asn Val Asp Thr Ile Ala Ala Ile Val Arg Lys His Leu Pro Glu Ala
                165                 170                 175

Thr His His Phe Pro Glu Asp Tyr Ile Thr Asp Arg Ser Gln Arg Phe
            180                 185                 190

Met Ala Ser Glu Ile Ile Arg Glu Lys Leu Met Arg Phe Leu Gly Ala
        195                 200                 205

Glu Leu Pro Tyr Ser Val Thr Val Glu Ile Glu Arg Phe Val Ser Asn
    210                 215                 220

Glu Arg Gly Gly Tyr Asp Ile Asn Gly Leu Ile Leu Val Glu Arg Glu
225                 230                 235                 240

Gly Gln Lys Lys Met Val Ile Gly Asn Lys Gly Ala Lys Ile Lys Thr
                245                 250                 255

Ile Gly Ile Glu Ala Arg Lys Asp Met Gln Glu Met Phe Glu Ala Pro
            260                 265                 270

Val His Leu Glu Leu Trp Val Lys Val Lys Ser Gly Trp Ala Asp Asp
            275                 280                 285

Glu Arg Ala Leu Arg Ser Leu Gly Tyr Val Asp Asp Leu
    290                 295                 300

<210> SEQ ID NO 23
<211> LENGTH: 425
<212> TYPE: PRT
<213> ORGANISM: Escherichia coli
<220> FEATURE:
<221> NAME/KEY: MISC_FEATURE
<222> LOCATION: (1)..(425)
<223> OTHER INFORMATION: Escherichia coli strain K12 4-aminobutyrate
      aminotransferase (EcGabT, GabT)

<400> SEQUENCE: 23

Asn Ser Asn Lys Glu Leu Met Gln Arg Arg Ser Gln Ala Ile Pro Arg
1               5                   10                  15

Gly Val Gly Gln Ile His Pro Ile Phe Ala Asp Arg Ala Glu Asn Cys
            20                  25                  30

Arg Val Trp Asp Val Glu Gly Arg Glu Tyr Leu Asp Phe Ala Gly Gly
        35                  40                  45

Ile Ala Val Leu Asn Thr Gly His Leu His Pro Lys Val Val Ala Ala
    50                  55                  60

Val Glu Ala Gln Leu Lys Lys Leu Ser His Thr Cys Phe Gln Val Leu
65                  70                  75                  80

Ala Tyr Glu Pro Tyr Leu Glu Leu Cys Glu Ile Met Asn Gln Lys Val
                85                  90                  95

Pro Gly Asp Phe Ala Lys Lys Thr Leu Leu Val Thr Thr Gly Ser Glu
            100                 105                 110

Ala Val Glu Asn Ala Val Lys Ile Ala Arg Ala Ala Thr Lys Arg Ser
        115                 120                 125

Gly Thr Ile Ala Phe Ser Gly Ala Tyr His Gly Arg Thr His Tyr Thr
    130                 135                 140

Leu Ala Leu Thr Gly Lys Val Asn Pro Tyr Ser Ala Gly Met Gly Leu
145                 150                 155                 160

Met Pro Gly His Val Tyr Arg Ala Leu Tyr Pro Cys Pro Leu His Gly
                165                 170                 175

Ile Ser Glu Asp Asp Ala Ile Ala Ser Ile His Arg Ile Phe Lys Asn
            180                 185                 190

Asp Ala Ala Pro Glu Asp Ile Ala Ala Ile Val Ile Glu Pro Val Gln
        195                 200                 205

Gly Glu Gly Gly Phe Tyr Ala Ser Ser Pro Ala Phe Met Gln Arg Leu
    210                 215                 220

Arg Ala Leu Cys Asp Glu His Gly Ile Met Leu Ile Ala Asp Glu Val
225                 230                 235                 240

Gln Ser Gly Ala Gly Arg Thr Gly Thr Leu Phe Ala Met Glu Gln Met
                245                 250                 255

Gly Val Ala Pro Asp Leu Thr Thr Phe Ala Lys Ser Ile Ala Gly Gly
            260                 265                 270

Phe Pro Leu Ala Gly Val Thr Gly Arg Ala Glu Val Met Asp Ala Val
        275                 280                 285

Ala Pro Gly Gly Leu Gly Gly Thr Tyr Ala Gly Asn Pro Ile Ala Cys
    290                 295                 300

Val Ala Ala Leu Glu Val Leu Lys Val Phe Glu Gln Glu Asn Leu Leu
305                 310                 315                 320

-continued

```
Gln Lys Ala Asn Asp Leu Gly Gln Lys Leu Lys Asp Gly Leu Leu Ala
                325                 330                 335

Ile Ala Glu Lys His Pro Glu Ile Gly Asp Val Arg Gly Leu Gly Ala
            340                 345                 350

Met Ile Ala Ile Glu Leu Phe Glu Asp Ser Asp His Asn Lys Pro Asp
        355                 360                 365

Ala Lys Leu Thr Ala Glu Ile Val Ala Arg Ala Arg Asp Lys Gly Leu
    370                 375                 380

Ile Leu Leu Ser Cys Gly Pro Tyr Tyr Asn Val Leu Arg Ile Leu Val
385                 390                 395                 400

Pro Leu Thr Ile Glu Asp Ala Gln Ile Arg Gln Gly Leu Glu Ile Ile
            405                 410                 415

Ser Gln Cys Phe Asp Glu Ala Lys Gln
            420                 425
```